US005927988A

United States Patent [19]
Jenkins et al.

[11] Patent Number: 5,927,988
[45] Date of Patent: *Jul. 27, 1999

[54] METHOD AND APPARATUS FOR TRAINING OF SENSORY AND PERCEPTUAL SYSTEMS IN LLI SUBJECTS

[76] Inventors: William M. Jenkins, 348 Farallon Ave., Pacifica, Calif. 94044; Michael M. Merzenich, 20 Hillpoint, San Francisco, Calif. 94117; Steven Lamont Miller, 5 Elk Ct., Pacifica, Calif. 94044; Bret E. Peterson, 3156 Sun Ridge Ct., Lafayette, Calif. 94549; Paula Tallal, 3703 River Rd., Bucks County, Lumberville, Pa. 18933

[*] Notice: This patent issued on a continued prosecution application filed under 37 CFR 1.53(d), and is subject to the twenty year patent term provisions of 35 U.S.C. 154(a)(2).

This patent is subject to a terminal disclaimer.

[21] Appl. No.: 08/982,189

[22] Filed: Dec. 17, 1997

[51] Int. Cl.⁶ ...................................................... G06K 9/00
[52] U.S. Cl. .......................... 434/116; 434/118; 434/169; 434/307 R; 704/270; 704/503; 704/504
[58] Field of Search ..................................... 434/118, 112, 434/116, 156, 157, 167, 169, 185, 307 R, 308, 365; 704/243, 265, 270, 503, 504

[56] References Cited

U.S. PATENT DOCUMENTS 3,816,664   6/1974   Koch .
3,920,903  11/1975   Beller .

(List continued on next page.)

FOREIGN PATENT DOCUMENTS

WO96/18184   6/1996   WIPO .

OTHER PUBLICATIONS

"Decelerated Synthesized Speech as a Means of Shaping Speed of Auditory Processing of Children with Delayed Language", Perceptual and Motor Skills, 1982, vol. 55, pp. 783–792.

Sloan, C., "Treating Auditory Processing Difficulties in Children,", Singular Publishing Group, Inc., San Diego, CA (1986; reprinted 1991), pp. 35–55, 57–61 and 63–82.

Sloan, C., "Auditory Processing Disorders in Children: Diagnosis and Treatment", pp. 117–133, Grune & Stratton, New York, New York (1980).

Elliott, L., Hammer, M., Schol, M., Carrell, T., and Wasowicz, J., "Discrimination of Rising and Falling Simulated Single–Formant Frequency Transitions: Practice and Transition Duration Effects", J. Acoust. Soc. Am. 86(3), 1989, pp. 945–953.

Flowers, A. "CAA Program Level III 3 Basic Phonemic Identification Level (Phonemic Closure)", pp. 133–138, Perceptual Learning Systems, Dearborn, Michigan, 1983.

(List continued on next page.)

Primary Examiner—Joe H. Cheng
Attorney, Agent, or Firm—James W. Huffman; Kang S. Lim

[57] ABSTRACT

An apparatus and method for training the sensory perceptual system in a language learning impaired (LLI) subject is provided. The apparatus and method incorporates a number of different programs to be played by the subject. The programs artificially process selected portions of language elements, called phonemes, so they will be more easily distinguished by an LLI subject, and gradually improves the subject's neurological processing of the elements through repetitive stimulation. The programs continually monitor a subject's ability to distinguish the processed language elements, and adaptively configures the programs to challenge and reward the subject by altering the degree of processing. Through adaptive control and repetition of processed speech elements, and presentation of the speech elements in a creative fashion, a subject's temporal processing of acoustic events common to speech are significantly improved.

54 Claims, 24 Drawing Sheets

U.S. PATENT DOCUMENTS

| | | | |
|---|---|---|---|
| 4,010,557 | 3/1977 | Martin et al. . | |
| 4,128,737 | 12/1978 | Dorais | 704/265 |
| 4,327,252 | 4/1982 | Tomatis . | |
| 4,464,119 | 8/1984 | Vildgrube et al. . | |
| 4,586,905 | 5/1986 | Groff . | |
| 4,641,343 | 2/1987 | Holland et al. . | |
| 4,696,042 | 9/1987 | Goudie . | |
| 4,708,657 | 11/1987 | Beller et al. . | |
| 4,736,429 | 4/1988 | Niyada et al. . | |
| 4,741,037 | 4/1988 | Goldstern . | |
| 4,799,261 | 1/1989 | Lin et al. . | |
| 4,813,076 | 3/1989 | Miller | 704/254 |
| 4,820,059 | 4/1989 | Miller et al. | 704/254 |
| 4,821,325 | 4/1989 | Martin et al. . | |
| 4,852,168 | 7/1989 | Sprague . | |
| 4,852,170 | 7/1989 | Bordeaux . | |
| 4,884,972 | 12/1989 | Gasper . | |
| 4,895,519 | 1/1990 | Beller et al. . | |
| 4,907,274 | 3/1990 | Nomura et al. | 704/270 |
| 4,980,917 | 12/1990 | Hutchins . | |
| 5,010,495 | 4/1991 | Willetts . | |
| 5,056,143 | 10/1991 | Taguchi . | |
| 5,119,826 | 6/1992 | Baart De La Faille . | |
| 5,123,048 | 6/1992 | Miyamae et al. . | |
| 5,169,342 | 12/1992 | Steele et al. . | |
| 5,215,468 | 6/1993 | Lauffer et al. . | |
| 5,285,498 | 2/1994 | Johnston . | |
| 5,289,521 | 2/1994 | Coleman et al. . | |
| 5,295,223 | 3/1994 | Saito . | |
| 5,302,132 | 4/1994 | Corder . | |
| 5,305,420 | 4/1994 | Nakamura et al. . | |
| 5,340,316 | 8/1994 | Javkin et al. . | |
| 5,341,432 | 8/1994 | Suzuki et al. . | |
| 5,387,104 | 2/1995 | Corder . | |
| 5,393,236 | 2/1995 | Blackmer et al. | 434/169 |
| 5,421,731 | 6/1995 | Walker . | |
| 5,429,513 | 7/1995 | Diaz-Plaza . | |
| 5,487,671 | 1/1996 | Shpiro et al. | 434/185 |
| 5,517,595 | 5/1996 | Kleijn . | |
| 5,536,171 | 7/1996 | Javkin et al. . | |
| 5,540,589 | 7/1996 | Waters | 434/156 |
| 5,562,453 | 10/1996 | Wen . | |
| 5,573,403 | 11/1996 | Beller et al. . | |
| 5,690,493 | 11/1997 | McAlear, Jr. | 434/178 |
| 5,697,789 | 12/1997 | Sameth et al. . | |
| 5,717,828 | 2/1998 | Rothenberg | 704/270 |
| 5,741,136 | 4/1998 | Kirksey et al. | 434/169 |
| 5,765,135 | 6/1998 | Friedman et al. | 704/270 X |
| 5,766,015 | 6/1998 | Shpiro . | |
| 5,791,904 | 8/1998 | Russell et al. | 434/185 |

OTHER PUBLICATIONS

Fiez, J. et al, "PET Studies of Auditory and Phonological Processing: Effects of Stimulus Characteristics and Task Demands", 1995, Journal of Cognitive Neuroscience : 7(3), pp. 357–375.

Merzenich, M. et al, "Cortical Plasticity, Learning, and Language Dysfunction", 1995, SFI Studies in Science of Complexity, vol. XXIII, pp. 247–272.

Fiez, J. et al, "PET Activation of Posterior Temporal Regions During Auditory Word Presentation and Verb Generation", Jan./Feb. 1996, Cerebral Cortex, vol. 6, pp. 1–9.

Barinaga, M., "Giving Language Skills a Boost", Jan. 5, 1996, Science, vol. 271, pp.27–28.

Merzenich, M. et al, "Temporal Processing Deficits of Language–Learning Impaired Children Ameliorated by Training", Jan. 5, 1996, Science, vol. 271, pp. 77–81.

Merzenich, M. et al, "Cortical Plasticity Underlying Perceptual, Motor, and Cognitive Skill Development: Implications for Neurorehabilitation", 1996, Cold Spring Harbor Symposia on Quantitative Biology, vol. LXI, pp. 1–8.

"Phonological Awareness Training and Remediation of Analytic Decoding Deficits in a Group of Severe Dyslexics" by Alexander et al, Annals of Dyslexia, vol. 41: 193–206, 1991.

"Auditory Integration Training for Individuals with Autism" by Berkell et al, Education and Training in Mental Retardation and Developmental Disabilities, pp. 66–70, Mar. 1996.

"Hearing Equal Behavior" by G. Bérard, Keats Publishing, Inc., pp. 77–93, 1993.

"Crazy sounds to soothe a garbled world" by J. Burne, The Independent II, p. 24, 1994.

"Understanding Compressed Sentences: The Role of Rhythm and Meaning" by Mehler et al, Annals New York Academy of Sciences, vol. 682: 272–282, 1993.

"Summaries of Research on Auditory Integration Training (1993–1995: 11 Studies)" by B. Rimland, Autism Research Institute, 1995.

"Brief Report: A Pilot Study of Auditory Integration Training in Autism" by Rimland et al, Journal of Autism and Developmental Disorders, vol. 25, No. 1: 61–70, 1995.

"Defects of Non–Verbal Auditory Perception in Children with Developmental Aphasia" by Tallal et al, Nature, vol. 241: 468–469, Feb. 1973.

"Developmental Aphasia: Impaired Rate of Non–verbal Processing as a Function of Sensory Modality" by Tallal et al,Neuropsychologia, vol. 11: 389–398, 1973.

"Developmental Aphasia: Rate of Auditory Processing and Selective Implairment of Consonant Perception" by Tallal et al, Neuropsychologia, vol. 12: 83–93, 1974.

"Developmental Aphasia: The Perception of Brief Vowels and Extended Stop Consonants" by Tallel et al, Neuropsychologia, vol. 13: 69–74, 1975.

"Language Comprehension in Language–Learning Impaired Children Inproved with Acoustically Modified Speech" by Tallal et al,Svience, vol. 271: 81–84, Jan. 1996.

"Neurobiological Basis of Speech: A Case for the Preeminence of Temporal Processing" by Tallal et al, Annals New York Academy of Sciences, vol. 682: 27–47, 1993.

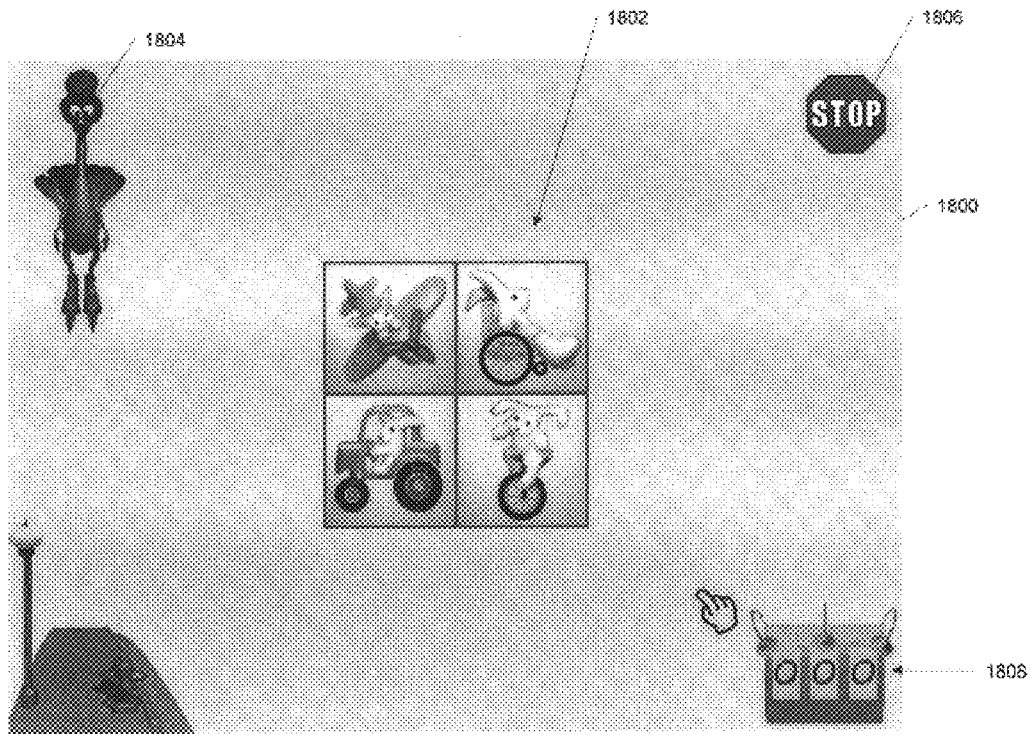

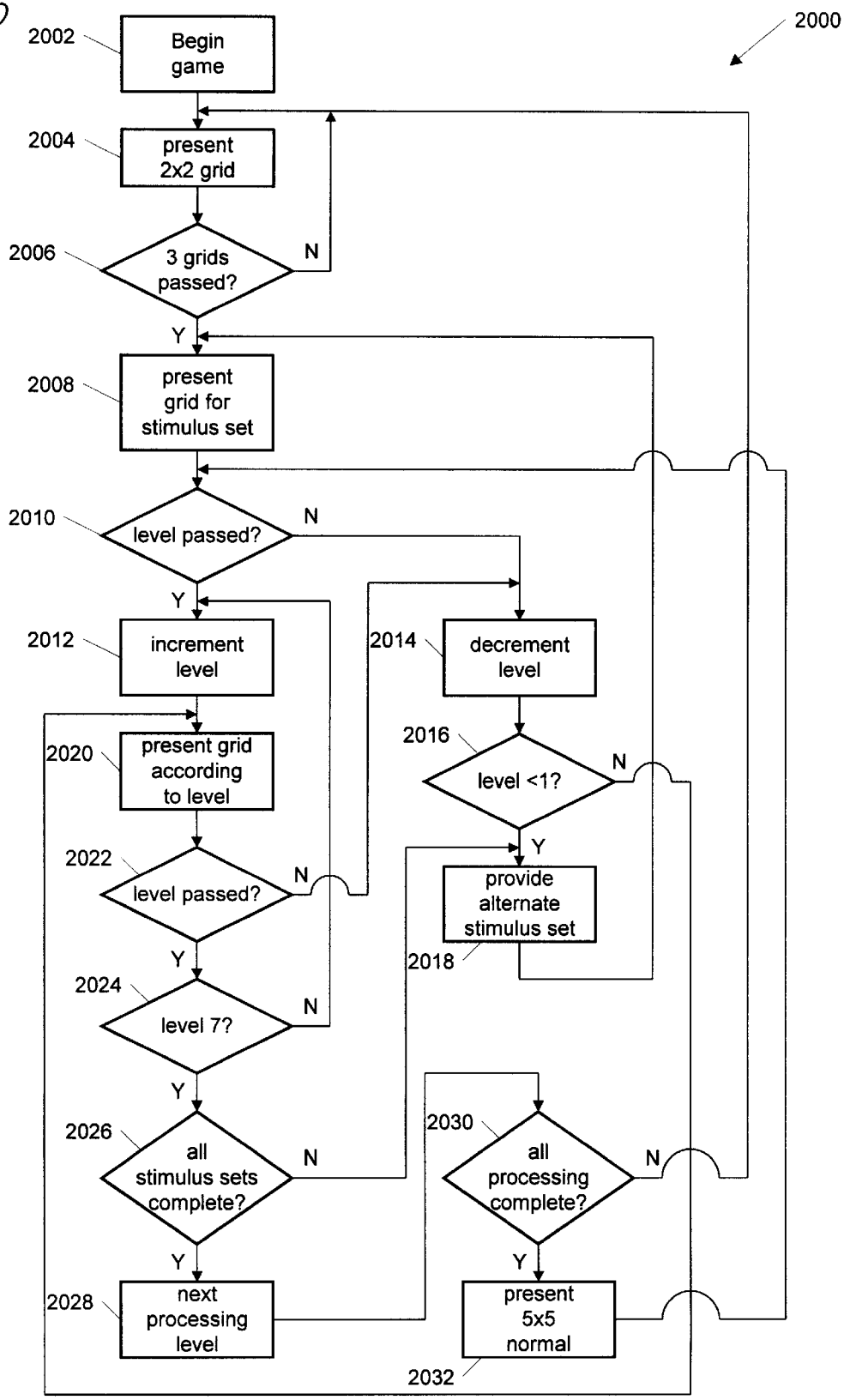

METHOD AND APPARATUS FOR TRAINING OF SENSORY AND PERCEPTUAL SYSTEMS IN LLI SUBJECTS

CROSS REFERENCE TO RELATED APPLICATIONS

This application is related to co-pending U.S. patent application Ser. No. 08/992,071 (Docket SLC:707C) filed Dec. 17, 1997, entitled "METHOD AND APPARATUS FOR TRAINING OF SENSORY AND PERCEPTUAL SYSTEMS IN LLI SUBJECTS"; and U.S. patent application Ser. No. 08/992,072 (Docket SLC:707B), filed Dec. 17, 1997, entitled "METHOD AND APPARATUS FOR TRAINING OF COGNITIVE AND MEMORY SYSTEMS IN HUMANS"; both assigned to Scientific Learning Corporation.

BACKGROUND OF THE INVENTION

1. Field of the Invention

This invention relates in general to the field of education in language learning impaired (LLI) subjects, and more specifically to a computer program for training the auditory processing system in subjects having receptive language problems.

2. Description of the Related Art

Up to ten percent of children have language-learning impairments (LLI) resulting from the inability to accurately process short duration acoustic events at the rates that occur in normal speech. Their trouble distinguishing among elements of speech is neurologically based and has far reaching consequences: academic failure, emotional and disciplinary problems, and possibly diminished lifelong achievement and self-image. No bracket of intelligence, race, gender or economic level is immune from this problem.

More specifically, Children with LLI have difficulty detecting and identifying sounds that occur simultaneously or in close proximity to each other—a phenomenon known as "masking." Because of masking, children with LLI require sounds that are as much as 45 decibels more intense than the preceding or subsequent masking noise to distinguish and understand them. In addition, children with LLI are consistently poorer at detecting a brief tone presented with a masking noise, particularly when the brief tone is turned on immediately prior to the masking noise. This phenomenon is called "backward masking." Similarly, when the brief tone is turned on immediately after the masking noise a similar decrease in detectability can occur. This phenomenon is called "forward masking". For a tone to be detected by a child with LLI in the presence of a masking noise, the tone must be separated in time or frequency from the masking noise.

The inability to accurately distinguish and process short duration sounds often causes children to fall behind in school. Since the children can't accurately interpret many language sounds, they can't remember which symbols represent which sounds. This deficiency causes difficulties in learning to read (translating from symbols to sounds), and in spelling. In fact, it is common for a child with LLI to fall two to three years behind his/her peers in speech, language and reading development.

One way children develop such auditory processing problems is from middle ear infections when they are young and beginning to develop the oral representations of language in the central auditory nervous system. When a child has an ear infection, fluid can build up and block or muffle the sound wave entering the ear causing intermittent hearing loss. Even if the infection doesn't permanently damage the ear, the child's brain doesn't learn to process some sounds because it hasn't heard them accurately before, on a consistent basis. This typically occurs during a critical period of brain development when the brain is building the nerve connections necessary to accurately process acoustic events associated with normal speech.

Researchers believe that the auditory processing problem is essentially one of timing. Vowel sounds like /a/ and /e/ usually last at least 100 milliseconds and typically have constant frequency content. Consonants, on the other hand, typically have modulated frequency components, and last less than 40 milliseconds. Children with LLI cannot process these faster speech elements, especially the hard consonants like /t/, /p/, /d/ and /b/, if they occur either immediately before or after vowels, or if they are located near other consonants. Rather than hearing the individual sounds that make up a particular phoneme, children with LLI integrate closely associated sounds together over time. Since the duration of vowels are typically longer than consonants, the modulated frequency portions of consonants are often lost in the integration, an affect that may also hinder the resolution of the vowel, particularly short duration vowels.

This problem of abnormal temporal integration of acoustic events over time is not limited to children with LLI. Rather, the problem extends to stroke victims who have lost the neurological connections necessary to process speech, as well as to individuals raised in one country, having one set of language phonemes, and attempting to learn the language of another country, having a distinct set of language phonemes. For example, it is known that an individual raised in Japan is not often presented with phonemes similar to the English r's and l's, because those consonants are not common in the Japanese language. Similarly, there are many subtleties in the sounds made by a speaker of Japanese that are difficult to distinguish unless raised in Japan. The phonetic differences between languages are distinctions that must be learned, and are often very difficult. But, they are clearly problems that relate to the temporal processing of short duration acoustic events.

The above described temporal processing deficiency has little if anything to do with intelligence. In fact, some LLI specialists argue that brains choosing this different route by which to absorb and reassemble bits of speech may actually stimulate creative intelligence, but at the expense of speech and reading problems.

Recent studies have shown that if the acoustic events associated with phonemes that are difficult to distinguish, such as /ba/ and /da/, are slowed down, or that the consonant portion of the phonemes are emphasized, that students diagnosed as LLI can accurately distinguish between the phonemes. In addition, if the interval between two complex sounds is lengthened, LLI students are better able to process the sounds distinctly.

Heretofore, the solution to the processing problem has been to place LLI students in extended special education and/or speech therapy training programs that focus on speech recognition and speech production. Or, more commonly, repetitive reading programs, phonic games, or other phonic programs are undertaken. These programs often last for years, with a success rate that is often more closely associated with the skill of the speech and language professional than with the program of study.

What is needed is a method and apparatus that allows a subject with abnormal temporal processing to train, or retrain their brain to recognize and distinguish short duration acoustic events that are common in speech. Moreover, what is needed is a program that repetitively trains a subject to distinguish phonemes at a normal rate, by first stretching, and/or emphasizing elements of speech to the point that they are distinguishable, or separating speech elements in time, and then adaptively adjusting the stretching, emphasis and separation of the speech elements to the level of normal speech. The adaptive adjustments should be made so as to encourage the subject to continue with the repetitions, and the number of repetitions should be sufficient to develop the necessary neurological connections for normal temporal processing of speech. Moreover, the program should provide acoustic signals to the brain that are better for phonetic training than normal human speech.

SUMMARY

To address the above-detailed deficiencies, the present invention provides a method for training the sensory, perceptual and cognitive systems in a human. The method repetitively provides a first acoustic event to the human, where the first acoustic event is stretched in the time domain. The method then sequentially provides a second acoustic event to the human for recognition. The method then requires the human to recognize the second acoustic event within a predetermined time window. If the human recognizes the second acoustic event within the predetermined time window, the amount of stretching applied to the first acoustic event is reduced.

By repetitively providing two acoustic events, stretched in the time domain, to the subject, and by reducing the amount of stretching applied to the acoustic events, as the subject correctly distinguishes between the events, the sensory, perceptual and cognitive systems of the human is trained.

In another aspect, a method is provided for training an LLI subject to distinguish between frequency sweeps common in phonemes. The method presents a first frequency sweep that increases in frequency. The method also presents a second frequency sweep that decreases in frequency. The order of presenting the first and second frequency sweeps is random. The first and second frequency sweeps are separated by an inter-stimulus interval (ISI). After presenting the frequency sweeps, the method requires an individual to recognize the order of presentation of the first and second frequency sweeps. The ISI separating the first and second frequency sweeps is reduced or increased as the individual recognizes or fails to recognize the order of presentation, respectively. In addition, the duration of the first and second frequency sweeps is reduced as the individual repeatedly recognizes their order of presentation. By randomly presenting frequency sweeps to a subject, separated by an ISI, and by adaptively varying the duration of the sweeps, and the ISI according to the correct or incorrect recognition by the subject, the subject is trained to better distinguish between common phonemes having similar frequency characteristics.

In yet another aspect, the present invention provides an adaptive method for improving a user's discrimination of short duration acoustic events. The method displays a plurality of graphical images that are associated with modified acoustic events. The graphical images are associated in pairs with particular modified acoustic events such that two different graphical images are associated with a particular modified acoustic event. When any of the plurality of graphical images are selected, its associated modified acoustic event is presented. The method requires the user to discriminate between the acoustic events by sequentially selecting two different graphical images that are associated with the same modified acoustic event, from among all of the graphical images. When the user sequentially selects two images corresponding to the same modified acoustic event, those images are removed from the set of all graphical images. As the user continues to sequentially select two images corresponding to the same modified acoustic event, the number of graphical images displayed increases, and the amount which the acoustic events are modified is reduced.

The present invention also provides a method to train a subject to discriminate between similar acoustic events commonly found in spoken language. The method utilizes a computer for displaying images, for modifying the similar acoustic events, and for acoustically producing the modified similar acoustic events to the subject. The method selects a pair of words that have similar acoustic properties, displays a pair of graphical images representative of each of the pair of words, modifies one of the pair of words by stretching it in the time domain, acoustically produces the modified word to the subject, and requires the subject to select from the pair of graphical images, an image representative of the produced modified word. If the subject correctly selects the graphical image representative of the modified word, a different word is similarly presented. After repeated correct selections, the amount of stretching applied to the words is reduced.

In yet another aspect, it is a feature of the present invention to provide a method for repetitively and adaptively training a subject that has subnormal temporal acoustic processing capabilities to distinguish between phonemes that have similar acoustic characteristics. The method provides a plurality of phoneme pairs, where each pair has similar acoustic characteristics. For each of the plurality of phoneme pairs, the method provides a pair of associated graphic images. The method selects from among the plurality of phoneme pairs, a phoneme pair to be presented to the subject. The selected phoneme pair is then processed according to a predetermined skill level. After processing, the processed selected phoneme pair is presented to the subject. As a trial, the subject is required to recognize one of the processed phonemes from the selected phoneme pair by selecting its associated graphic image. Finally, the above trial is repeated. As the subject correctly recognizes the appropriate phoneme from the phoneme pair, the skill level is increased. That is, the amount of processing applied to the phoneme pairs is reduced.

BRIEF DESCRIPTION OF THE DRAWINGS

These and other objects, features, and advantages of the present invention will become better understood with regard to the following description, and accompanying drawings where:

FIG. 18 is a pictorial representation of a game entitled "Phonic Match" according to the present invention.

FIG. 19 includes two tables illustrating the processing levels and the training levels embodied in the game Phonic Match.

FIG. 20 is a flow chart illustrating the adaptive auditory training process embodied in the game Phonic Match.

DETAILED DESCRIPTION

Figure 1:
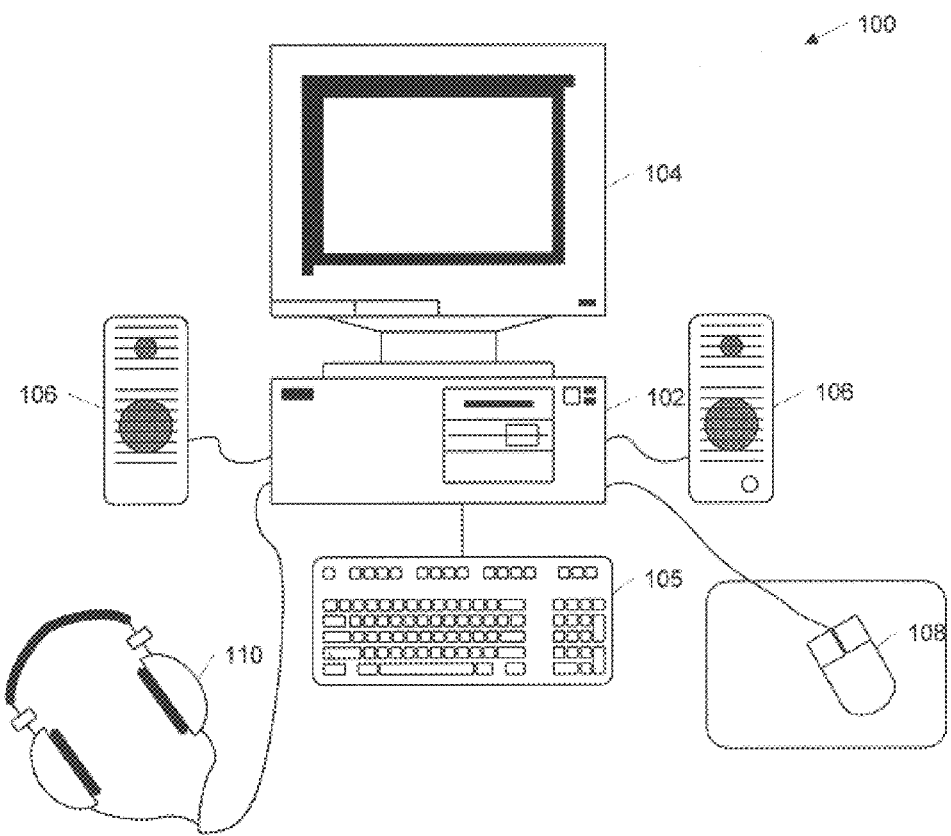
FIG. 1 is a block diagram of a computer system for executing a program according to the present invention.

Referring to FIG. 1, a computer system 100 is shown for executing a computer program to train, or retrain a learning language impaired (LLI) subject, according to the present invention. The computer system 100 contains a computer 102, having a CPU, memory, hard disk and CD ROM drive (not shown), attached to a monitor 104. The monitor 104 provides visual prompting and feedback to the subject during execution of the computer program. Attached to the computer 102 are a keyboard 105, speakers 106, a mouse 108, and headphones 110. The speakers 106 and the headphones 110 provide auditory prompting and feedback to the subject during execution of the computer program. The mouse 108 allows the subject to navigate through the computer program, and to select particular responses after visual or auditory prompting by the computer program. The keyboard 105 allows an instructor to enter alpha numeric information about the subject into the computer 102. Although a number of different computer platforms are applicable to the present invention, embodiments of the present invention execute on either IBM compatible computers or Macintosh computers.

Figure 2:
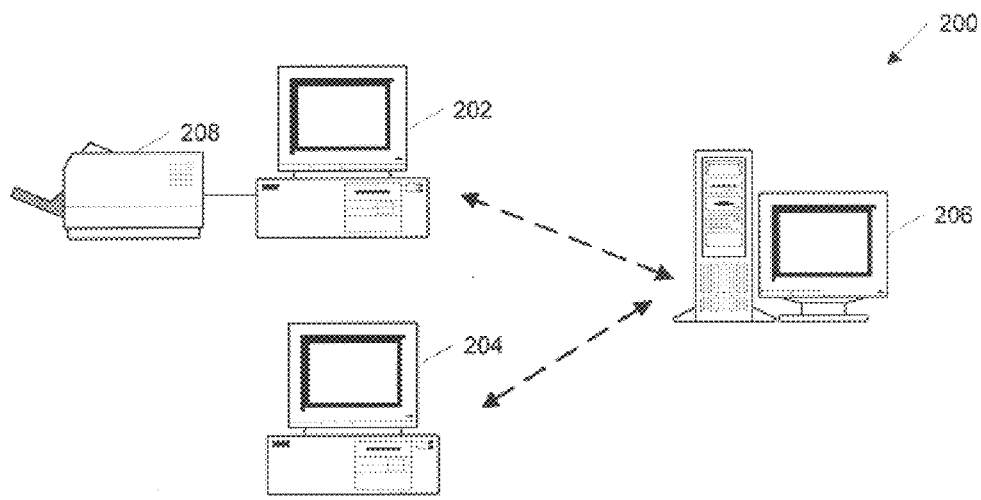
FIG. 2 is a block diagram of a computer network for executing a program according to the present invention.

Now referring to FIG. 2, a computer network 200 is shown. The computer network 200 contains computers 202, 204, similar to that described above with reference to FIG. 1, connected to a server 206. The connection between the computers 202, 204 and the server 206 can be made via a local area network (LAN), a wide area network (WAN), or via modem connections, directly or through the Internet. A printer 208 is shown connected to the computer 202 to illustrate that a subject can print out reports associated with the computer program of the present invention. The computer network 200 allows information such as test scores, game statistics, and other subject information to flow from a subject's computer 202, 204 to a server 206. An administrator can then review the information and can then download configuration and control information pertaining to a particular subject, back to the subject's computer 202, 204. Details of the type of information passed between a subject's computer and a server are provided in co-pending U.S. application Ser. No. 08/995,680 entitled "Remote Computer-Assisted Professionally Supervised Teaching System", assigned to Scientific Learning Corporation.

Before providing a detailed description of the present invention, a brief overview of certain components of speech will be provided, along with an explanation of how these components are processed by LLI subjects. Following the overview, general information on speech processing will be provided so that the reader will better appreciate the novel aspects of the present invention.

Figure 3:
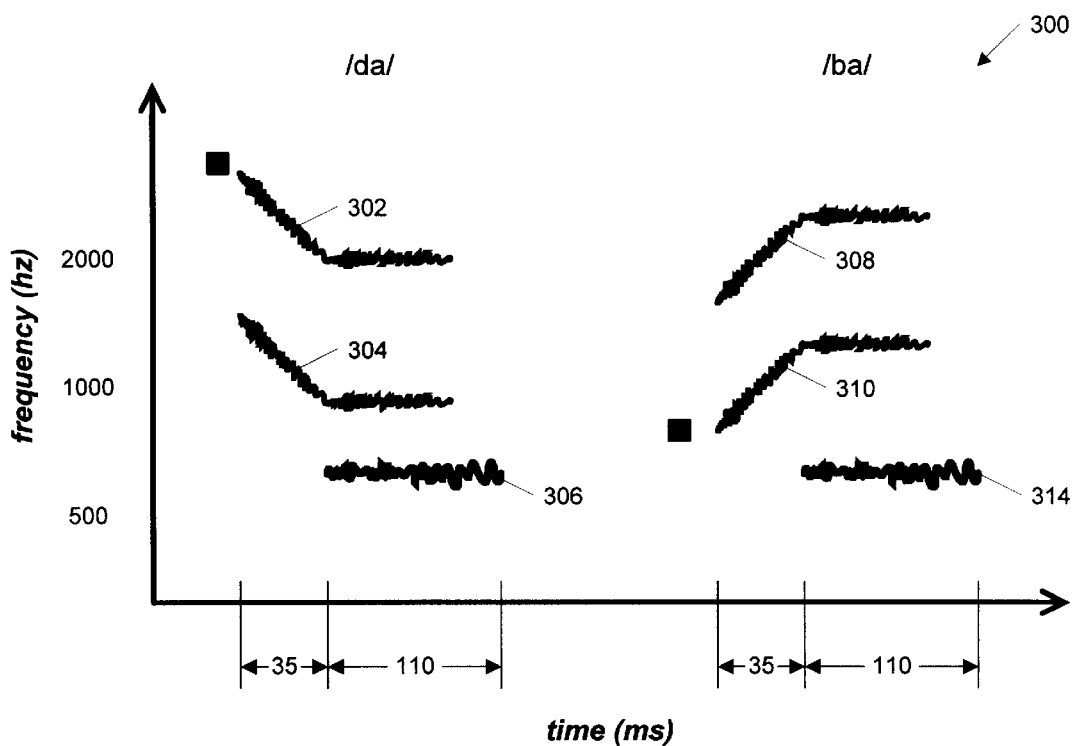
FIG. 3 is a chart illustrating frequency/energy characteristics of two phonemes within the English language.

Referring to FIG. 3, a chart is shown that illustrates frequency components, over time, for two distinct phonemes within the English language. Although different phoneme combinations are applicable to illustrate features of the present invention, the phonemes /daa/ and /ba/ are shown. For the phoneme /da/, a downward sweep frequency component 302, at approximately 2.5–2 khz is shown to occur over a 35 ms interval. In addition, a downward sweep frequency component 304, at approximately 1 khz is shown to occur during the same 35 ms interval. At the end of the 35 ms interval, a constant frequency component 306 is shown, whose duration is approximately 110 ms. Thus, in producing the phoneme /da/, the stop consonant portion of the element /d/ is generated, having high frequency sweeps of short duration, followed by a long vowel element /a/ of constant frequency.

Also shown are frequency components for a phoneme /ba/. This phoneme contains an upward sweep frequency component 308, at approximately 2 khz, having a duration of approximately 35 ms. The phoneme also contains an upward sweep frequency component 310, at approximately 1 khz, during the same 35 ms period. Following the stop consonant portion /b/ of the phoneme, is a constant frequency vowel portion 314 whose duration is approximately 110 ms.

Thus, both the /ba/ and /da/ phonemes begin with stop consonants having modulated frequency components of relatively short duration, followed by a constant frequency vowel component of longer duration. The distinction between the phonemes exist primarily in the 2 khz sweeps during the initial 35 ms interval. Similarity exists between other stop consonants such as /ta/, /pa/, /ka/ and /ga/.

Figure 4:
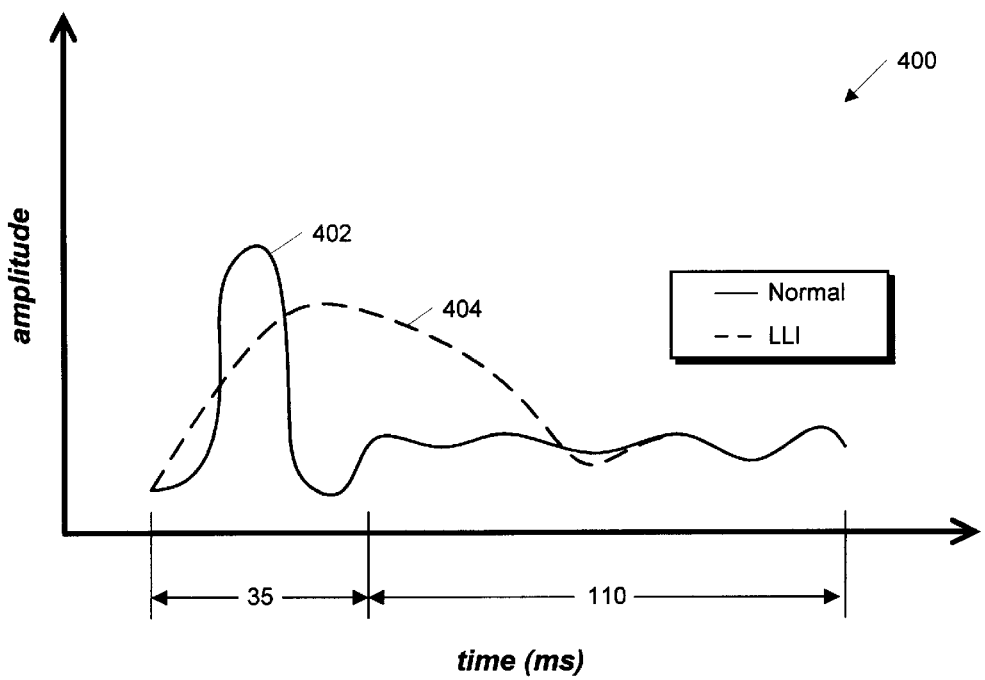
FIG. 4 is a chart illustrating auditory reception of a phoneme by a subject having normal receptive characteristics, and by a subject whose receptive processing is impaired.

Referring now to FIG. 4, the amplitude of a phoneme, for example /ba/, is viewed in the time domain. A short duration high amplitude peak waveform 402 is created upon release of either the lips or the tongue when speaking the consonant portion of the phoneme, that rapidly declines to a constant amplitude signal of longer duration. For an individual with normal temporal processing, the waveform 402 will be understood and processed essentially as it is. However, for an individual who is learning-language impaired, or who has abnormal temporal processing, the short duration, higher frequency consonant burst will be integrated over time with the lower frequency vowel, and depending on the degree of impairment, will be heard as the waveform 404. The result is that the information contained in the higher frequency sweeps associated with consonant differences, will be muddled, or indistinguishable.

With the above general background of speech elements, and how LLI subjects process them, a general overview of speech processing will now be provided. As mentioned above, one problem that exists in LLI subjects is the inability to distinguish between short duration acoustic events. If the duration of these acoustic events are stretched, in the time domain, it is possible to train LLI subjects to distinguish between these acoustic events. An example of such time domain stretching is shown in FIG. 5, to which attention is now directed.

Figure 5:
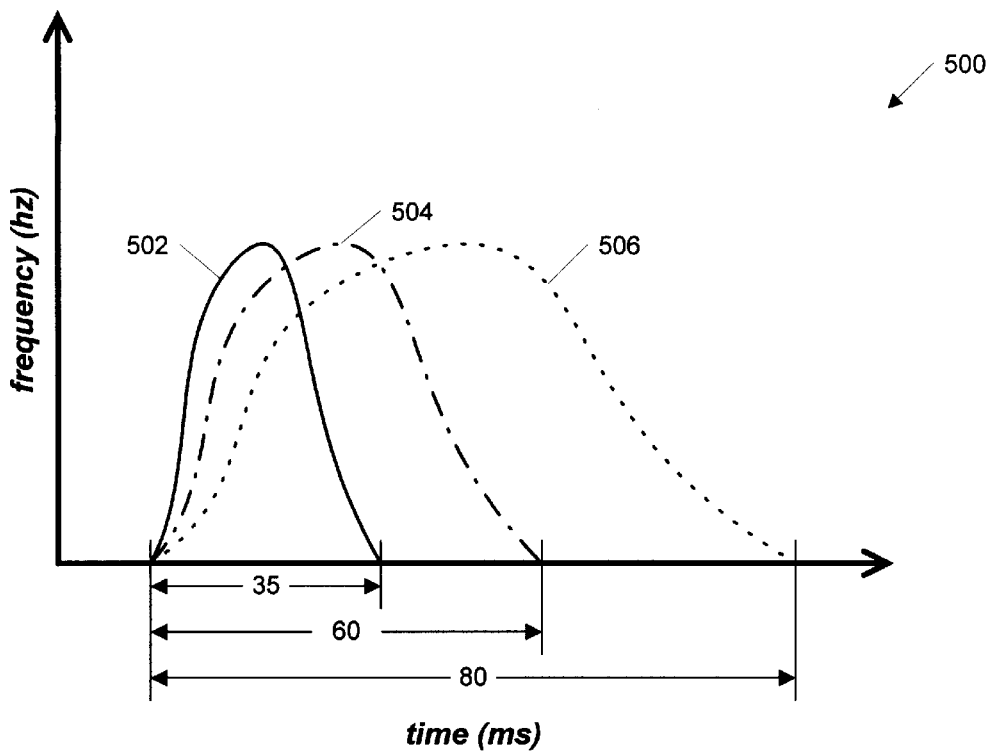
FIG. 5 is a chart illustrating stretching of a frequency envelope in time, according to the present invention.

In FIG. 5, a frequency vs. time graph 500 is shown that illustrates a waveform 502 having short duration characteristics similar to the waveform 402 described above. Using existing computer technology, the analog waveform 502 can be sampled and converted into digital values (using a Fast Fourier Transform, for example) . The values can then be manipulated so as to stretch the waveform in the time domain to a predetermined length, while preserving the amplitude and frequency components of the modified waveform. The modified waveform can then be converted back into an analog waveform (using an inverse FFT) for reproduction by a computer, or by some other audio device. The waveform 502 is shown stretched in the time domain to durations of 60 ms (waveform 504), and 80 ms (waveform 506). By stretching the consonant portion of the waveform 502 without effecting its frequency components, subjects with LLI can begin to hear distinctions in common phonemes.

Figure 6:
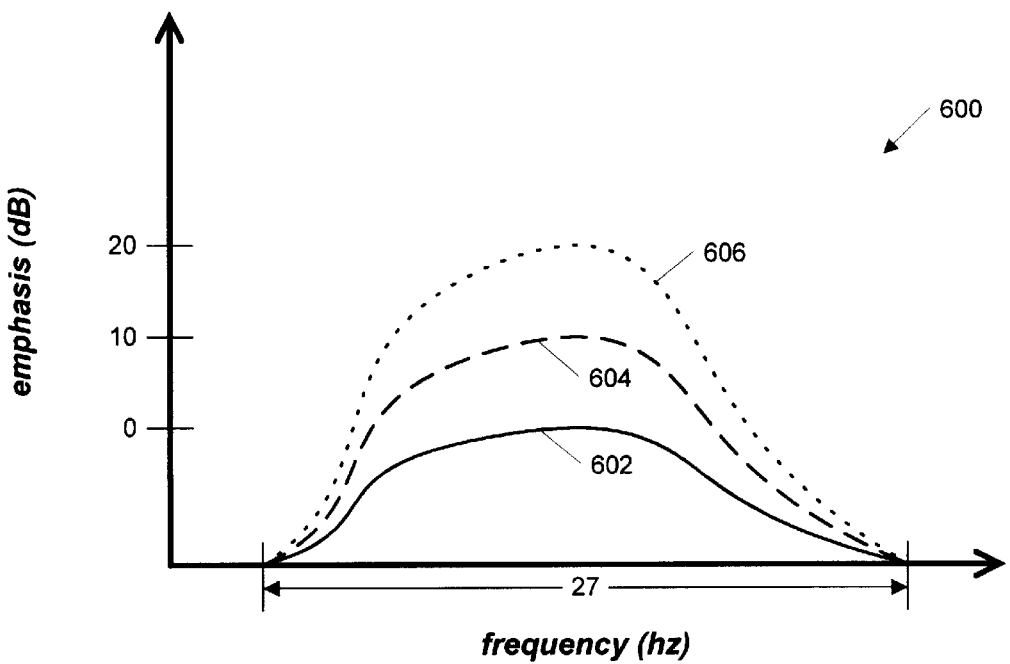
FIG. 6 is a chart illustrating emphasis of selected frequency components, according to the present invention.

Another method that may be used to help LLI subjects distinguish between phonemes is to emphasize selected frequency envelopes within a phoneme. Referring to FIG. 6, a graph 600 is shown illustrating a frequency envelope 602 whose envelope varies by approximately 27 hz. By detecting frequency modulated envelopes that vary from say 3–30 hz, similar to frequency variations in the consonant portion of phonemes, and selectively emphasizing those envelopes, they are made more easily detectable by LLI subjects. A 10 dB emphasis of the envelope 602 is shown in waveform 604, and a 20 dB emphasis in the waveform 606.

Figure 7:
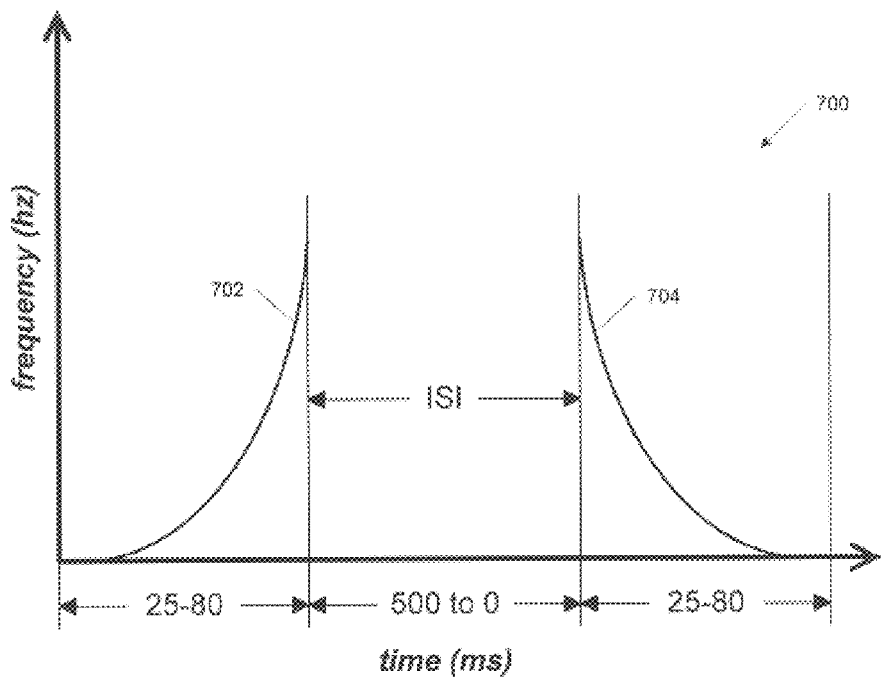
FIG. 7 is a chart illustrating up-down frequency sweeps of varying duration, separated by a selectable inter-stimulus-interval (ISI), according to the present invention.

A third method that may be used to train LLI subjects to distinguish short duration acoustic events is to provide frequency sweeps of varying duration, separated by a predetermined interval, as shown in FIG. 7. More specifically, an upward frequency sweep 702, and a downward frequency sweep 704 are shown, having duration's varying between 25 and 80 milliseconds, and separated by an inter-stimulus interval (ISI) of between 500 and 0 milliseconds. The duration and frequency of the sweeps, and the inter-stimulus interval between the sweeps are varied depending on the processing level of the LLI subject, as will be further described below.

Utilization of up-down frequency sweeps with varying ISI has been fully described in U.S. patent application Ser. No. 08/978,194, entitled "METHOD AND DEVICE FOR ENHANCING THE RECOGNITION OF SPEECH AMONG SPEECH-IMPAIRED INDIVIDUALS", and is hereby incorporated by reference.

Each of the above described methods have been combined in a unique fashion by the present invention to provide an adaptive training method and apparatus for training subjects having abnormal temporal processing abilities to recognize and distinguish short duration acoustic events that are common in speech. The present invention is embodied into a computer program entitled Fast ForWord by Scientific Learning Corporation. The computer program is provided to an LLI subject via a CD-ROM which is input into a general purpose computer such as that described above with reference to FIG. 1. In addition, a user may log onto a server, via an Internet connection, for example, to upload test results, and to download training parameters for future exercises. Specifics of the present invention will now be described with reference to FIGS. 8–30.

Figure 8:
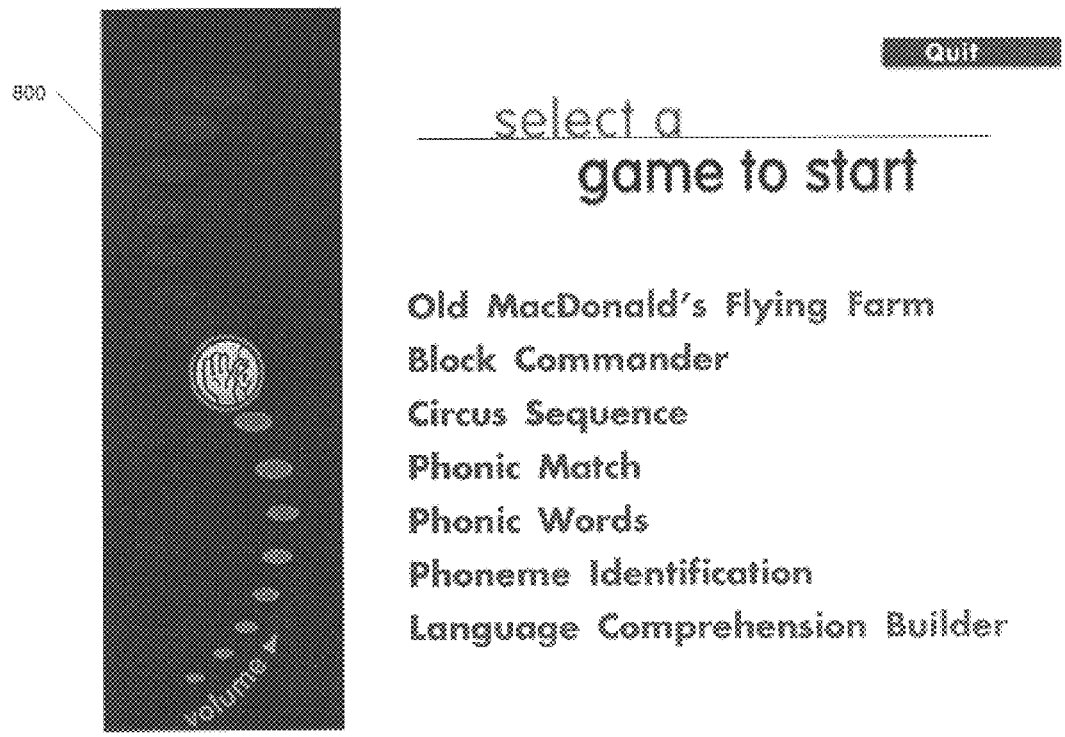
FIG. 8 is a pictorial representation of a game selection screen according to the present invention.

Referring first to FIG. 8, a pictorial representation is shown of a game selection screen 800. The game selection screen 800 is similar to that provided to an LLI subject upon initialization of the computer program according to the present invention. The game selection screen 800 includes the titles of seven computer games that provide distinct training exercises for improving speech recognition in subjects who abnormally process temporal acoustic events, and for building, or rebuilding the neurological connections necessary to accurately process phonemes at the rates common in speech. The game titles include: 1) Old MacDonald's Flying Farm; 2) Block Commander; 3) Circus Sequence; 4) Phonic Match; 5) Phonic Words; 6) Phoneme Identification; and 7) Language Comprehension Builder. Each of these games will be discussed in greater detail below.

When a subject begins execution of the Fast ForWord computer program, he/she is presented with a screen similar to the screen 800. More specifically, upon initiation of the program, the subject is presented with a screen that lists the subjects that are currently being trained by the program. The subject then selects his/her name from the list. Once the subject has selected his/her name, a screen similar to 800 appears, typically listing one of the seven programs, according to a training schedule that is dictated by the program, or is modified by an instructor. The order of the games, and the selection of which one of the seven games that is presented in the screen 800 varies from day to day. The subject then elects to play the first game listed according to the training schedule prescribed for the subject.

In one embodiment, a training schedule is provided by a certified Speech and Language Professional (SLP), and the SLP oversees each training session according to the schedule. An exemplary schedule requires a subject to cycle through five of the seven games for an hour and forty minutes, five days per week, for approximately six weeks. In addition, the schedule typically requires that a subject play Circus Sequence and Language Comprehension Builder everyday, alternating the other games so that they are played approximately the same amount of time.

In an alternative embodiment, the game schedule specified by an SLP at a remote server, and the daily parameters of the schedule are downloaded to the subject's computer, either daily or weekly. The schedule can be optimized over the course of the training program to first develop skills required for subsequent more advanced skills. It can also be used to help manage time in each game so that all of the games are completed at about the same time at the end of the training program. This embodiment allows a subject to obtain the benefits of the Fast ForWord program, and the oversight of a certified SLP, regardless of his/her geographic location. One skilled in the art will appreciate that the training schedule could either be provided in a window on the subject's computer, or could actually control the game selection screen to prompt the user only for those games required on a particular day.

Once a subject selects a particular game, he/she is taken into that particular game's module. Alternatively, once the subject selects his/her name from the list, the particular games may be presented, in a predefined order, without requiring the subject to first select the game. For ease of illustration, each of the seven games will be discussed, in the order represented in FIG. 8.

Figure 9:
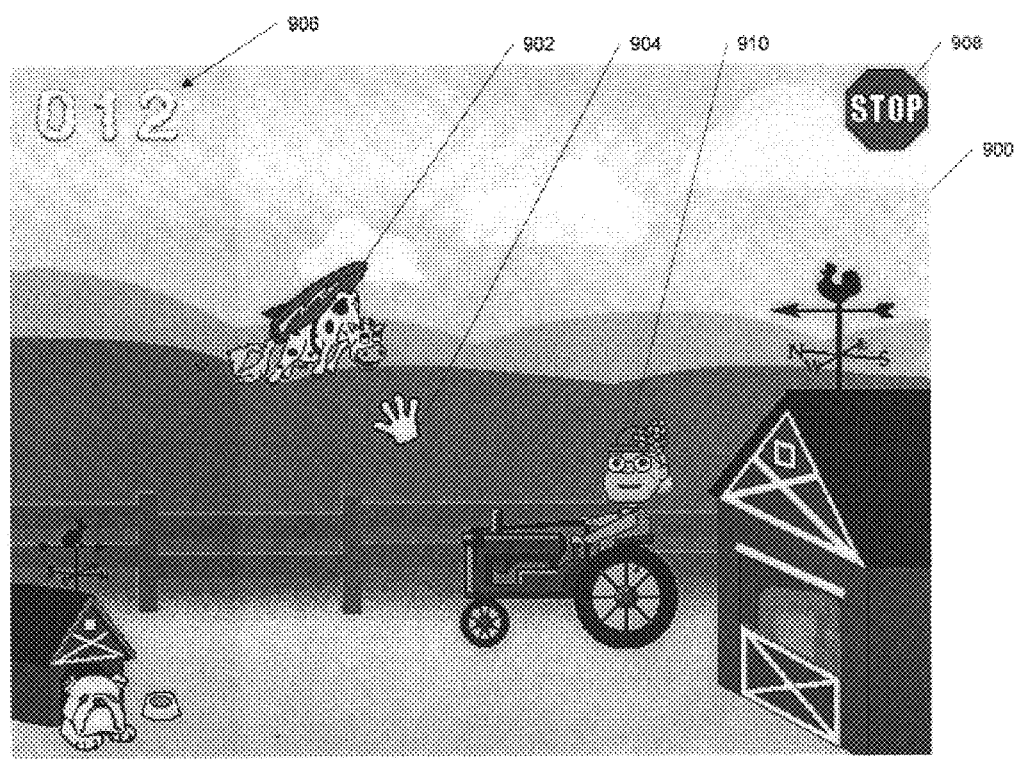
FIG. 9 is a pictorial representation of a game entitled "Old MacDonald's Flying Farm" according to the present invention.

Referring to FIG. 9, a scene 900 is shown for the first game in the program, Old MacDonald's Flying Farm (OMDFF). OMDFF uses a psychophysical procedure called limited-hold reaction time. A subject is asked to start a trial, in this case by grabbing a flying animal, at which point the game begins presenting a distractor phoneme that is modified in the time domain only. More specifically, information bearing acoustic elements whose temporal location within a phoneme carry important cues for phoneme identification are modified by stretching the acoustic elements in time, say to 150% of their normal duration. The acoustic elements that are stretched include voice onset time (VOT) between consonant and vowel events, as well as fricative-vowel gaps. The inter-stimulus interval (ISI) between presentations of the distractor phoneme is set initially to 500 ms. The distractor phoneme is repeated a random number of times, usually between 3 and 8 times, before the target tone is presented. The target phoneme has normal temporal acoustic parameters. The subject is asked to continue to hold the animal until the target phoneme is presented. When the subject hears the target phoneme, the subject is to release the animal. If the subject accurately hears the target phoneme and releases the animal within a desired "hit" window, then his/her score increases. If the subject misses the target phoneme, the animal flies away and no points are given. As the subject improves, the temporal parameters of the distractor phonemes are reduced in time to that of normal speech, and the ISI is reduced, systematically to 300 ms.

A number of scenes are provided in OMDFF, each correlated to a specific pair of sounds. The correlation of sound pairs to farm scenes is shown below:

| Sound Pair | Scene |
|---|---|
| /Gi/ - /Ki/ | Barn |
| /Chu/ - /Shu/ | Mudpit |

-continued

| Sound Pair | Scene |
|---|---|
| /Si/ - /Sti/ | Garden |
| /Ge/ - /Ke/ | House |
| /Do/ - /To/ | Coop |

So, when a subject grabs the flying animal, the game begins presenting a tone pattern such as: /Si/ . . . /Si/ . . . /Si/ . . . /Si/ . . . /Sti/. When the subject hears /Sti/, the subject is to release the animal.

The scene 900 provides a general farmyard background with three elements that persist across all the scenes. The elements are the score digits 906, the stop sign 908, and the tractor 910. The tractor 910 acts as a progress creature to graphically indicate to a subject their progress during a game. If the subject gets a correct response, the tractor 910 advances across the screen 900, from right to left. The score digits 906 display the subject's current score. The stop sign 908 is common to all seven games, and provides a subject with a means for exiting the game, and then the program.

Also shown on the screen 900 are a flying farm animal 902, and a selection hand 904. In this scene, the flying farm animal 902 is a cow with a rocket pack. Other scenes provide different farm animals propelled through the air with different flying apparatus. Operation of the game OMDFF will now be described with reference to FIG. 10.

Figure 10:
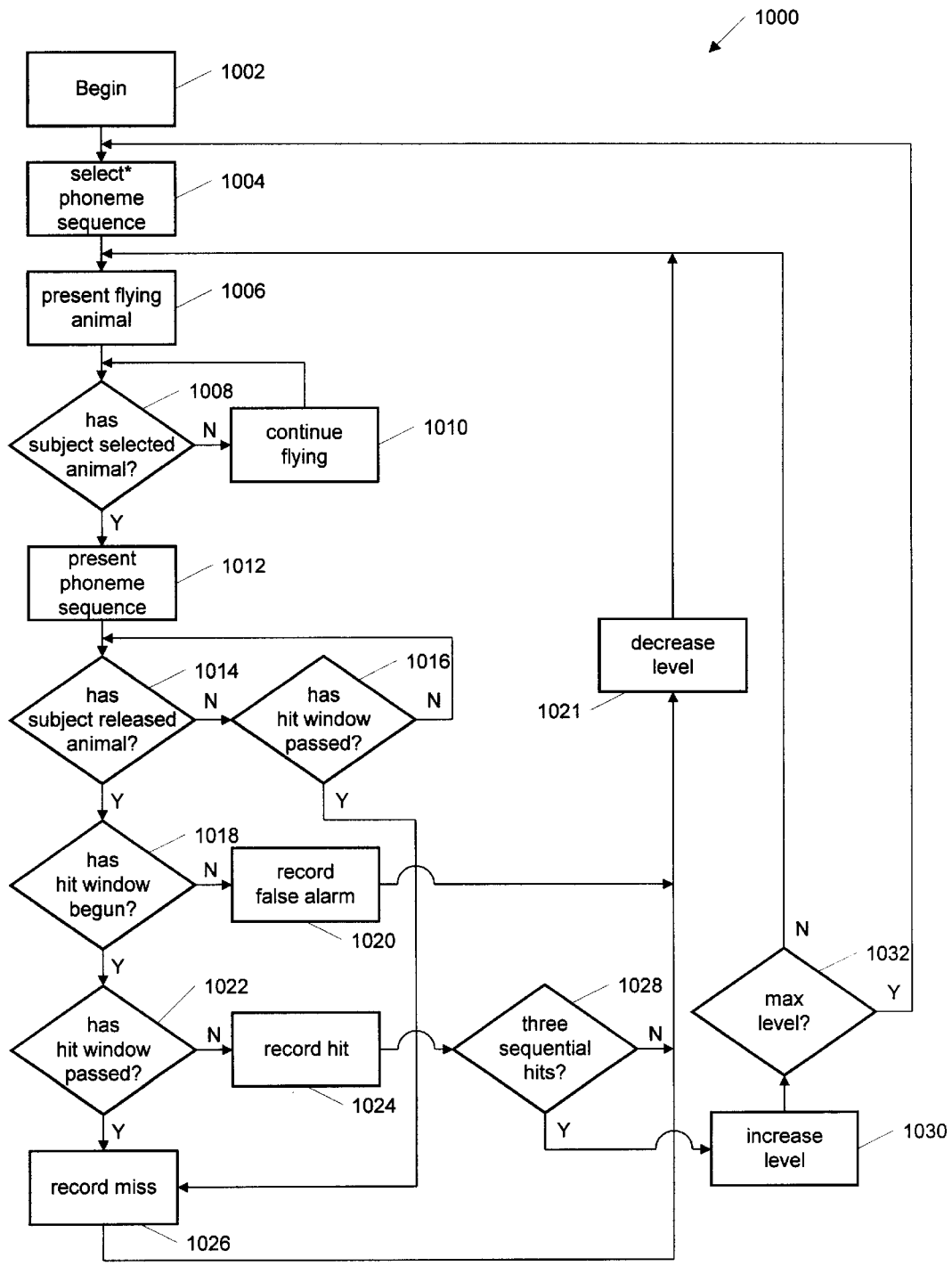
FIG. 10 is a flow chart illustrating the adaptive auditory training procedures embodied in the game Old MacDonald's Flying Farm.

In FIG. 10, a flow chart 1000 is provided that illustrates operation of the OMDFF game. The game begins at block 1002 and proceeds to block 1004.

At block 1004, the computer program selects a particular tone sequence to be played for a subject. For example, the program would select the tone pair /Si/ . . . /Sti/, stretched 150%, with an ISI of 500 ms. The tone pair that is selected, the stretching, and the ISI, are all associated with a particular skill level. And, the skill level that is presented to a subject is adapted in real time, based on the subjects ability to recognize the target phoneme, as will be further described below. However, the initial phoneme pair, stretching and ISI are chosen to allow an LLI subject to understand the game, and to begin to distinguish phonemes common in speech. Upon selection of a particular phoneme sequence, and skill level, flow proceeds to block 1006.

At block 1006, the game presents a flying animal 902. As mentioned above, the animal 902 that is presented varies according to which of the phoneme pairs are selected. If the animal 902 is a flying cow, the phoneme pair that will be presented is /Gi/ . . . /Ki/. The animal 902 continues to fly around the screen until the subject places the selection hand 904 over the animal 902, and holds down a selection button, such as a mouse button. After the animal 902 is presented, flow proceeds to decision block 1008.

At decision block 1008, a test is made as to whether the subject has selected the animal 902. If not, flow proceeds to block 1010 where the animal 902 continues to fly. The animal 902 will continue moving about the scene 900 until it is selected. Flow then proceeds to block 1012.

At block 1012, the program begins presenting the selected phoneme sequence. More specifically, an audio formatted file is called by the program that is to be played by a computer, either through speakers connected to the computer, or though headphones worn by a subject. In one embodiment, the file is a QuickTime audio file, configured according to the parameters necessary for the skill level of the user, i.e., phoneme pair, stretching, and ISI. In addition, a starting point in the file is chosen such that the distractor phoneme is presented a random number of times, between 3 and 8 times, before the target phoneme is presented. After the phoneme sequence begins playing, flow proceeds to decision block 1014.

At decision block 1014, a determination is made as to whether the subject has released the animal 902. If the subject has not released the animal 902, a parallel test is made, shown as decision block 1016.

Decision block 1016 tests whether a "hit" window has passed. More specifically, the program contains a lockout window of 200 ms that begins when the target phoneme is played. It is believed that if the subject releases the animal 902 within 200 ms of the target phoneme beginning play, it is merely coincidental that he/she would have heard the target phoneme. This is because no subject's reaction time is quick enough release the animal 902 so soon after hearing the target phoneme. The start of the "hit" window begins after the lockout window, i.e., 200 ms after the target phoneme begins. The end of the hit window is calculated as the start of the hit window, plus the length of one phoneme letter. So, at decision block 1016, if the hit windows has not passed, the computer continues to test whether the subject has released the animal 902. If the hit window has passed, and the subject has not released the animal 902, flow proceeds to block 1026.

At block 1026, a miss is recorded for that test. After recording the miss, flow proceeds back to block 1021.

At block 1021, the skill level for the selected phoneme sequence is decreased, as will be further described below. Flow then proceeds back to block 1006 where another flying animal is presented for the same phoneme sequence.

At decision block 1014, if it is determined that the subject has released the animal 902, instruction flow proceeds to decision block 1018.

At decision block 1018, a determination is made as to whether the hit window has begun. That is, did the subject release the animal 902 during or before the lockout period? If the hit window has not begun, instruction flow proceeds to block 1020.

Block 1020 records a false alarm and instruction flow proceeds to block 1021. It should be appreciated that a false alarm is recorded, rather than a miss, because it suggests that the subject detected a change in the phoneme sequence when a change has not yet occurred. If, at decision block 1018, the hit window has begun, flow proceeds to decision block 1022.

At decision block 1022 a determination is made as to whether the hit window has passed. If the hit window has passed, prior to the subject releasing the animal 902, then flow proceeds to block 1026 where a miss is recorded, as described above. However, if the hit window has not passed flow proceeds to block 1024.

At block 1024, a hit is recorded for the subject. That is, the subject has correctly heard the target phoneme, and has released the animal 902 in an appropriate time frame. Flow then proceeds to decision block 1028.

At decision block 1028, a determination is made as to whether the subject has heard the target phoneme, and released the animal 902 within the hit window, three times in a row. If not, then flow proceeds back to block 1006 where another animal 902 is presented. If the subject has responded correctly, three times in a row, flow proceeds to block 1030.

At block 1030, the skill level for the selected tone sequence is increased by one level. In one embodiment, 18 skill levels are provided for each phoneme sequence. As mentioned above, the skill levels begin temporal modifications of the phonemes, and by separating the presented phonemes with an ISI of 500 ms. As the subject's ability to distinguish between the distractor and target phonemes improves, the temporal modifications of the phoneme is reduced to that of normal speech, and the ISI is reduced to 300 ms. One skilled in the art will appreciate that the degree of phoneme temporal manipulation, from 150% to 100%, the variation of ISI among the skill levels, and the number of skill levels provided, may vary depending on the LLI subject and the type of training that is required. In one embodiment, after a subject successfully passes a phoneme sequence with 150% time modification, and an ISI of 500 ms, the next skill level presented holds the time modification at 150%, but reduces the ISI to 400 ms. Flow then proceeds to decision block 1032.

At decision block 1032 a determination is made as to whether the maximum level has been reached for the selected phoneme sequence. That is, has the subject progressed through all the skill levels to the point that they are correctly recognizing a target phoneme with a duration of 100%, and with an ISI of 0 ms? If not, then flow proceeds to block 1006 where the animal 902 is again presented to the subject, this time, at an increased skill level. However, if the subject has reached the maximum level for a particular phoneme sequence, flow proceeds to block 1004 where a phoneme tone sequence is selected. If a subject has not yet played the new phoneme sequence that is selected, the skill level is set to the easiest level. However, if the subject has previously heard the new phoneme sequence, the level of play begins, either at or below the last skill level obtained, typically 5 skill levels below what was last obtained.

Selection of phoneme sequences and skill levels are performed by the program to insure that a subject is exposed to each of the phoneme pairs, but spends the greater portion of his/her time with those pairs that are the most difficult to distinguish. In addition, the number of recorded hits/misses/false alarms and reaction times are recorded for each level, and for each phoneme pair, on a daily basis. The records are then uploaded to a remote server where they are either reviewed by a remote SLP, or are tabulated and provided to a local SLP. The SLP then has the option of controlling the selection of phoneme sequence selection, and/or skill level, according to the particular needs of the subject, or of allowing automatic selection to occur in a round robin manner.

While not shown, the program also keeps track of the number of correct responses within a sliding window. This is visually provided to a subject by advancing the tractor 910, from the right to the left, for each correct response. After 10 correct responses, creative animations are played, and bonus points are awarded, to reward the subject and to help sustain the subject's interest in the game. Of course, the type of animation presented, and the number of correct responses required to obtain an animation are variables that may be set by an SLP.

Figure 11:
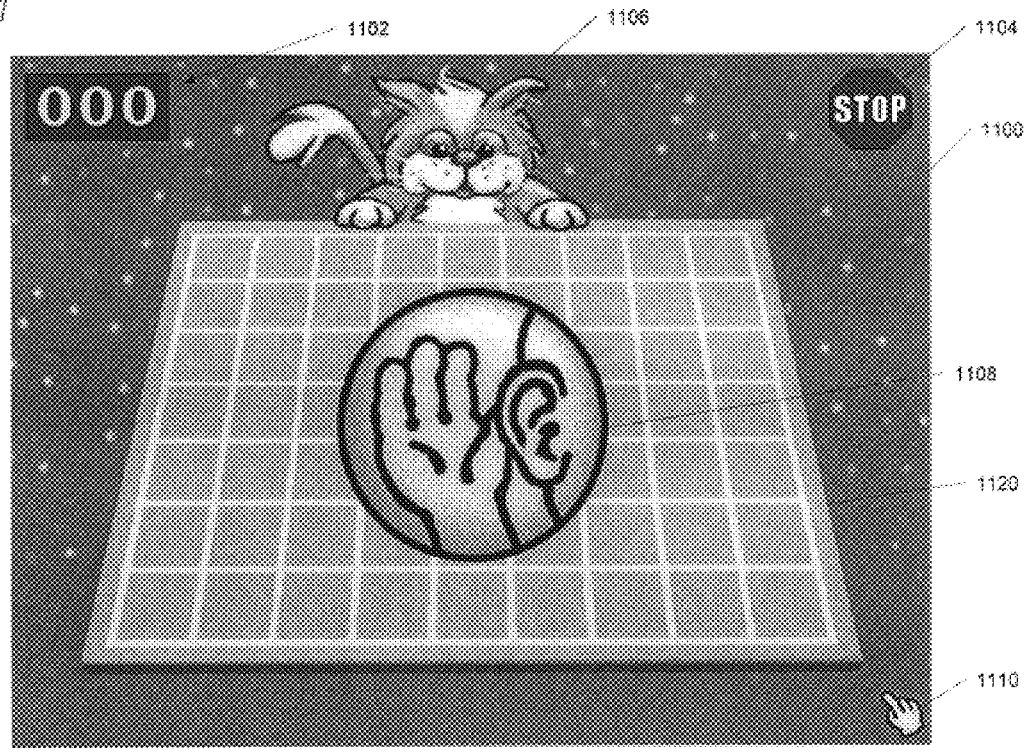
FIGS. 11 and 12 are pictorial representations of a game entitled "Block Commander" according to the present invention.

Now referring to FIG. 11 a screen 1100 is shown of the second game in the Fast ForWord program, entitled Block Commander. The Block Commander game presents a subject with audio prompts, directing the subject to perform an action. An exemplary action might be "point to the green circle." The types of prompts are grouped according to difficulty, requiring a subject to perform increasingly sophisticated tasks, depending on their skill level. If the subject responds correctly he/she is awarded a point. Otherwise, the cursor hand turns red and demonstrates how the command should have been performed. This feedback allows the subject to learn from the computer the more difficult manipulations that are required. In addition, the prompts are digitally processed by stretching the speech commands (in the time domain), and by emphasizing particular frequency envelopes in the speech, that contain time modulated acoustic components.

The screen 1100 contains a number score 1102 and a stop sign 1104. The number score 1102 provides visual feedback to a subject regarding their progress in the game, and the stop sign 1104 provides a selection mechanism for ending the game. Also shown is a cat 1106. The cat 1106 provides animations for a subject during training. A grid 1120 is shown, in a 55 degree perspective, upon which are placed 3D tokens, further described below. In the center of the grid 1120 is an ear/hand button 1108. When a subject places a hand selector 1110 on top of the ear/hand button 1108, and selects the icon (by pressing a mouse key), then a trial in the Block Commander game begins. This is shown in FIG. 12, to which attention is now directed.

Figure 12:
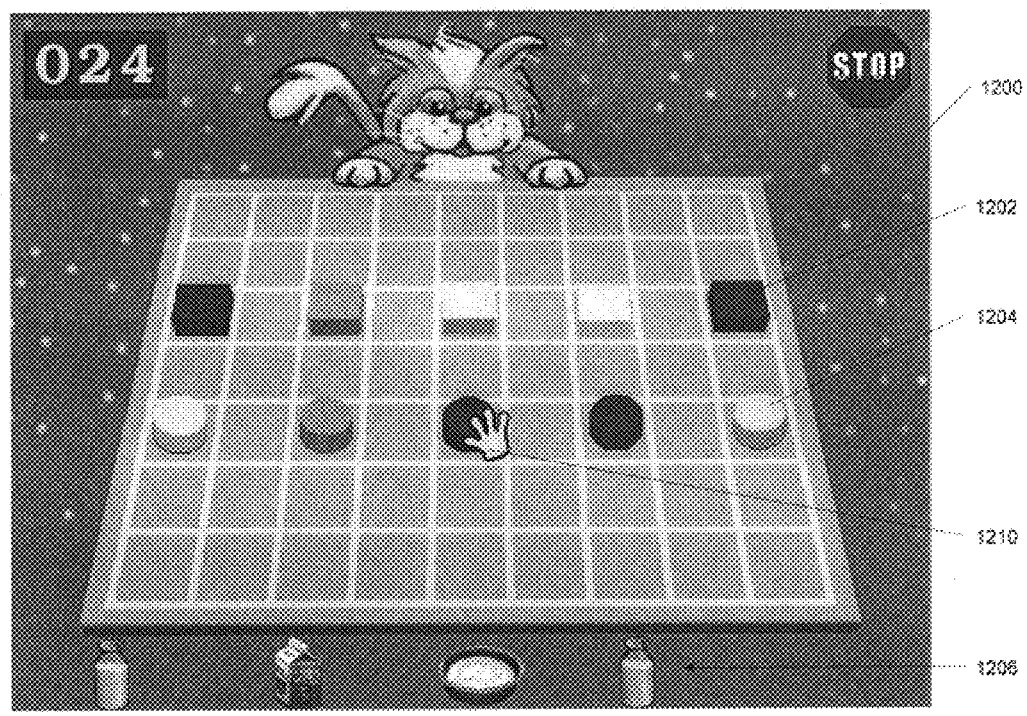

In FIG. 12, a screen shot 1200 is shown that includes the stop sign, number score, and grid, as shown above. In addition, a row of different colored squares 1202, and a row of different colored circles 1204 are provided. Use of the squares 1202 and the circles 1204 will be described below with reference to FIG. 13. Also shown are a number of progress tokens 1206 at the bottom of the screen 1200. The progress tokens 1206 indicate the number of correct answers within a particular instance of the game. In one embodiment, after 5 tokens 1206 are shown, indicating 5 correct responses, a reward animation and bonus points are provided to the user.

Figure 13:
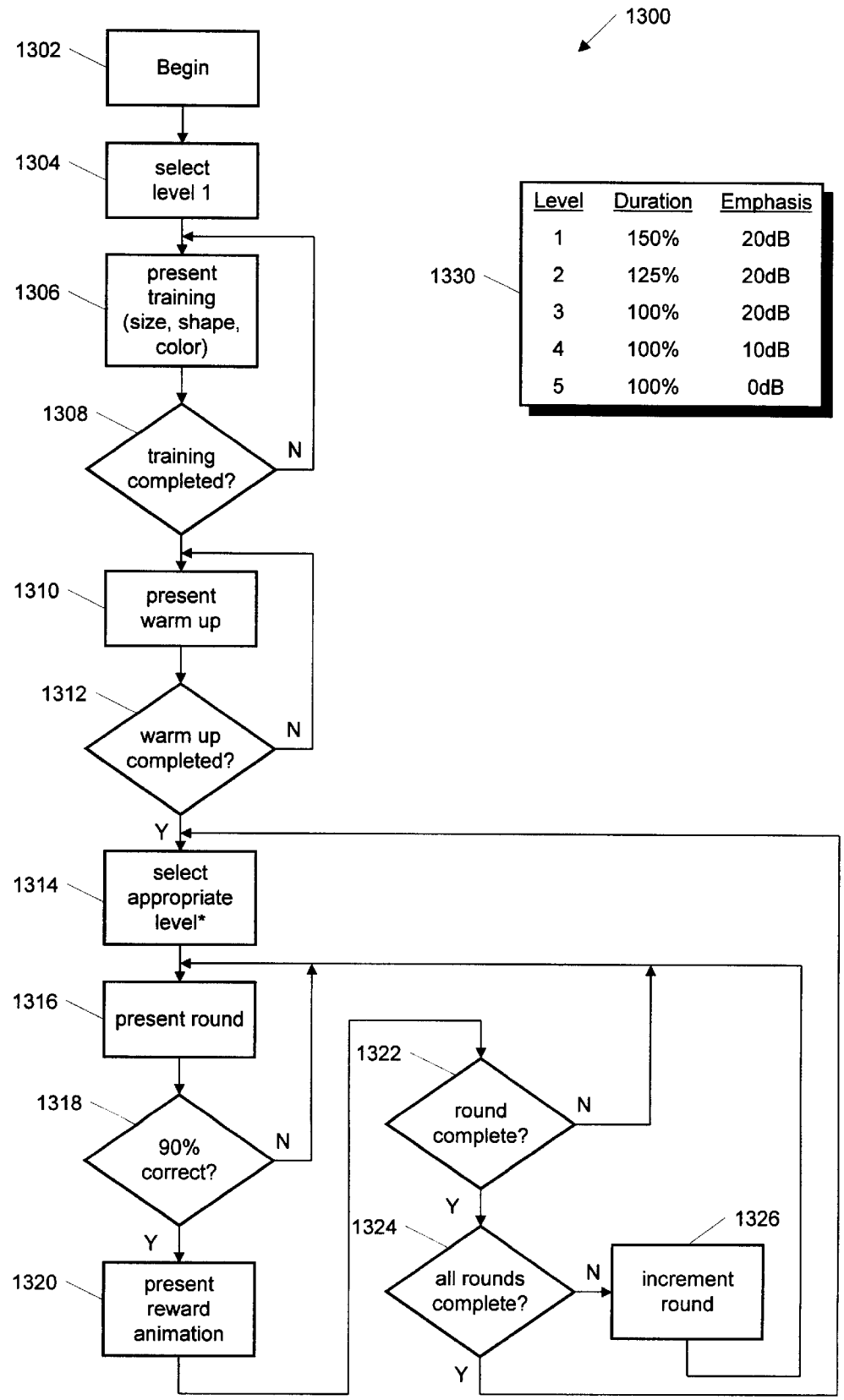
FIG. 13 is a flow chart illustrating the adaptive auditory training procedures embodied in the game Block Commander.

Now referring to FIG. 13, a flow chart 1300 is shown that illustrates operation of the Block Commander game. Execution begins at block 1302 and proceeds to block 1304.

At block 1304 the game selects the first playing level that is to be presented to a subject. To the right of block 1304 is a table 1330 that illustrates the 5 processing levels that are used in the Block Commander game. The levels are distinct from each other in terms of the amount of stretching (in the time domain) that is used on speech, and the amount of emphasis that is applied to selected frequency envelopes within the speech. Flow then proceeds to block 1306.

At block 1306, the game presents a program to a subject that trains the subject to play the game. The training portion consists of 3 rounds. The first round trains the subject to distinguish between object sizes, e.g., large and small. The second round trains the subject to distinguish between object shapes, e.g., square and circle. The third round trains the subject to distinguish between object colors, e.g., blue, red, yellow, green and white. More specifically, the prompts given to a subject during training are:

| | |
|---|---|
| Size Round 1 | Touch the large circle |
| | Touch the small circle |
| | Touch the large square |
| | Touch the small square |
| Shape round 2 | Touch the square |
| | Touch the circle |
| Color round 3 | Touch the blue square |
| | Touch the red square |
| | Touch the yellow square |
| | Touch the green square |
| | Touch the white square |

For a subject to pass any of the training rounds, and progress to the next training round, two correct hits are required for each command prompt, with no errors. If an error is made, the score is reset, and play for that round starts over. All of the prompts for the training rounds are at processing level 1, 150% duration and 20 dB emphasis. After a subject has completed the training program he/she will not see it again. Upon completion of the training program, flow proceeds to decision block 1308.

At decision block 1308 a determination is made as to whether the training has been completed. If not, then flow proceeds back to block 1306 where training continues. If training has been completed, flow proceeds to block 1310.

At block 1310, a warm up exercise is presented to a subject. The warm up exercise is presented each time a user plays the game, at the speech processing level that was last completed. The warm up round includes the following prompts:

| | |
|---|---|
| Warm up | Touch the green circle |
| | Touch the yellow square |
| | Touch the blue square |
| | Touch the white circle |
| | Touch the red circle |
| | Touch the blue circle |
| | Touch the green square |
| | Touch the yellow circle |
| | Touch the red square |
| | Touch the white square |

The ordering of the prompts is random each time the warm up is played. After presentation of each of the prompts flow proceeds to decision block 1312.

At decision block 1312, a determination is made as to whether the warm up round has been completed. If not, then flow proceeds back to block 1310 where the warm up continues. Otherwise, flow proceeds to block 1314.

At block 1314, an appropriate processing level is selected for a subject. The first time a subject plays the Block Commander game, processing level 1 is selected. However, after the subject has progressed beyond processing level 1, the level selected will be the level that the subject last played. Flow then proceeds to block 1316.

At block 1316, the first round of the game is presented to a subject. As mentioned above, in one embodiment of the Block Commander game, six rounds are provided. The rounds are as follows:

| | |
|---|---|
| Round 1 | Touch the green circle |
| | Touch the yellow square |
| | Touch the blue square |
| | Touch the white circle |
| | Touch the red circle |
| | Touch the blue circle |
| | Touch the green square |
| | Touch the yellow circle |
| | Touch the red square |
| | Touch the yellow square |
| Round 2 | Touch the small green circle |
| | Touch the large red circle |
| | Touch the large white circle |
| | Touch the large red square |
| | Touch the small yellow circle |
| | Touch the large green circle |
| | Touch the large green square |
| | Touch the small white circle |
| | Touch the small blue square |
| | Touch the large green circle |
| Round 3 | Touch the white circle and the blue square |
| | Touch the blue square and the red circle |
| | Touch the red square and the green |

|  | |
|---|---|
| | circle |
| | Touch the green square and the blue square |
| | Touch the yellow circle and the red circle |
| | Touch the red square and the green square |
| | Touch the red square and the yellow circle |
| | Touch the white square and the red circle |
| | Touch the green circle and the green square |
| | Touch the blue square and the yellow circle |
| Round 4 | Touch the small green circle and the large yellow square |
| | Touch the small red square and the small yellow circle |
| | Touch the large green square and the large blue circle |
| | Touch the large red square and the large blue square |
| | Touch the small red square and the small green circle |
| | Touch the small white circle and the small green circle |
| | Touch the large red square and the large white square |
| | Touch the large green circle and the large red circle |
| | Touch the small blue square and the small white circle |
| | Touch the small yellow square and the large blue square |
| Round 5 | Put the blue circle on the red square |
| | Put the green square behind the white circle |
| | Touch the green circle with the blue square |
| | Touch-with the green circle-the blue square |
| | Touch the green circle and the blue square |
| | Touch the green circle or the blue square |
| | Put the white square away from the yellow square |
| | Put the yellow square in front of the red square |
| | Touch the squares, except the yellow one |
| Round 6 | Put the white square beside the red circle |
| | Put the blue circle between the yellow square and the white square |
| | Except for the blue one, touch the circles |
| | Touch the red circle-No!-the green square |
| | Instead of the yellow square, touch the white circle |
| | Together with the yellow circle, touch the green circle |
| | After touching the yellow square, touch the blue circle |
| | Put the red circle underneath the yellow square |
| | Before touching the white circle, touch the blue square |

Each of the prompts are presented to the user in random order, but successful completion of each of the prompts in a round is required before a round is considered complete. After a first prompt is provided to a subject, flow proceeds decision block 1318.

At decision block 1318, a determination is made as to whether there have been 90% correct responses in a sliding group of 5 items. If not, then flow proceeds back to block 1316 where another prompt in a round is provided. If there have been 90% correct responses, as will be illustrated by 5 progress tokens at the bottom of the screen, then flow proceeds to block 1320.

At block 1320, the subject is shown a reward animation. In one embodiment, the animation consists of characters morphing out of the blocks on the board. Flow then proceeds to decision block 1322.

At decision block 1322, a determination is made as to whether the round is complete. A round is complete when a subject successfully responds to all of the prompts in the round. If the round is not complete, flow proceeds back to block 1316 where another prompt is provided to the subject. If the round is complete, flow proceeds to decision block 1324.

At decision block 1324, a determination is made as to whether all six rounds within the game have been completed. If not, then flow proceeds to block 1326 where the round level is incremented. Flow then proceeds back to block 1316 where prompts for the new round are presented. If decision block 1324 determines that all rounds have been completed, flow proceeds back to block 1314 where an appropriate skill level is selected. In one embodiment, if a subject successfully completes all six rounds, at skill level 1 (150% duration, 20 dB emphasis), he/she will progress to skill level 2 (125% duration, 20 dB emphasis).

The Block Commander program begins by providing a subject with a number of simple commands, stretched in time, with particular emphasis given to phoneme components that are difficult for an LLI subject to understand. As the subject correctly responds to the simple commands, the commands increase in difficulty. Once the subject masters the more difficult commands, the amount of stretching, and the amount of emphasis is reduced, and the process is repeated. The rounds continue, over the course of days and weeks, until the subject is correctly responding to the difficult commands at skill level 5, which is normal speech.

One skilled in the art will appreciate that the commands cause the subject, not only to understand the phonemes that are presented, but also to apply logical reasoning to the more difficult commands, and to recall the constructs of the commands. The requirement that the subject recall the command constructs is directed at improving the subjects memory, as well as to improving their ability to process acoustic events. It is believed that the games repetitive nature, that trains the subject's neurological connections to process speech, is also helpful in improving the subject's memory, and his/her cognitive skills in understanding linguistic relationships.

Figure 14:
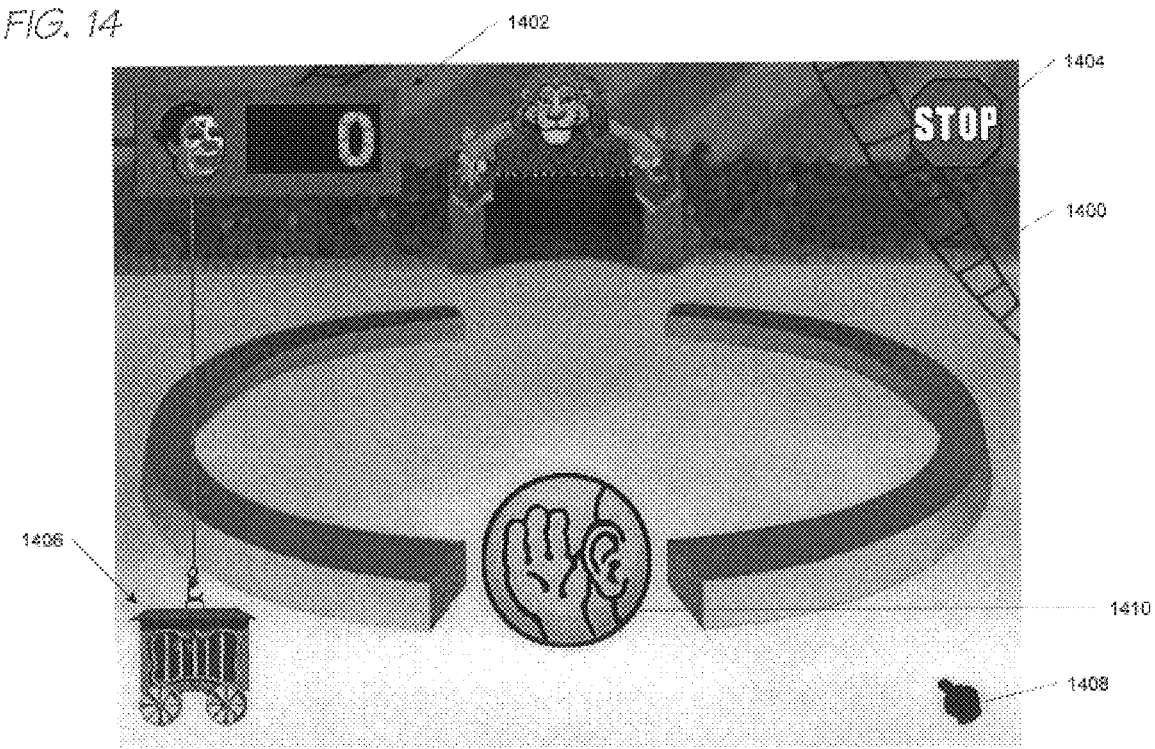
FIGS. 14 and 15 are pictorial representations of a game entitled "Circus Sequence" according to the present invention.

Now referring to FIG. 14, a screen shot 1400 is shown for the third game in the Fast ForWord program, entitled Circus Sequence. The Circus Sequence game trains a subject to distinguish between upward and downward frequency sweeps that are common in the stop consonant portion of phonemes, by varying the duration and frequency of the sweeps, and by varying the inter-stimulus interval (ISI) between presentation of the sweeps.

The screen 1400 contains a number score 1402, a stop sign 1404, and a progress element 1406, all within a circus ring environment. In addition, the screen 1400 contains a hand selector 1408, and an ear/hand button 1410. As in the Block Commander game, a user begins a test by selecting the ear/hand button 1410 with the hand selector 1408.

Figure 15:
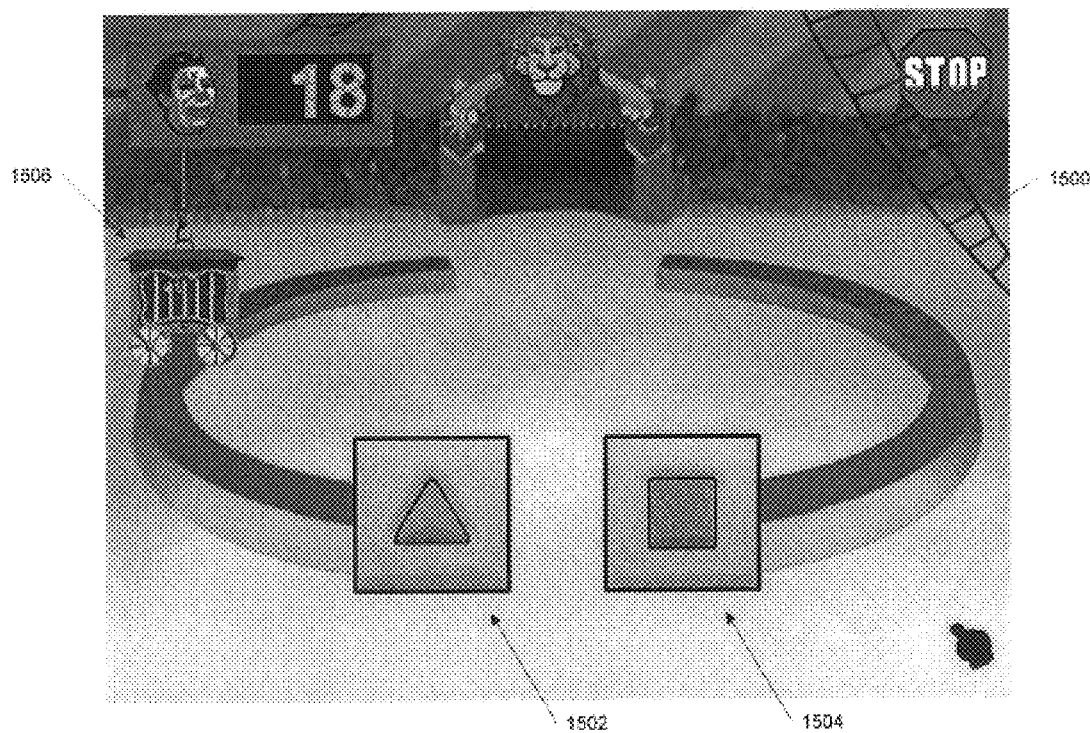

Referring to FIG. 15, a screen shot 1500 is shown that illustrates two elements 1502, 1504 that are presented to a subject after the ear/hand button 1410 is selected. The left element 1502 pertains to an upward frequency sweep, and the right element 1504 pertains to a downward frequency sweep. In addition, a progress element 1506 is shown elevated above the circus ring floor, to indicate that a subject has correctly responded to a number of tests. Game play will now be illustrated with reference to FIG. 16.

Figure 16:
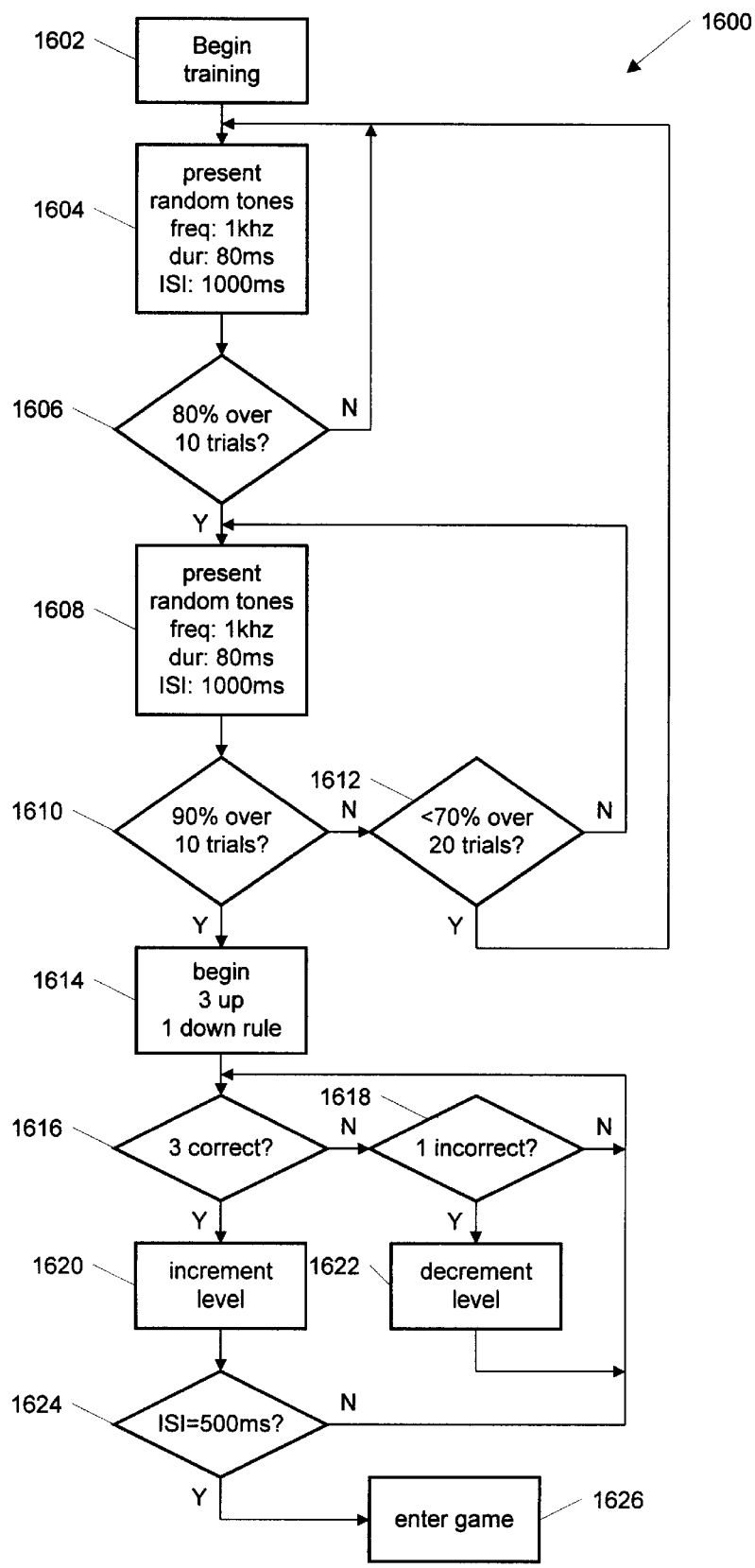
FIG. 16 is a flow chart illustrating the initial training procedures embodied in the game Circus Sequence.

FIG. 16 provides a flow chart 1600 that illustrates program flow through the training portion of the Circus Sequence Game. Training begins at block 1602 and proceeds to block 1604.

At block 1604, the program begins presenting a random sequence of frequency sweeps to a subject. All sweep sequences are of the form: up-up; up-down; down-up; or down-down. Thus, if the program presents the sweep sequence "up-up", a subject is to click on the left element 1502 twice. If the program presents a sweep sequence "down-up", the subject is to click on the right element 1504, then on the left element 1502. So, once the program provides a sweep sequence to the subject, the subject selects the elements corresponding to the frequency modulated (FM) tone sequence. If the subject is correct, he/she is awarded points, the progress element 1506 advances upwards, and the ear/hand button 1410 is presented, allowing the subject to begin another test. During training, all upward sweeps are presented starting at 1 kHz and all downward sweeps ending at 1 kHz, with upward/downward sweeps at 16 octaves per second. The duration of the sweeps are 80 ms, and the sweeps are separated by 1000 ms. Research has shown that most LLI subjects are capable of distinguishing between frequency sweeps of this duration, and having an ISI of 1000 ms. After each sweep sequence is presented, flow proceeds to decision block 1606.

At decision block 1606, a determination is made as to whether the subject has correctly responded to 80% of the trials over a sliding scale of the last ten trials. If not, then flow proceeds back to block 1604 where the sequences continue to be presented. If the subject has correctly responded 80% of the time, flow proceeds to block 1608.

At block 1608, random sequences are again presented, at 1 khz, having a duration of 80 ms and an ISI of 1000 ms. Flow then proceeds to decision block 1610.

At decision block 1610, a determination is made as to whether the subject has correctly responded to 90% of the trials over a sliding scale of the last ten trials. If not, then flow proceeds to decision block 1612. If the subject has correctly responded to 90% of the trials over a sliding scale of the last ten trials, flow proceeds to block 1614.

At decision block 1612, a determination is made as to whether a subject has correctly responded to less than 70% of the trials, over a sliding scale of the last 20 trials. If not, indicating that he/she is responding correctly between 70–90% of the time, then flow proceeds back to block 1608 where the sweep sequences continue to be presented. If a determination is made that the subject is correctly responding less than 70% of the time over the last 20 trials, then flow proceeds back to block 1604, where the training begins again.

At block 1614, a 3-up, 1-down rule begins. This rule allows a subject to advance in difficulty level every time 3 correct responses are provided, while reducing the level of difficulty any time an incorrect response is given. Research has shown that a 3-up, 1-down rule allows a subject to obtain a correct response rate of approximately 80% near threshold, which is desired to motivate and encourage the subject to continue. A reduced accuracy rate discourages a subject, a situation that is not desired especially if the subject is an LLI child. Once the 3-up, 1-down rule is started, flow proceeds to decision block 1616.

At decision block 1616, a determination is made as to whether a subject has responded correctly the last 3 tests. If so, then flow proceeds to block 1620. If not, then flow proceeds to decision block 1618.

At decision block 1618, a determination is made as to whether a subject has incorrectly responded to the last test. If not, then flow proceeds back to decision block 1616 where another test is provided. However, if the subject has incorrectly responded to the last test, the difficulty level is reduced one level, and flow proceeds back to decision block 1616 where another test is presented. During the training level, all tests are performed at 80 ms duration, with 1000 ms ISI, which is the easiest skill level. Therefore, if the subject incorrectly responds at that level, no change in difficulty is made.

At block 1620, the skill level is increased. During training, the sweep sequences are presented at 1 khz, with 80 ms duration, but the ISI is reduced between the sweeps each time the level is incremented. In one embodiment, the ISI levels start at 1000 ms, and proceed through 900 ms, 800 ms, 700 ms, 600 ms and 500 ms. Flow then proceeds to decision block 1624.

At decision block 1624, a determination is made as to whether the ISI is at 500 ms. If not, then flow proceeds back to decision block 1616 where sweep sequences continue to be presented. If the ISI is 500 ms, the training session ends and the subject is allowed to enter the real game, at block 1626.

Figure 17:
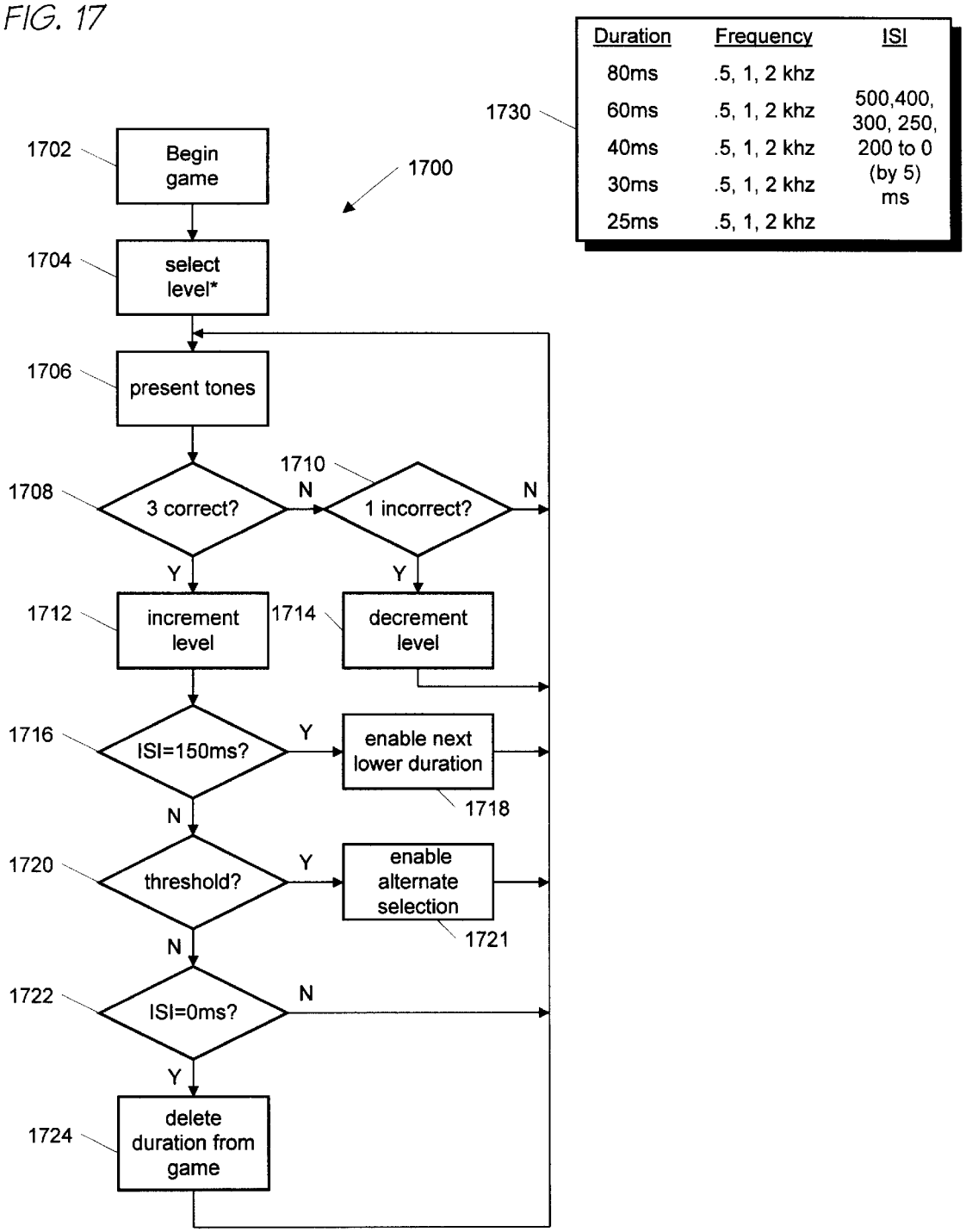
FIG. 17 is a flow chart illustrating the adaptive auditory training procedures embodied in the game Circus Sequence.

Referring now to FIG. 17, a flow chart 1700 is provided that illustrates operation of the Circus Sequence game, after the training session has been completed. The game begins at block 1702 and proceeds to block 1704.

At block 1704, an appropriate skill level is selected. The skill levels used by Circus Sequence are shown in table 1730. For each of three frequencies: 500 hz, 1 khz, and 2 khz, a number of skill levels are provided. The skill levels begin by presenting frequency sweeps having a duration of 80 ms, and an ISI between the sweeps of 500 ms. As a subject advances, the ISI is reduced, either to 0 ms, or in one embodiment, to 125 ms. It should be appreciated that the ISI increments used should be selected to slowly train a subject's ability to distinguish between similar phonemes, such as /ba/ and /da/, while not frustrating the subject by training beyond levels required to distinguish between such phonemes.

When a subject first plays Circus Sequence, after passing training, he/she is provided with frequency sweeps beginning at 1 khz, having 80 ms duration and an ISI of 500 ms. On subsequent days, the frequency that is selected is random, and can be either 500 hz, 1 khz or 2 khz. Once the appropriate skill level has been selected, flow proceeds to block 1706.

At block 1706, a tone sequence is presented, according to the selected skill level. Flow then proceeds to decision block 1708.

At decision block 1708, a determination is made as to whether the subject has correctly responded to the last 3 trials. If not, then flow proceeds to decision block 1710. If the subject has correctly responded to the last 3 trials, flow proceeds to block 1712.

At decision block 1710, a determination is made as to whether the subject has incorrectly responded to the last trial. If not, then flow proceeds back to block 1706 where another tone sequence is presented. If the subject incorrectly responded to the last trial, flow proceeds to block 1714.

At block 1714, the skill level is decremented. If the skill level has an ISI of 500 ms, no decrease is made. However, if the skill level has an ISI that is less than 500 ms, the difficulty is reduced 1 level. For example, if the subject incorrectly responds to a trial having an ISI of 180 ms, for example, the difficulty level will be reduced, so that the next tone sequence will have an ISI of 185 ms. Flow then proceeds back to block 1706 where another tone sequence is presented.

At block 1712, if the user has correctly responded to the last 3 trials, the skill level is incremented. For example, if a subject is at a skill level with a sweep duration of 80 ms and an ISI of 250 ms, the skill level will increase such that the ISI for the next tone sequence will be 200 ms. Flow then proceeds to decision block 1716.

At decision block 1716, a determination is made as to whether the ISI is at 150 ms. If not, then flow proceeds to decision block 1720. If the ISI is at 150 ms, flow proceeds to block 1718.

At block 1718, the next lower duration is enabled. This allows the program to simultaneously trial a subject with multiple sweep durations, once the subject is successfully responding at an ISI level of 150 ms. For example, if a subject is correctly responding to tone sequences of duration 80 ms, with an ISI of 150 ms, then testing continues at 80 ms. In addition, testing is begun with sweep sequences of duration 60 ms, at an ISI of 500 ms. Flow then proceeds to back to block 1706 where another tone sequence is presented. This allows the program to present tone sequences of different duration, and different ISI, while tracking progress for each duration/ISI combination.

At decision block 1720, a determination is made as to whether the subject has reached a training threshold. In one embodiment, a training threshold is reached when the subject has had eight skill level reversals within six skill levels of each other. If such a threshold is reached, flow proceeds to block 1721. Otherwise, flow proceeds to decision block 1722.

At block 1721, the program moves the subject to the next frequency category to be tested. It is believed that once a threshold has been met on a particular day, the subject should not continue being tested at the same frequency. Thus, the program allows a subject to progress, either to an ISI of 0 ms (or some other minimal ISI) or to a threshold at one frequency, and then begin testing at an alternative frequency. Flow then proceeds back to block 1706.

At decision block 1722, a determination is made as to whether the ISI for a particular tone duration is 0 ms. If not, then flow proceeds back to block 1706 where another sweep sequence is presented. However, if a subject has reached a skill level of 0 ms ISI for a particular duration, flow proceeds to block 1724.

At block 1724, the program deletes the duration associated with the 0 ms ISI from the trial. This is because testing at that level is no longer required by the subject due to their proficiency. However, as mentioned above, an alternative embodiment may select an ISI of greater than 0 ms as the point where the duration is deleted from the game. Flow then proceeds back to block 1706 where more tone sequences are presented.

While not shown, in one embodiment, a threshold level is provided that causes the game to begin testing a subject at an alternate frequency. For example, if the subject is testing at 500 hz, and a threshold is reached, the program will begin testing the subject at 2 khz. The threshold is reached when a subject has 8 skill level reversals within 6 levels of each other. When this occurs, the program ceases testing at the frequency for which the threshold was reached, and begins testing at an alternative frequency.

Also, when a subject begins each day of testing, a frequency different than that tested the previous day is begun. Moreover, a skill level that is 5 less than completed the previous day is chosen, presuming the subject completed at least 20 trials for that frequency.

As mentioned above, each correct response causes the progress element 1506 to advance upward. After ten correct responses, a reward animation is provided to entertain the subject. When the animation ends, the subject is prompted with the ear/hand button 1410 to begin another trial.

Now referring to FIG. 18, a screen shot 1800 of the fourth game in Fast Forward, Phonic Match, is provided. The screen 1800 includes a set of pictures 1802, a progress creature 1804, a stop sign 1806, and a number score 1808. The progress creature 1804, stop sign 1806 and number score 1808 function similarly to those described in previous games.

The set of pictures 1802 are arranged into a 2×2 grid. When a subject selects any of the pictures, a word or phoneme is played. On any grid, there are two pictures that play the same word. Thus, for a 2×2 grid, there are two words that will be presented. The test for the subject is to distinguish between similar words, to recall which picture is associated with which word, and to sequentially select two pictures that present the same word. Similar words are presented together, with the words processed according to the processing levels shown in table 1902 of FIG. 19.

Initially, subjects are presented words at processing level 1, with a duration of 150%, and having 20 dB emphasis of selected frequency envelopes within the words. In addition, different skill levels, as shown in table 1904, are provided that increase the grid size for a particular trial, and set the maximum number of clicks, or selections, that a subject can attempt before losing the trial. Operation of the game is illustrated in FIG. 20. However, before providing a detailed description of game operation, the words used in the game are shown.

| | |
|---|---|
| Word Group 1 | big, bit, dig, dip, kick, kid, kit, pick, pig, pit, tick, tip |
| Word Group 2 | buck, bud, but, cup, cut duck, dug, pub, pup, tub, tuck, tug |
| Word Group 3 | back, bag, bat, cab, cap, cat, gap, pack, pat, tack, tag, tap |
| Word Group 4 | ba, cha, da, ga, ka, la, pa, ra, sa, sha, ta, za |

Referring now to FIG. 20, the Phonic Match game begins at block 2002, and proceeds to block 2004.

At block 2004, a 2×2 grid is presented. The words associated with the 2×2 grid are selected from one of the four Word Groups shown above. The selection of the Word Group is random, except that tracking of previously played Word Groups is done to insure that all Word Groups are equally represented, and that a subject is not provided the same Word Group as played on an immediately preceding day. The words within a Word Group are typically selected according to their acoustic similarity.

The subject is required to sequentially select two pictures that have the same word associated with them. When a subject sequentially selects two pictures associated with the same word, the pictures are removed from the gird being played. After a subject completes a 2×2 grid, whether correctly or incorrectly, flow proceeds to decision block 2006.

At decision block 2006, a determination is made as to whether the subject has successfully passed three 2×2 grids.

Referring to table 1904 of FIG. 19, ten skill levels are shown. When a 2×2 grid is first presented, the skill level entered is level 8. Skill level 8 defines a 2×2 grid, with a maximum number of allowed clicks as 8. If a subject selects pictures on a 2×2 grid more than 8 times, the grid is not considered passed, and game flow proceeds back to block 2004 where another grid is presented. If not, then flow proceeds back to block 2004 where another 2×2 grid is presented with words from the same Word Group. If the subject has successfully passed three 2×2 grids, thus progressing from level 8 through level 10, flow proceeds to block 2008.

At block 2008, a new grid is presented for a particular Word Group, or stimulus set. Initially, a 3×3 grid is provided, at skill level 2. The maximum number of clicks allowed for a subject to pass a 3×3 grid is 20. Within a 3×3 grid, 1 of the pictures is a wildcard, since there are an odd number of pictures. Selection of the wildcard simply removes the picture from the grid, and does not count against the subject as a selection, or click. After a 3×3 grid is presented to a subject, flow proceeds to decision block 2010.

At decision block 2010, a determination is made as to whether the subject passed the level. That is, did the subject properly distinguish between word pairs, and sequentially select picture pairs associated with words in 20 or less clicks. If so, then flow proceeds to block 2012. If not, then flow proceeds to block 2014.

At block 2012, the skill level is incremented. For example, if a subject was at level 2, he/she will increment to level 3. Note: levels 2–3 present a 3×3 grid with a maximum number of clicks of 20, while levels 4–7 present a 4×4 grid with a maximum number of clicks of 60. Once the skill level is incremented, flow proceeds to block 2020.

At block 2020, a grid according to the new skill level is presented. The grid is associated with the same Word Group that was previously used, but possibly with different words from the group. Flow then proceeds to decision block 2022.

At decision block 2022, a determination is made as to whether the subject has passed the level. That is, did the subject correctly associate the word pairs in less than or equal to the number of allowed clicks. If not, flow proceeds to block 2014. If the subject passed the level, flow proceeds to decision block 2024.

At decision block 2024, a determination is made as to whether the subject has reached skill level 7. Level 7 is termed the "decision" level. If the skill level that has just been passed is not level 7, then flow proceeds back to block 2012 where the skill level is incremented. However, if the skill level passed is level 7, flow proceeds to decision block 2026.

At decision block 2026, a determination is made as to whether all four stimulus sets, or Word Groups have been passed. If not, then flow proceeds to block 2018. However, if a subject has correctly passed skill level 7, for all four Word Groups, flow proceeds to block 2028.

At block 2028, the next processing level is selected. Referring to table 1902 of FIG. 19, a subject begins at processing level 1 (duration 150%, emphasis 20 dB). Once all four Word Groups have been passed at skill level 7, the amount of audio processing to the words is reduced. First, the duration of the words is reduced, from 150%, to 125%, to 100%, and then the amount of emphasis applied to selected frequency components is reduced, from 20 dB, to 10 dB, to 0 dB. Once a subject has reached processing level 5, he/she is presented with normal speech. After the next processing level is selected, flow proceeds to decision block 2030.

At decision block 2030, a determination is made as to whether all processing levels have been completed. That is, has the subject reached processing level 5. If not, flow proceeds back to block 2004 where the game begins anew, with a 2×2 grid, but at the new processing level. However, if the subject has reached processing level 5, flow proceeds to block 2032.

At block 2032, a 5×5 grid is provided, with a maximum number of allowable clicks as 90. From this point forward, the game continues playing indefinitely, but the decision round, level 7, switches from a 4×4 grid to a 5×5 grid.

Referring back to decision block 2022, if a subject does not pass a particular level, flow proceeds to block 2014.

At block 2014, the skill level is decremented. Flow then proceeds to decision block 2016.

At decision block 2016, a determination is made as to whether the new skill level is less than level 1. Level 1 is considered a "slip" level indicating that if a user failed at this level, a new Word Group should be provided. If the skill level is not less than 1, flow proceeds back to block 2020 where a new grid is presented, according to the present level. If the new level is less than 1, that is, if the subject failed to pass a grid, at skill level 1, flow proceeds to block 2018.

At block 2018, the program discontinues presenting words from the present Word Group, and changes the Word Group used for the grids. Flow then proceeds back to block 2008 where a 3×3 grid is presented, at skill level 2, using words from the new Word Group.

The flow chart 2000 demonstrates that a subject is required to proceed from level 2 through level 7 for each of the four Word Groups, at a particular processing level, before he/she is allowed to advance to the next processing level. The progress creature descends with each click. If the creature reaches the bottom, then the grid is not passed. If all picture pairs are matched prior to the creature reaching the bottom, extra points are awarded, a reward animation is presented and the grid is considered passed. When a subject has correctly selected a predetermined number of picture pairs, the progress animal 1804 reaches the top, and the subject is rewarded by an animation.

Figure 21:
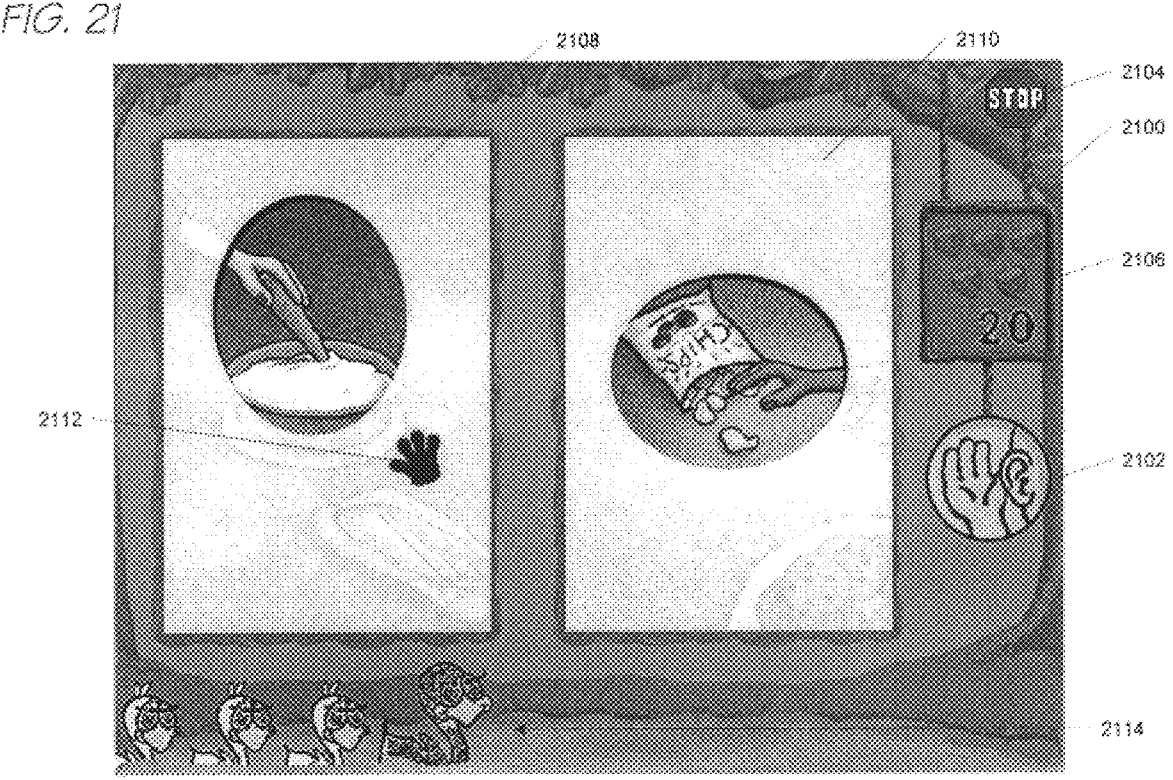
FIGS. 21 and 22 are pictorial representations of a game entitled "Phonic Words" according to the present invention.

Referring now to FIG. 21, a screen shot 2100 is shown illustrating the fifth game in the Fast Forward program, entitled Phonic Words. Phonic Words presents a subject with a sentence prompt that requires the subject to distinguish between two similar words, to accurately select one of two pictures 2108, 2110, using a selection hand 2112. The table below provides a list of the word pairs used. The first word in the pair is always the correct answer, but its representational image could appear on the left or right of the screen 2100.

base-face, face-base, vase-base, base-vase, face-vase, vase-face, bee-me, me-bee, knee-bee, bee-knee, knee-me, me-knee, breathe-breeze, breeze-breathe, day-they, they-day, lawn-yawn, yawn-lawn, ache-lake, lake-ache, ache-rake, rake-ache, ache-wake, wake-ache, lake-rake, rake-lake, lake-wake, wake-lake, rake-wake, wake-rake, sink-think, think-sink, chip-dip, dip-chip, sip-zip, zip-sip, chip-sip, sip-chip, chip-zip, zip-chip, dip-sip, sip-dip, dip-zip, zip-dip, pack-shack, shack-pack, tack-shack, shack-tack, pack-tack, tack-pack, tack-tag, tag-tack, rung-young, young-rung, rung-run, run-rung, young-run, run-young, pat-path, path-pat, bear-bell, bell-bear, thumb-tongue, tongue-thumb, comb-cone, cone-comb, mouse-mouth, mouth-mouse, cash-catch, catch-cash, fan-fang, fang-fan, sauce-saws, saws-sauce, bass-bath, bath-bass, cheese-chief, chiefcheese, foam-phone, phone-foam, fuzz-fudge, fudge-fuzz, safe-shave, shave-safe, long-lawn, lawn-long, piece-peas, peas-piece, piece-peach, peach-piece, peas-peach, peach-peas, wash-watch, watch-wash.

As before, the screen 2100 contains an ear/hand button 2102 for beginning a trial, a stop sign 2104 for ending the game, and a number score 2106. Within the number score 2106 are five acorns, indicating the processing level currently being tested. Also shown are progress creatures 2114 indicating a number of correct responses. As a subject correctly responds to the game, a new progress creature 2114 is added. When the number of progress creatures 2114 reaches ten, a reward animation is provided and bonus points are awarded.

Figure 22:
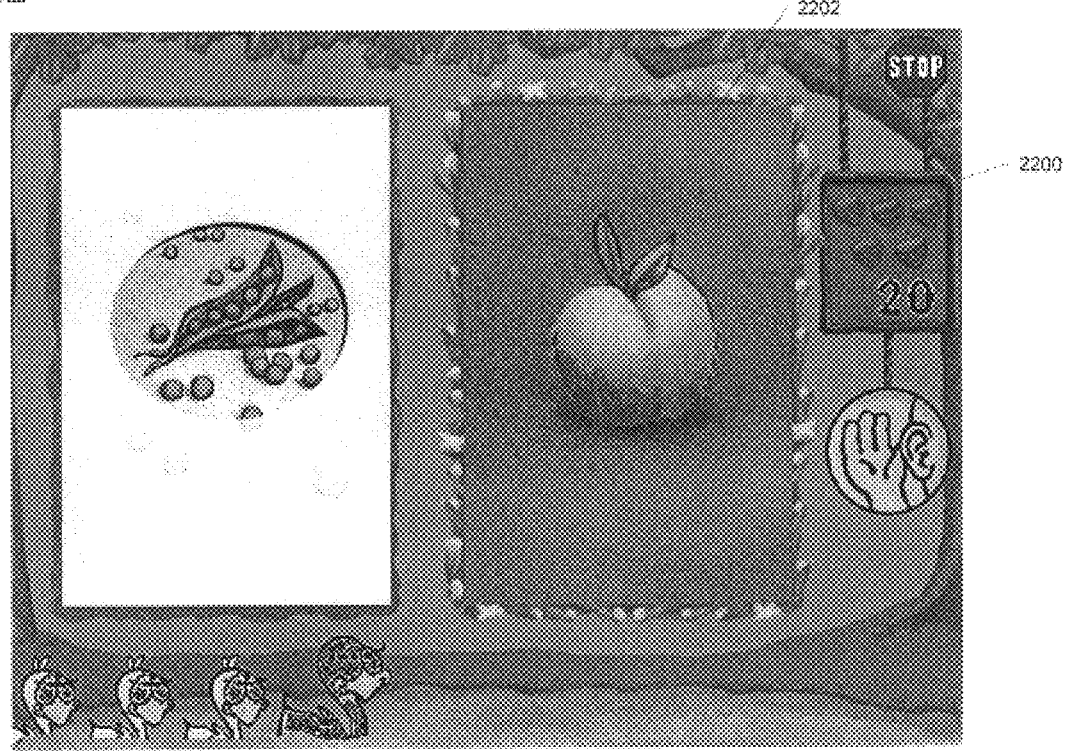

Referring to FIG. 22, a screen shot 2200 is shown where the word pair peach-peas is being tested. After a subject listens to a prompt containing the target word, he/she selects one of the two pictures. The subject, whether correct or incorrect, will then be shown the correct selection, in this case peach, by having the mask removed from the picture frame 2202.

Figure 23:
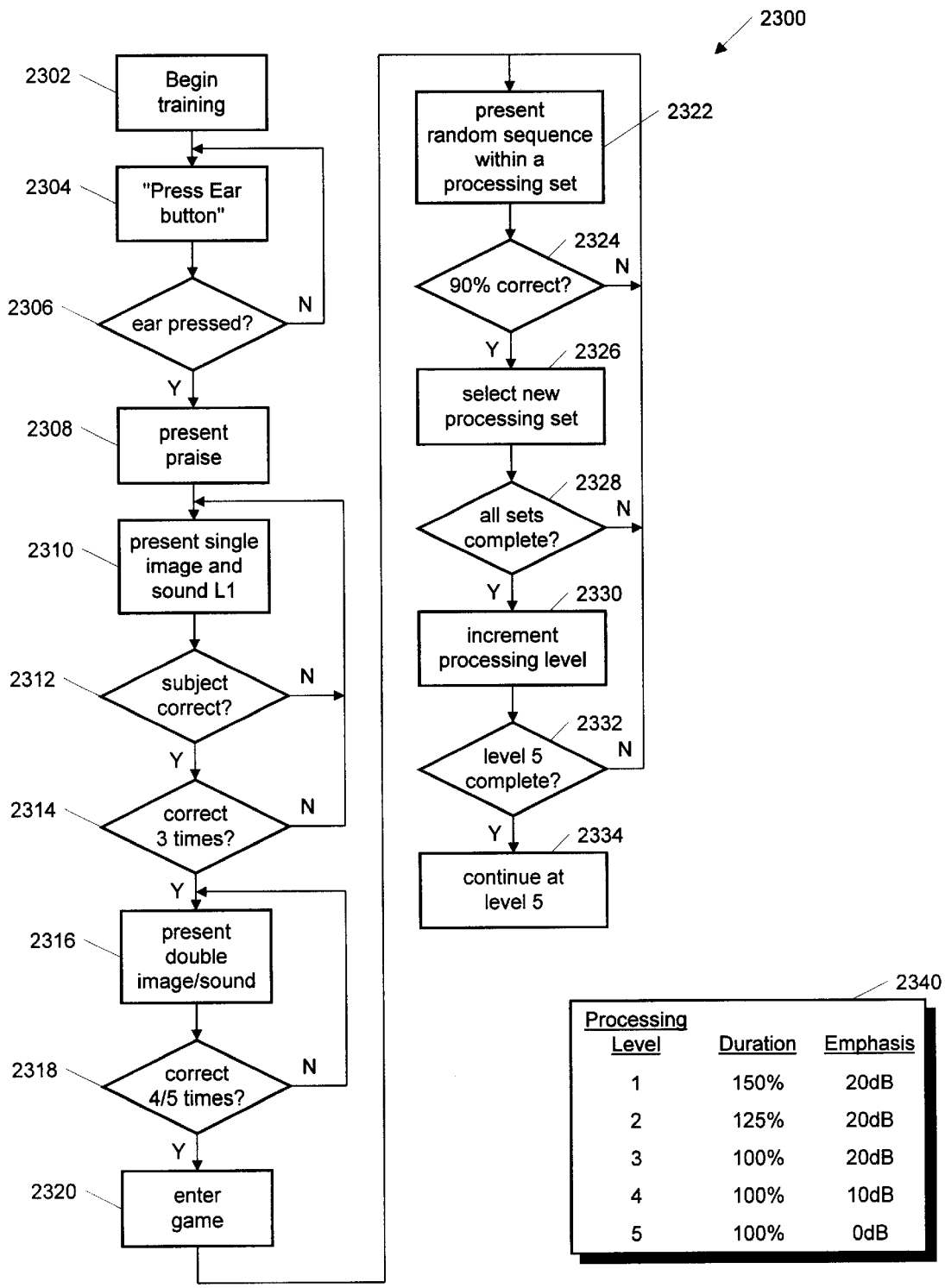
FIG. 23 is a flow chart illustrating the adaptive auditory training process embodied in the game Phonic Words.

Referring now to FIG. 23, operation of the Phonic Words game is illustrated by flowchart 2300. Please note that five processing levels, similar to those used above in Phonic Match and Block Commander, are shown in table 2340. The game begins at block 2302 and proceeds to training block 2304.

At training block 2304 the subject is prompted to "press the ear button". The prompting is processed at level 1 (duration 150%, emphasis 20 dB). Flow then proceeds to decision block 2306.

At decision block 2306, a determination is made as to whether the ear/hand button 2102 has been pressed. If not, then flow proceeds back to block 2304 where the prompting is repeated. If the ear/hand button 2102 has been pressed, flow proceeds to block 2308.

At block 2308, praise is played for the subject. Flow then proceeds to block 2310.

At block 2310, a single image appears in one of the two frames 2108, 2110, and a sound file pertaining to the image is played for the subject. Flow then proceeds to decision block 2312.

At decision block 2312, a determination is made as to whether the subject has selected the appropriate image. The image continues to be displayed until the subject selects the image. Flow then proceeds to decision block 2314.

At decision block 2314, a determination is made as to whether the subject has correctly selected the single image, three times. If not, then flow proceeds back to block 2310 where another image is presented, with its associated word. If the subject correctly selects an image/word combination three times, flow proceeds to block 2316.

At block 2316, a pair of images are presented, along with a command prompt containing a word associated with one of the images. The other image presented is termed the distractor image. The user must click on the correct image 4 out of 5 times in a sliding scale to start the game. After the double image is presented, flow proceeds to decision block 2318.

At decision block 2318, a determination is made as to whether the subject has correctly selected an image, from the image pair, in 4 out of 5 cases, on a sliding scale. If not, then flow proceeds back to block 2316 where another image pair is presented. Otherwise, flow proceeds to block 2320 where the subject enters the game. Flow then proceeds to block 2322.

At block 2322, a subject is presented a sequence of image pairs, with associated words selected from a particular processing set. The processing sets are chosen by grouping words having similar phoneme characteristics. Once all of the words have been presented within a processing set, flow proceeds to decision block 2324.

At decision block 2324, a determination is made as to whether the subject has correctly understood a word, and properly selected its associated picture from the picture pair with 90% or greater accuracy. If not, flow proceeds back to block 2322 where random selection of image/word pairs continue, until a 90% success rate is achieved. Flow then proceeds to block 2326.

At block 2326, a new processing set is selected. Flow then proceeds to decision block 2328.

At decision block 2328, a determination is made as to whether all of the processing sets have been completed. If not, then flow proceeds back to block 2322 where random selection of image/word pairs are presented from the current processing set. However, if all of the processing sets have been completed, flow proceeds to block 2330.

At block 2330, the processing level is incremented. Initially, the processing level is level 1. After a subject has completed all of the processing sets, with a 90% or greater accuracy for each of the sets, the processing level is increased to level 2. As described above, the duration of the words is decreased first, from 150%, to 125% to 100%, and then the emphasis of selected frequency envelopes is reduced, from 20 dB, to 10 dB, to 0dB, until normal speech (level 5) is obtained. After the processing level is incremented, flow proceeds to decision block 2332.

At decision block 2332, a determination is made as to whether a subject has completed all of the sets at processing level 5. If not, then flow proceeds back to block 2322 where random selection of image/word pairs within a set are presented at the new processing level. However, if the subject has completed all of the processing sets at level 5, flow proceeds to block 2334.

At block 2334, Phonic Words continues to drill the subject randomly selecting image/word pairs within a processing set, at level 5.

Figure 24:
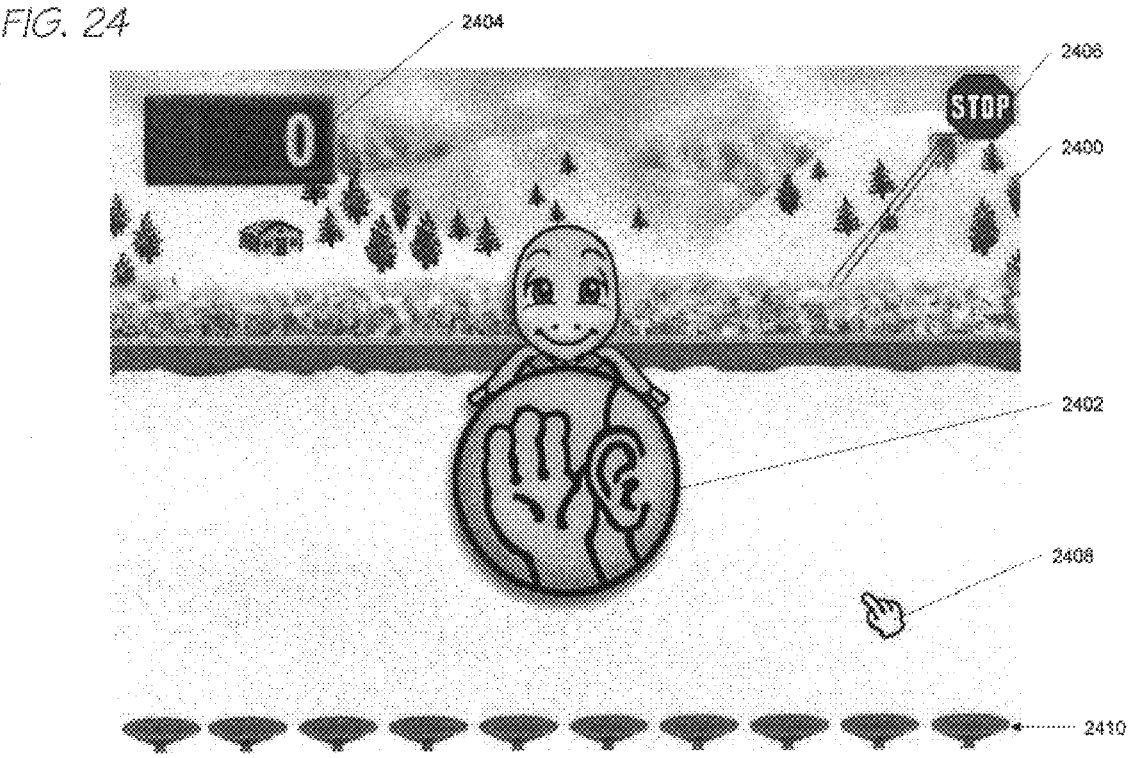
FIGS. 24 and 25 are pictorial representations of a game entitled "Phoneme Identification" according to the present invention.

Now referring to FIG. 24, a screen shot 2400 is provided for the sixth game in the Fast ForWord program, entitled Phoneme Identification. Phoneme Identification processes a number of phoneme pairs by selectively manipulating parameters such as consonant duration, consonant emphasis, and inter-stimulus interval. More specifically, five phoneme pairs are tested, each pair containing a target sound and a distractor. These include: 1) aba-ada; 2) ba-da; 3) be-de; 4) bi-di; and 5) va-fa.

For each phoneme pair, 26 different skill levels are provided, each level differing from the other in the degree of processing applied (duration and emphasis), and in the separation (ISI) of the distractor and target phoneme. Skill level 1 processes the phoneme pair by stretching the consonant portion 150% while leaving the vowel portion untouched, emphasizing selected frequency envelopes in the consonant portion 20 dB, and separating the distractor and target phonemes by 500 ms, for example. Skill level 26 provides a phoneme pair without stretching or emphasis, and with an ISI of 0 ms. Skill levels 2–25 progress towards normal speech by applying less and less consonant processing, with less and less separation between the distractor and target phonemes.

The screen 2400 contains an ear/hand button 2402 to allow a subject to begin a trial, a number score 2404 for tracking correct responses, a stop sign 2406 for exiting the game, a hand selector 2408, and progress elements 2410 for graphically illustrating progress to a subject. When the game is initially selected, five different animals are shown on the screen, each pertaining to a phoneme pair to be tested. A subject may select any one of the five animals to begin the game. After a subject has played the game with one of the five animals, the choice is reduced to four animals, and so on.

Figure 25:
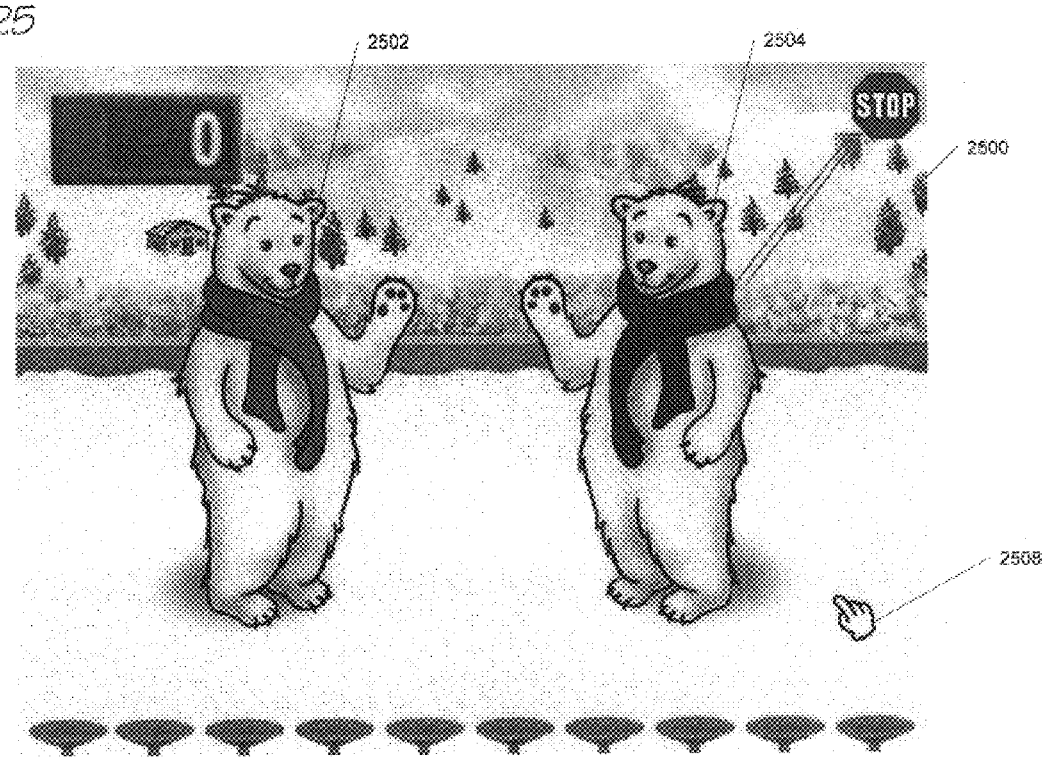

Referring to FIG. 25, a screen shot 2500 is shown with two polar bears 2502, 2504. In one embodiment, the polar bears 2502, 2504 are associated with the phoneme pair ba-da. There are five background scenes, each associated with an animal/phoneme pair, each having their own animations, etc. When a subject presses the ear/hand button 2402, the game plays a target phoneme, either ba or da. The phoneme pair is then presented by the polar bears 2502, 2504 with one bear speaking the distractor and the other bear speaking the target sound. A subject is required to distinguish between the distractor and target phonemes, and to select with the hand selector 2508, the polar bear that spoke the target phoneme. Details of how the game Phoneme Identification is played will now be provided with reference to FIGS. 26 and 27.

Figure 26:
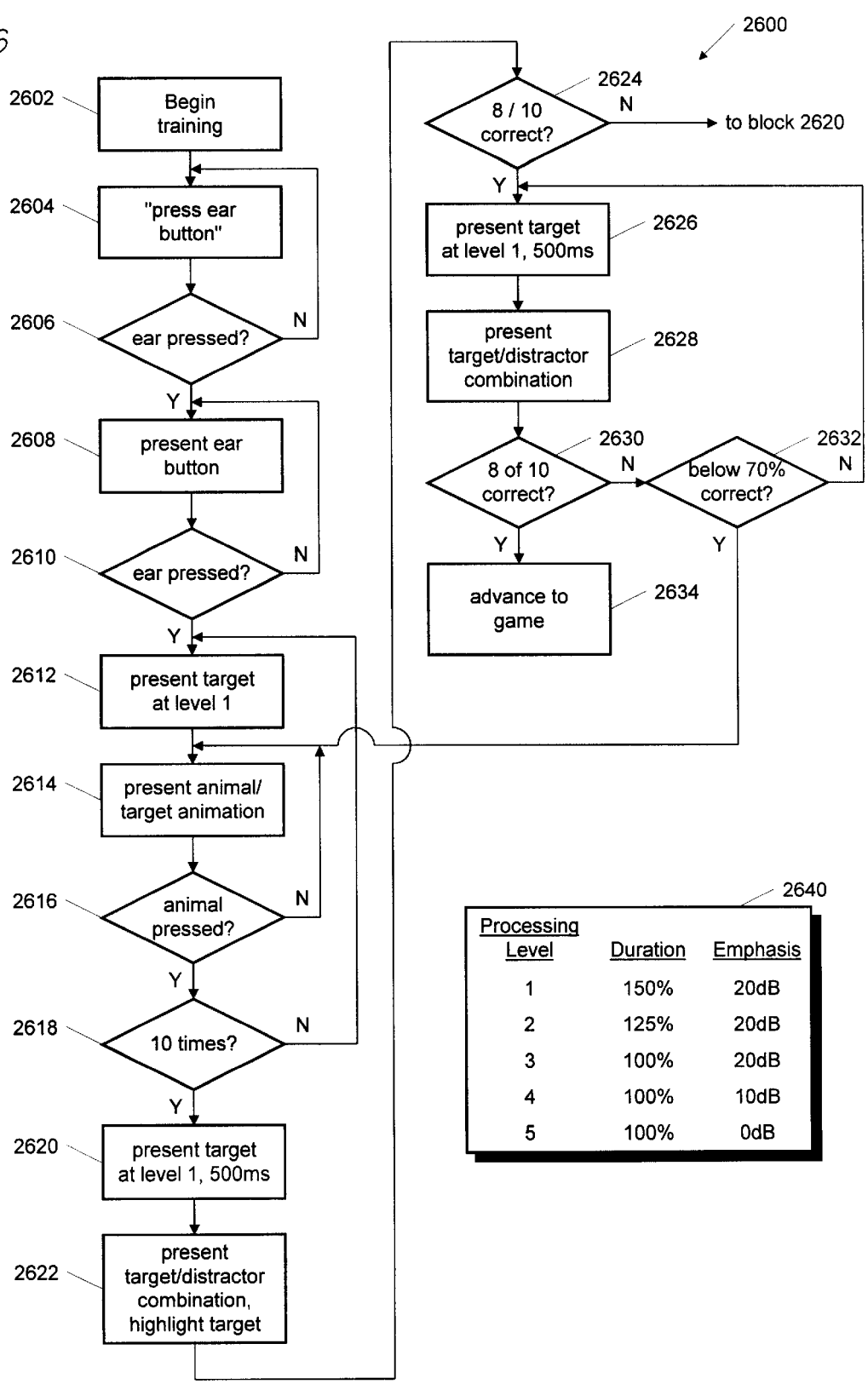
FIG. 26 is a flow chart illustrating the initial training procedures embodied in the game Phoneme Identification.

Referring to FIG. 26, a flow chart 2600 is shown that illustrates the training module of the Phoneme Identification game. Training begins at block 2602 and proceeds to block 2604.

At block 2604, the game presents the screen shot 2400, and prompts a subject to "press the ear button". Flow then proceeds to decision block 2606.

At decision block 2606, a determination is made as to whether the subject has pressed the ear/hand button 2402. If not, then flow proceeds back to block 2604 where the prompt is repeated, after a predetermined interval. If the subject has pressed the ear/hand button 2402, flow proceeds to block 2608.

At block 2608, the ear/hand button 2402 is presented, but this time without an audio prompt. Flow then proceeds to decision block 2610.

At decision block 2610, a determination is made as to whether the subject has pressed the ear/hand button 2402. If not, then flow proceeds back to block 2608. The subject remains in this loop until the ear/hand button 2402 is pressed. Once the ear/hand button 2402 is pressed, flow proceeds to block 2612.

At block 2612, a target phoneme, pertaining to a selected animal pair, is played for a subject. The target phoneme is processed at level 1, 150% duration, with 20 dB emphasis, as shown by the table 2640. Flow then proceeds to block 2614.

At block 2614, a single animal is presented that speaks the target phoneme. Flow then proceeds to decision block 2616.

At decision block 2616, a determination is made as to whether the animal that spoke the target phoneme has been selected. If not, flow proceeds back to block 2614 where the animal again speaks the target phoneme, after a predetermined interval. However, if the subject has selected the animal, flow proceeds to decision block 2618.

At decision block 2618, a determination is made as to whether the subject has correctly pressed the animal in ten trials. If not, then flow proceeds back to block 2612 where another trial is begun. However, once the subject has correctly responded in ten trials, flow proceeds to block 2620.

At block 2620, a target phoneme is again presented, at level 1 processing. Flow then proceeds to block 2622.

At block 2622, two animals are now presented, one speaking the target phoneme, the other speaking the distractor phoneme. The order of speaking the target and distractor phonemes is random, with the animal on the left speaking first, and the animal on the right speaking last. However, in this training level, the animal that speaks the target phoneme is visually highlighted for the subject. Both the target and distractor phonemes are processed at level 1, and are separated in time by 500 ms. Flow then proceeds to decision block 2624.

At decision block 2624, a determination is made as to whether the subject has correctly selected the animal speaking the target phoneme in 8 out of 10 trials, on a sliding scale. If not, then flow proceeds back to block 2620 where another trial is begun. If the subject has correctly responded in 8 out of 10 trials, flow proceeds to block 2626.

At block 2626, a target phoneme is presented to a subject, processed at level 1. Flow then proceeds to block 2628.

At block 2628, two animals are shown presenting a target phoneme and a distractor phoneme, both processed at level 1, with an ISI of 500 ms. The order of target/distractor phonemes is random. For this trial, however, the animal speaking the target phoneme is not visually highlighted for the subject. Flow then proceeds to decision block 2630.

At decision block 2630, a determination is made as to whether the subject has correctly responded to 8 out of 10 trials, on a sliding scale. If so, then the subject has successfully completed the training and flow proceeds to block 2634, allowing the subject to advance to the game. However, if the subject has not been successful in 8 out of 10 trials, then flow proceeds to decision block 2632.

At decision block 2632, a determination is made as to whether the subject has responded correctly less than 70% of the time in at least 10 trials. If not, then flow proceeds back to block 2626 where another trial is presented. If the subject has less than a 70% success rate, over at least 10 trials, then flow proceeds back to block 2614 where trials begin again, but where visual highlighting of the animal speaking the target phoneme is provided for the subject.

Figure 27:
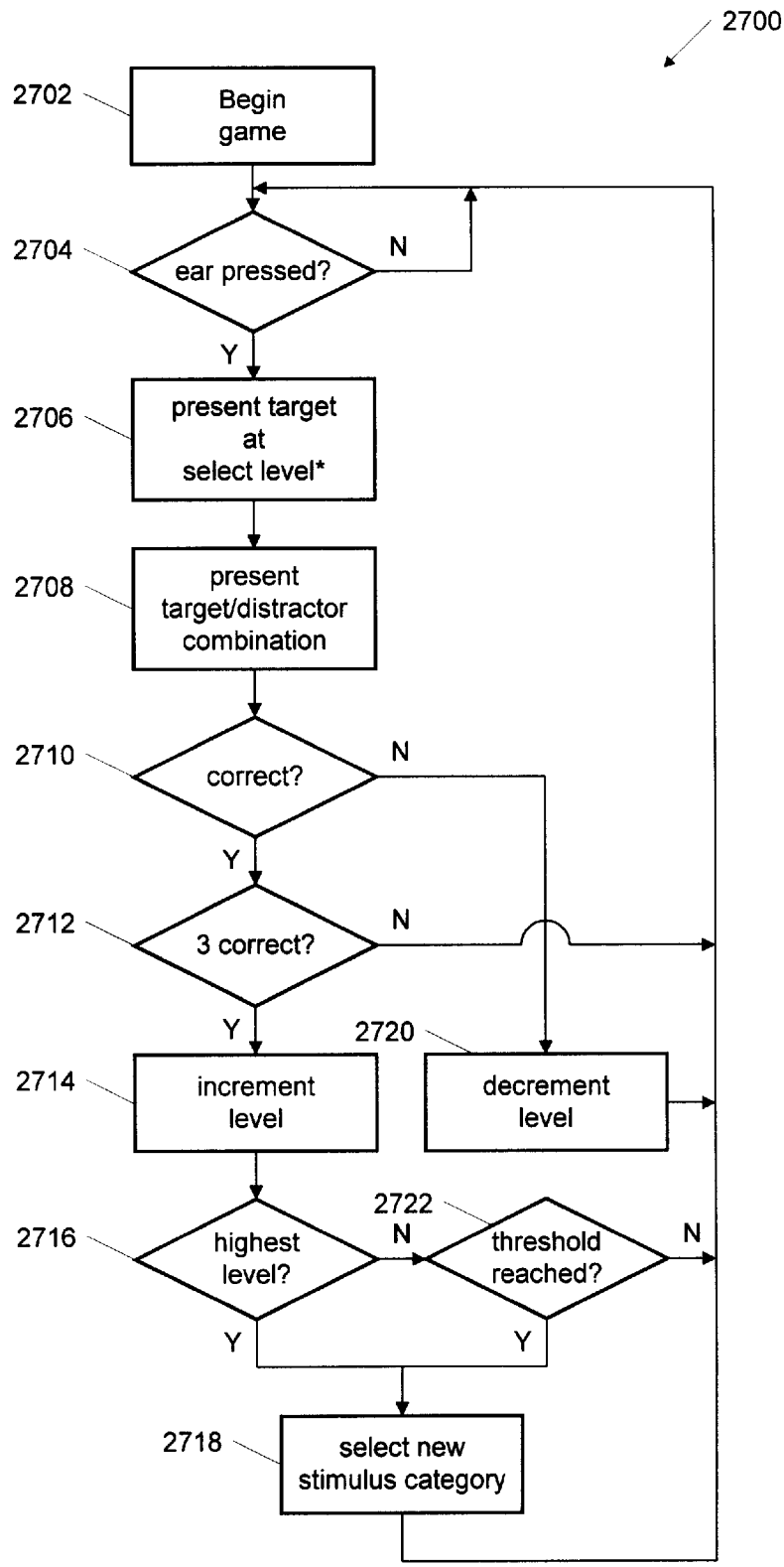
FIG. 27 is a flow chart illustrating the adaptive auditory training process embodied in the game Phoneme Identification.

Referring now to FIG. 27, a flow chart 2700 is provided that illustrates play of the Phoneme Identification game. Play begins at block 2702 and proceeds to decision block 2704.

At decision block 2704, a determination is made as to whether the ear/hand button 2402 has been pressed. If not, then flow proceeds back to decision block 2704 until the subject chooses to hear the target phoneme. If the ear/hand button 2402 has been pressed, flow proceeds to block 2706.

At block 2706 a target phoneme is presented at an appropriate processing level. If this is the first time a subject has played the game, then the processing level for the phonemes is level 1, and the ISI between the target and distractor phonemes is 500 ms. Otherwise, the skill level pertains to the historical success of the subject, with the particular phoneme pair, as will be further described below. Flow then proceeds to block 2708.

At block 2708, two animals are shown, corresponding to the phoneme pair being tested, speaking the processed target and distractor phonemes, in random order. Flow then proceeds to decision block 2710.

At decision block 2710, a determination is made as to whether the subject has correctly selected the animal speaking the target phoneme. If not, then flow proceeds to block 2720. If the subject has correctly responded to the trial, flow proceeds to decision block 2712.

At block 2720, the skill level for play is decremented. For example, if the processing level is at level 1, having consonant duration of 150%, and emphasis of 20 db, but the ISI between the target and distractor phonemes is at 100 ms, the game will drop back to a skill level where the ISI is at 110 ms. However, if the skill level of play is already at level 1, then no change in processing is made.

At decision block 2712, a determination is made as to whether the subject has correctly responded in the last 3 consecutive trials. If not, then flow proceeds back to decision block 2704, awaiting another trial to begin. However, if the subject has correctly responded to the last 3 trials, flow proceeds to block 2714. It should be appreciated that the procedure illustrated in blocks 2710–2712 is the 3-up, 1-down rule, previously described in the Circus Sequence game above.

At block 2714, the skill level of the game is incremented. For example, if a subject has correctly responded to 3 consecutive trials, and is at a processing level of 100% duration, 20 dB emphasis, and an ISI of 0 ms, the next level of play will be at 100% duration, 10 dB emphasis, and an ISI of 500 ms. Flow then proceeds to decision block 2716.

At decision block 2716, a determination is made as to whether the highest skill level has been reached. If the subject has correctly responded to the last 3 trials, with no processing of the phonemes, and with minimal ISI between the target and distractor, then flow proceeds to block 2718. Otherwise flow proceeds to decision block 2722.

At decision block 2722, a determination is made as to whether the subject has reached a threshold. In one embodiment, a threshold is reached if the subject has had 8 skill level reversals within 6 skill levels of each other. If the subject has not reached a threshold, flow proceeds back to block 2704 where another trial is begun. If the subject has reached a threshold, flow proceeds to block 2718.

At block 2718, a new stimulus category is selected. That is, a new phoneme pair is selected for testing. Thus, if the subject has been tested with the phoneme pair ba-da, and has either mastered the pair by reaching the highest skill level, or has reached a threshold, then an alternate phoneme pair is selected, say aba-ada. Flow then proceeds back to block 2704 where a trial awaits using the new phoneme pair. In one embodiment, the skill level used for the new phoneme pair is selected to be 5 less than previously achieved for that pair. Or, if the subject has not yet been tested on the new phoneme pair, the skill level is set to 1. Testing continues indefinitely, or for the time allotted for Phoneme Identification on the subject's daily training schedule.

Figure 28:
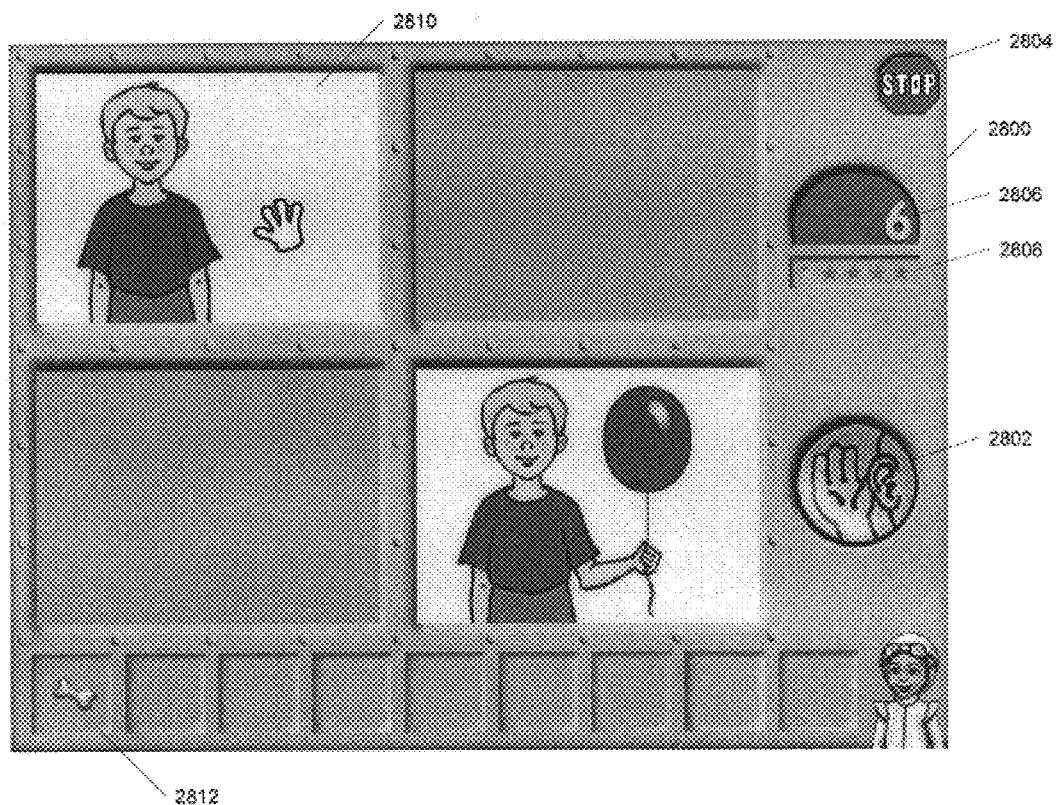
FIG. 28 is a pictorial representation of a game entitled "Language Comprehension Builder" according to the present invention.

Referring now to FIG. 28, a screen shot 2800 is shown for the seventh game in the Fast Forward program, Language Comprehension Builder. The screen shot 2800 contains an ear/hand button 2802 for beginning a trial, a stop sign 2804 for exiting the game, a number score 2806 corresponding to the number of correct responses, and level icons 2808 for indicating the processing level that is currently being tested. In addition, four windows 2810 are shown for containing one to four stimulus images, according to the particular trial being presented. If less than four stimulus images are required for a trial, they are placed randomly within the four windows 2810. At the bottom of the screen 2800 are smaller progress windows 2812 for holding progress elements. The progress elements provide a visual indicator to a subject of his/her progress. As in previously discussed games, when all of the progress elements are obtained, usually ten correct responses, a reward animation is presented to the subject. In one embodiment of this game, the reward animation builds a space ship out of the progress elements.

The stimulus that is provided to the subject is in the form of command sentences. The sentences are divided into 7 comprehension levels, with each level having between 4 to 10 groups of sentences. Each group has 5 sentences. For each stimulus sentence, a corresponding image is provided, with 1–3 distractor images. The subject is to listen to the stimulus sentence and select the corresponding image.

Figure 30:
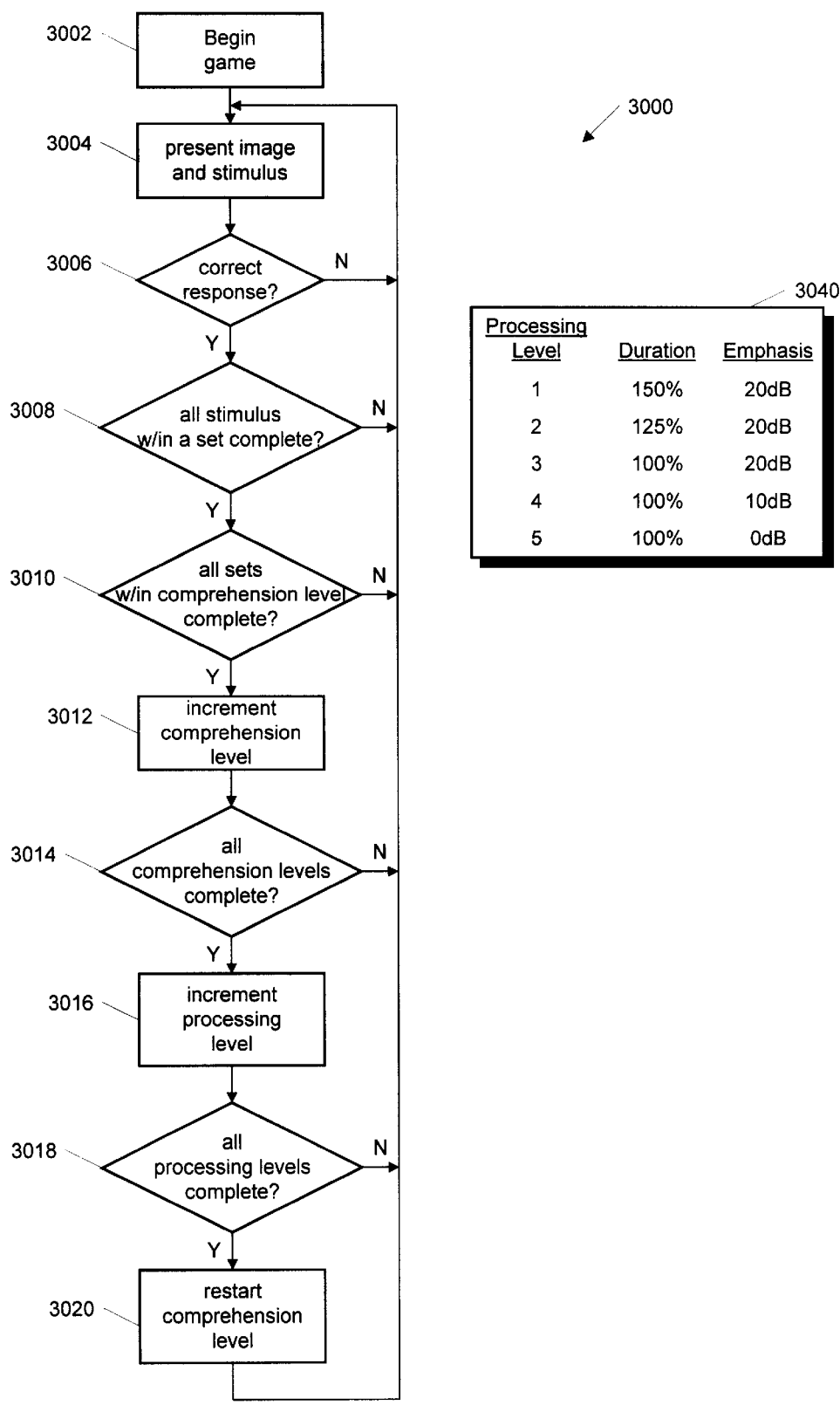
FIG. 30 is a flow chart illustrating the adaptive auditory training procedures embodied in the game Language Comprehension Builder.

Each of the stimulus sentences may be processed by stretching words, or selected phonemes, in time, and by emphasizing particular frequency envelopes, as shown by table 3040 in FIG. 30. Stretching and emphasis of selected words/phonemes is similar to that described above in other games. The stimulus sentences presented to a subject are provided in Appendix A.

Figure 29:
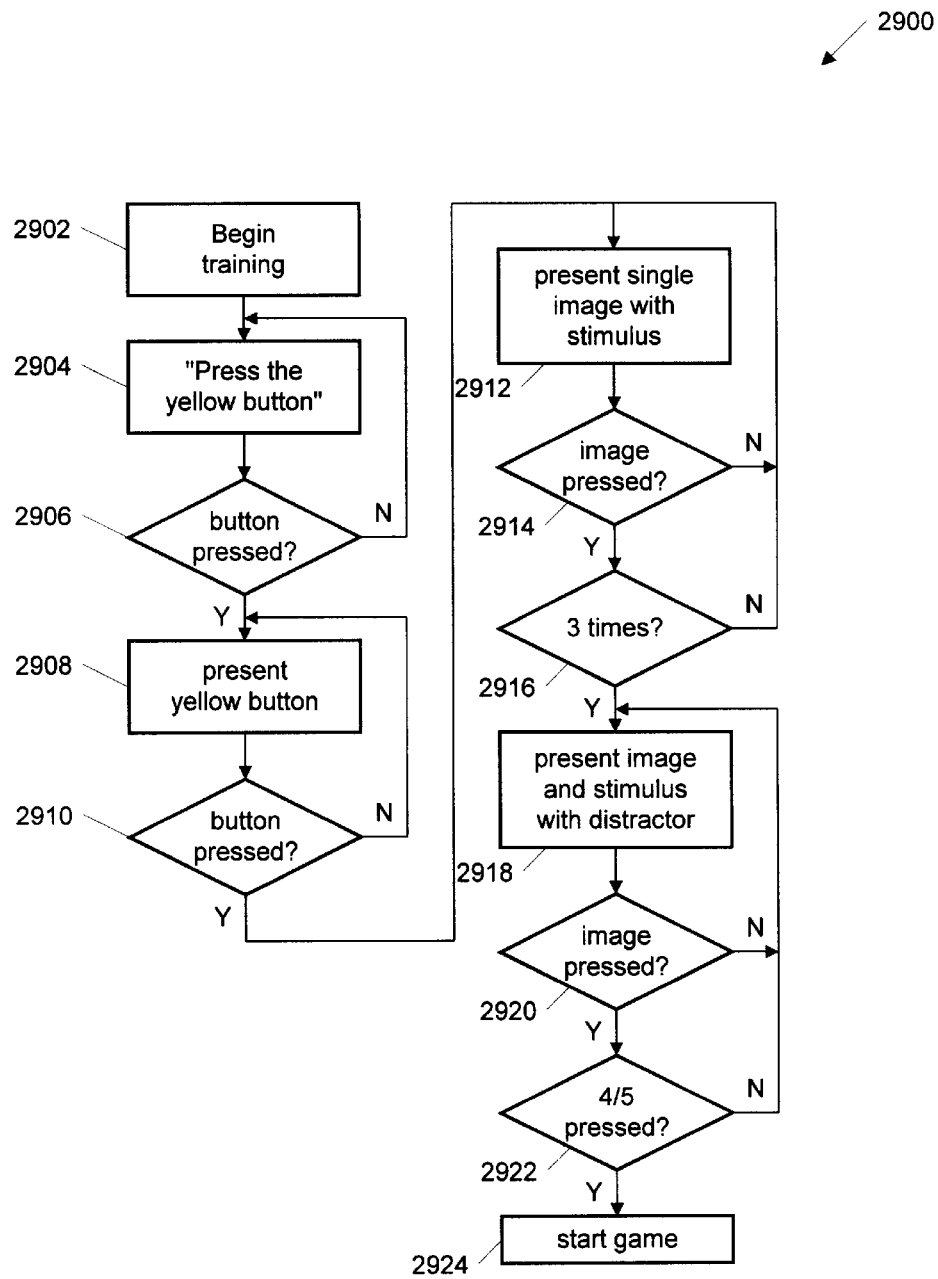
FIG. 29 is a flow chart illustrating the initial training procedures embodied in the game Language Comprehension Builder.

Referring now to FIG. 29, a flow chart 2900 is provided to illustrate the training tutorial aspect of the game. Training begins at block 2902 and proceeds to block 2904.

At block 2904, the subject is prompted to "press the yellow button". That is, the ear/hand button 2802. Flow then proceeds to decision block 2906.

At decision block 2906, a determination is made as to whether the subject has selected the ear/hand button 2802. If not, flow proceeds back to block 2904 where the subject is again prompted, after a predetermined interval. If the subject has pressed the button, flow proceeds to block 2908.

At block 2908, the ear/hand button 2802 is presented, without audio prompting. Flow then proceeds to decision block 2910.

At decision block 2910, a determination is made as to whether the subject has pressed the button 2802. If not, then the subject stays in this loop until the button 2802 is pressed. Once pressed, flow proceeds to block 2912.

At block 2912, a subject is presented with a single image and corresponding audio stimulus. In one embodiment, the stimulus is processed at level 1, with 150% duration and 20 dB selective emphasis. Flow then proceeds to decision block 2914.

At decision block 2914, a determination is made as to whether the subject has selected the image corresponding to the presented stimulus. If not, then flow proceeds back to block 2912 where the subject is again prompted with the stimulus, after a predetermined interval. However, if the subject selected the image, flow proceeds to decision block 2916.

At decision block 2916, a determination is made as to whether the subject has correctly selected an image, 3 times. If not, then flow proceeds back to block 2912 where another image/stimulus combination is presented. However, if the subject has correctly selected an image, 3 times, flow proceeds to block 2918.

At block 2918, an image/stimulus combination is presented, along with a distractor image. Flow then proceeds to decision block 2920.

At decision block 2920, a determination is made as to whether the subject selected the appropriate image. If not, then flow proceeds back to block 2918. However, if the subject selected the correct image, flow proceeds to decision block 2922.

At decision block 2922, a determination is made as to whether the subject has correctly responded to 4 out of 5 trials, on a sliding scale. If not, then flow proceeds back to block 2918. If the subject has correctly responded 4 out of the last 5 trials, flow proceeds to block 2924 allowing the subject to start the game.

Now referring to FIG. 30, a flowchart 3000 is shown illustrating operation of the Language Comprehension Builder game. The game begins at block 3002 and proceeds to block 3004.

At block 3004 an image and stimulus combination is presented to the subject. In one embodiment, the game begins by selecting a group from Level 2, and then by randomly selecting one of the trials from the selected group. The processing of the sentence is performed at 150% duration with 20 dB selected emphasis. Flow then proceeds to decision block 3006.

At decision block 3006, a determination is made as to whether the subject correctly selected the image associated with the stimulus sentence. If not, the subject is shown the correct response, and flow proceeds back to block 3004 where another stimulus/image combination from the same group is presented. If the subject selects the correct image, flow proceeds to decision block 3008.

At decision block 3008, a determination is made as to whether all sentences within a stimulus set have been successfully completed. As mentioned above, the program begins in Level 2, by selecting a particular stimulus set for presentation. The program stays within the selected stimulus set until all stimulus sentences have been responded to correctly. The program then selects another stimulus set from within Level 2. If the subject has not correctly completed all sentences within a stimulus set, flow proceeds back to block 3004 where another sentence is presented. If the subject has completed all stimulus within a set, flow proceeds to decision block 3010.

At decision block 3010, a determination is made as to whether all sets within a particular comprehension level have been completed. If not, then a new set is selected, and flow proceeds back to block 3004. However, if all sets within a comprehension level have been completed, flow proceeds to block 3012.

At block 3012, the comprehension level is incremented. In one embodiment, a subject proceeds through comprehension levels 2–6, in order, with levels 7 and 8 interspersed within levels 3–6. Flow then proceeds to decision block 3014.

At decision block 3014, a determination is made as to whether all comprehension levels have been completed. If not, then flow proceeds back to block 3004 where the subject is presented with an image/stimulus combination from a stimulus set within the new comprehension level. However, if the subject has progressed through all stimulus sets for all comprehension levels, flow proceeds to block 3016.

At block 3016, the processing level applied to the stimulus sets is increased. The processing levels are shown in table 3040. For example, if a subject has just completed processing level 2, having a duration of 125%, and 20 dB emphasis, the processing level is incremented to level 3. This will present all stimulus at 100% duration, and 20 dB emphasis. In addition, it will reset the comprehension level to level 2, and will restart the stimulus set selection. Flow then proceeds to decision block 3018.

At decision block 3018, a determination is made as to whether all processing levels have been completed. If not, then flow proceeds back to block 3004 where a stimulus set from level 2 is presented to the subject, at the new processing level. However, if all the processing levels have been completed, the subject remains at processing level 5 (normal speech). Flow then proceeds to block 3020.

At block 3020, the comprehension levels are reset, so that the subject is presented again with stimulus from level 2. However, no alteration in the stimulus is performed. The subject will remain at processing level 5.

Study has shown that several weeks are required for a subject to advance through all of the comprehension levels, and all of the processing levels. Therefore, when a subject begins each day, he/she is started within the comprehension level, and stimulus set that was last played. And, the stimulus set will be presented at the processing level last played.

In Language Comprehension Builder, as in all of the other games, detailed records are kept regarding each trial, indicating the number of correct responses and incorrect responses, for each processing level, skill level and stimulus set. These records are uploaded to a central server at the end of each day, so that a subject's results may be tabulated and analyzed by an SLP, either working directly with a subject, or remotely. Based on analysis by the SLP, modification to training parameters within Fast ForWord may be made, and downloaded to the subject. This allows a subject to begin each day with a sensory training program that is individually tailored to his/her skill level.

The above discussion provides a detailed understanding of the operation of the present invention as embodied in the game modules within the program entitled Fast ForWord. Each of the game modules present different problems to a subject, using modified phonemes, frequency sweeps or speech commands that are stretched, emphasized or separated in time, according to the subject's ability, and according to predefined processing parameters within the program. Although alternative acoustic processing methodologies may be used, discussion will now be directed at algorithms developed specifically for use by the above described games.

In one embodiment, a two-stage speech modification procedure was used. The first stage involved time-scale modification of speech signals without altering its spectral content. The time scale modification is called the "phase vocoder", and will be further described below. The second speech modification stage that was developed uses an algorithm that differentially amplifies and disambiguates faster phonetic elements in speech. "Fast elements" in speech are defined as those that occur in the 3–30 Hz range within an envelope of narrow-band speech channels of a rate changed speech signal. An emphasis algorithm for these fast elements was implemented using two methods: a filter-bank summation method and an overlap-add method based on a short-time Fourier transform. Both of these emphasis algorithms will be further described below.

Time-scale modification

Figure 31:
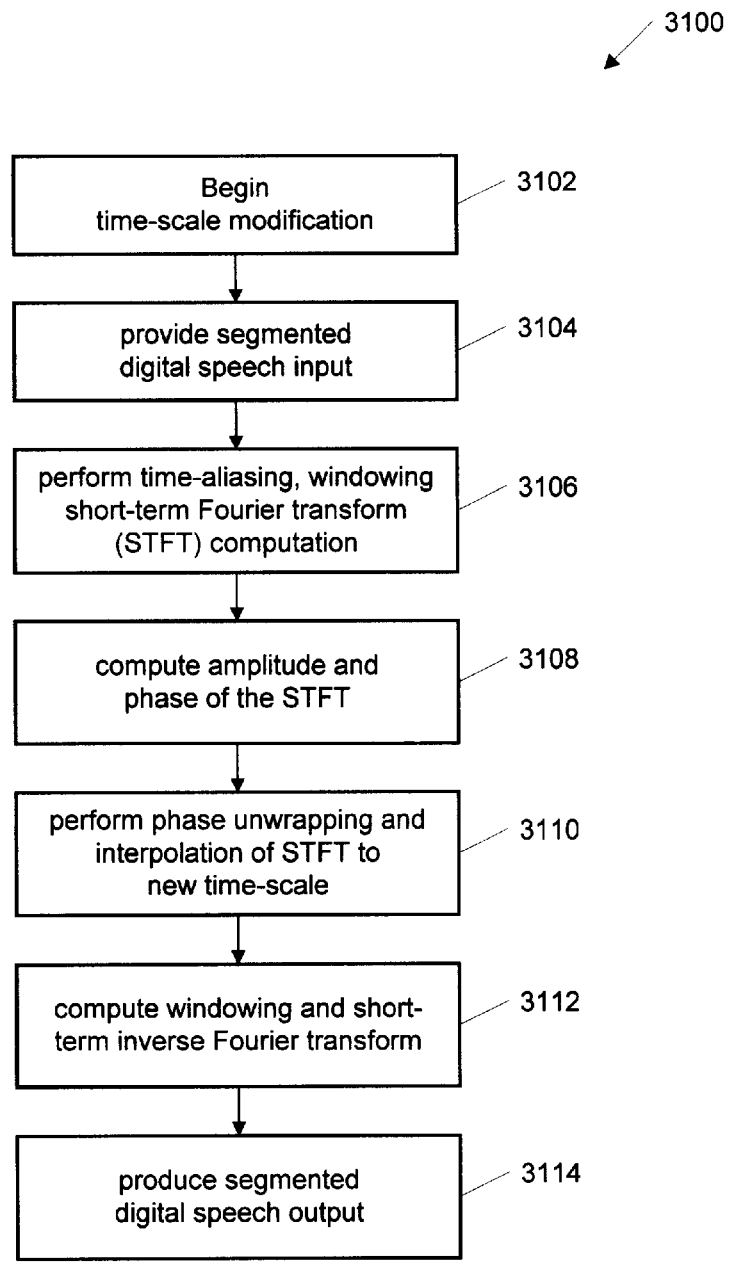
FIG. 31 is a flow chart illustrating a time-scale modification algorithm for modifying acoustic elements according to the present invention.

Referring to FIG. 31, a flow chart 3100 is provided that illustrates time-scale modification of speech signals according to the present invention. Modification begins at block 3102 and proceeds to block 3104.

At block 3104, segmented digital speech input is provided to a processor. The segmented speech is assumed to be broadband and composed of a set of narrow-band signals obtained by passing the speech segment through a filter-bank of band-pass filters. The speech signals may be written as follows:

$$f(t) \cong \sum_{n=1}^{N} f_n(t)$$

where $$f_n(t) = \int_{-\infty}^{t} f(t)h(t-\tau)\cos[\omega_n(t-\tau)]d\tau$$

This is the convolution integral of the signal f(t) and h(t), a prototypical low-pass filter modulated by $\cos[\omega_n(t)]$ where $\omega_n$ is the center frequency of the filters in the filter-bank, an operation commonly referred to as heterodyning. Flow then proceeds to block 3106.

At block 3106, the above integral is windowed, and a short-term Fourier transform of the input signal is evaluated at the radian frequency $\omega_n$ using an FFT algorithm. The complex value of this transform is denoted:

$$f_n(t) = |F(\omega_n,t)|\cos[\omega_n t + \phi_n(\omega_n,t)]$$

where $\phi_n(\omega_n,t)$ is the phase modulation of the carrier cos $[\omega_n(t)]$. Flow then proceeds to block 3108.

At block 3108 the amplitude and phase of the STFT is computed. It is known that the phase function is not a well behaved function, however its derivative, the instantaneous frequency, is bounded and is band limited. Therefore, a practical approximation for $f_n(t)$ is:

$$f_n(t) \cong |F(\omega_n, t)| \cos\left[\omega_n t + \int_0^t \phi^*_n(\omega_n, t)\right]$$

where $\phi^*$ is the instantaneous frequency. Flow then proceeds to block 3110.

At block 3110 $\phi^*$ can be computed from the unwrapped-phase of the short-term Fourier transform. A time-scaled signal can then be synthesized as follows by interpolating the short-term Fourier transform magnitude and the unwrapped phase to the new-time scale as shown below.

$$f(\beta t) \cong \sum_{n=0}^{\beta N} |F(\omega_n, \beta t)| \cos\left(\beta\left(\omega_n t + \int_0^t \phi^*_n(\omega_n, t)\right)\right)$$

where $\beta$ is the scaling factor which is greater than one for time-scale expansion. An efficient method to compute the above equation makes use of cyclic rotation and the FFT algorithm along with an overlap-add procedure to compute the short-time discrete Fourier transform. Appropriate choice of the analysis filters h(t) and interpolating filters (for interpolation of the short-term Fourier transform to the new time-scale) are important to the algorithm. In one embodiment, linear interpolation based on the magnitude and phase of the short-time Fourier transform was used. The analysis filter h(t) was chosen to be a Kaiser window multiplied by an ideal impulse response as shown:

$$h(n) = \frac{N}{\pi n} \sin\left(\frac{\pi n}{N}\right) \text{kaiser}(n, 6.8)$$

where $$\text{kaiser}(n, \alpha) = \left\{\frac{I_0\left[\alpha\sqrt{(1 - [(n - N/2)/N/2]^2)}\right]}{I_0(\alpha)}\right\}, 0 \le n \le N$$

where $I_0(\alpha)$ is the zeroth-order modified Bessel function of the first kind and N is the length of the analysis window over which the FFT is computed. Flow then proceeds to block 3112.

At block 3112, a short-term inverse FFT is computed to produce digital speech output. This output is then provided at block 3114.

Filter -bank emphasis algorithm

Figure 32:
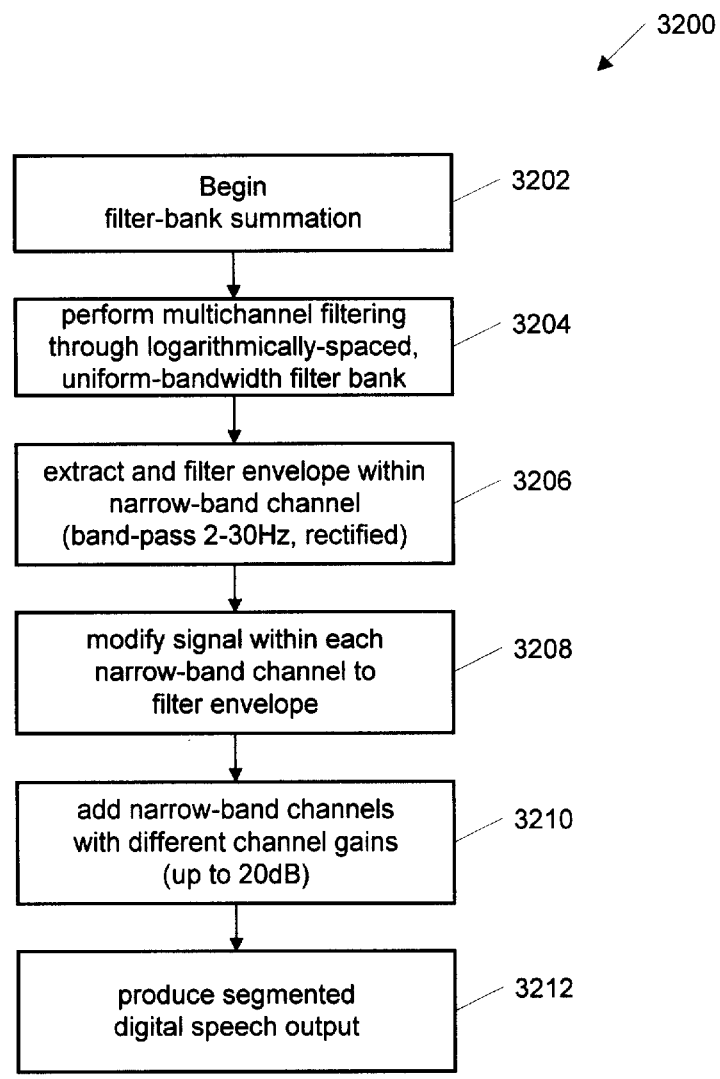
FIG. 32 is a flow chart illustrating a filter-bank summation emphasis algorithm for modifying acoustic elements according to the present invention.

Now referring to FIG. 32, a flow chart 3200 is shown that illustrates implementation of an emphasis algorithm according to the present invention. The algorithm begins at block 3202 and proceeds to block 3204.

At block 3204, it is assumed that the speech signal can be synthesized through a bank of band-pass filters, as described above. This time, however, no heterodyning of a prototypical low-pass filter is used. Instead, a set of up to 20 second-order Butterworth filters with center frequencies logarithmically spaced between 100 and the nyquist frequency are used. The output of each band-pass filter resulted in a narrow-band channel signal $f_n(t)$. Flow then proceeds to block 3206.

At block 3206, we computed the analytical signal as follows:

$$a_n(n) = f_n(n) + iH(f_n(n))$$

where H(n) is the Hilbert transform of a signal defined as:

$$H(n) = f_n(n) * \left(\frac{1}{\pi t}\right)$$

$$= \int f_n(\tau) \frac{1}{\pi(n - \tau)} d\tau$$

The Hilbert transform was computed using the FFT algorithm. It is known that the absolute value of the analytical signal is the envelope of a narrow-band signal. Thus, an envelope $e_n(n)$ is obtained by the following operation:

$$e_n(n) = |a_n(n)|$$

The envelope within each narrow-band channel is then band-pass filtered using a second order Butterworth filter with the cutt-offs set usually between 3–30 Hz (the time scale at which phonetic events occur in rate changed speech). The band pass filtered envelope is then rectified to form the new envelope as follows:

$$e_n^{new}(n) = S(e_n(n) * g(n))$$

where $$S(x) = x \text{ for } x \ge 0, \text{ otherwise } S(x) = 0$$

and g(n) is the impulse-response of the band-pass second order Butterworth filter. Flow then proceeds to block 3208.

At block 3208, the signal is modified within each band-pass channel to carry this new envelope, as shown below:

$$f_n^{new}(n) = \left[f_n(n) S\left(\frac{e_n^{new}(n)}{e_n(n)}\right)\right] * h(n)$$

Flow then proceeds to block 3210.

At block 3210 the modified signal is obtained by summing the narrow-band filters with a differential gain for each channel as follows:

$$f^{new}(n) = \sum_n w_n f_n^{new}(n)$$

where $w_n$ is the gain for each channel. The envelope is modified only within a specified frequency range from 1–10 KHz which normally spans about 16 channels. Flow then proceeds to block 3212.

At block 3212 segmented digital speech output is provided.

Overlap-add emphasis algorithm

Figure 33:
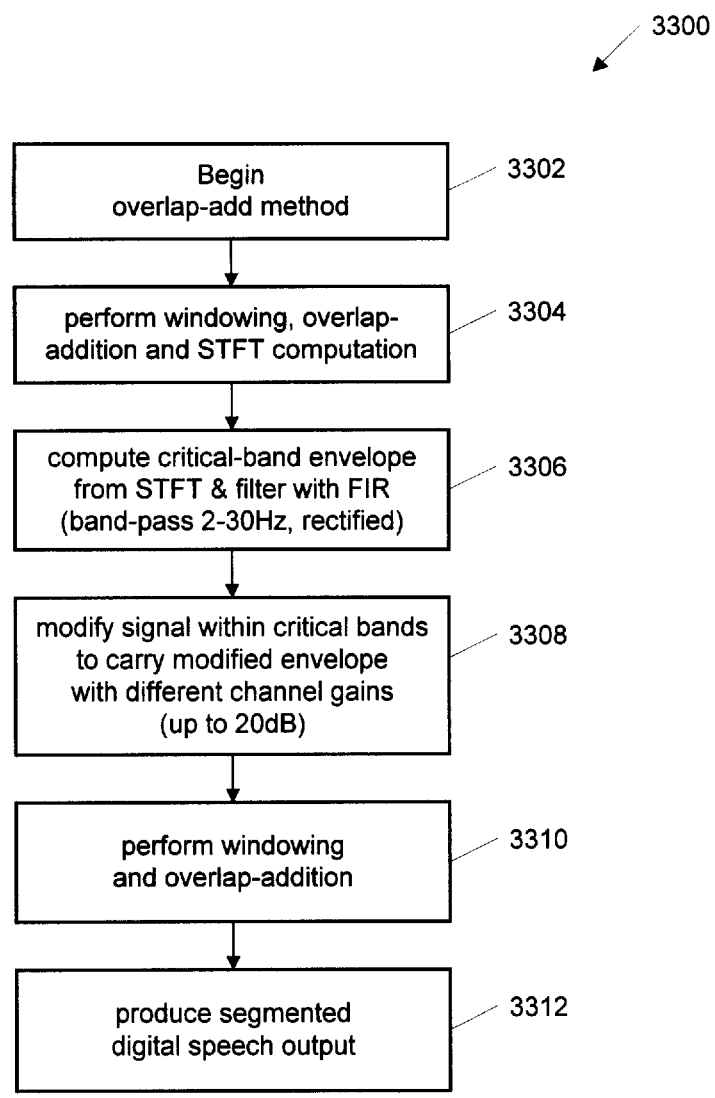
FIG. 33 is a flow chart illustrating an overlap-add emphasis algorithm for modifying acoustic elements according to the present invention.

Referring to FIG. 33, a flow chart 3300 for an alternative emphasis algorithm is provided. This algorithm improves upon the filter-bank summation described above by making use of the property of equivalence between the short-time Fourier transform and the filter-bank summation algorithm. In this embodiment, the short-time Fourier transform is computed using an overlap-add procedure and the FFT algorithm. Flow begins at block 3302 and proceeds to block 3304.

At block 3304, the short-time Fourier transform is computed over a sliding window given by the following equation:

$$X_k(r) = \sum_{m=-\infty}^{\infty} h(r-n)x(n)e^{i2\pi nk/N}$$

where h(n) is a Hamming window and the overlap between sections was chosen to be less than a quarter the length of the analysis window. The envelope can then be obtained within narrow-band channels from the absolute value of the short-time Fourier transform. The number of narrow-band channels is equal to half the size of the length over which the FFT is computed.

The energy of the envelope within critical band channels is then averaged, as shown:

$$f_n(r) = \sum_{C_{n-1} \leq k \leq C_n} |X_k(r)|$$

where $C_n$ is the corner-frequency of the critical-band channel n. At present, critical-band frequencies for children with LLI are unknown, therefore the present invention approximates the bands using parameters proposed by Zwicker. See E. Zwicker and E. Terhardt, "Analytical expressions for critical-band rate and critical bandwidth as a function of frequency," J. Acoust. Soc. Ame., vol. 68, pp. 1523–25, 1980. As critical band frequencies for children with LLI become available, they can be incorporated into the present invention.

The envelope within each critical-band channel is then band-pass-filtered with cut off's set usually between 3–30 Hz with type I linear phase FIR equiripple filters. The band-pass filtered envelope is then threshold rectified. In contrast to the filter-bank emphasis algorithm, the modified envelope is added to the original envelope to amplify the fast elements while not distorting the slower modulations. This is given by the following equation:

$$X_k^{new}(n) = \left[ X_k(n) T\left( \frac{e_n^{new}(n)}{e_n(n)} \right) \right]$$

where, $T(x) = x + 1$ for $x > 0$, otherwise 0

Flow then proceeds to block 3308.

At block 3308, a modified signal is obtained by summing the short-time Fourier transform using a weighted overlap-add procedure as shown below:

$$f^{new}(n) = \sum_{s=-\infty}^{\infty} g(n-s) \frac{1}{N} \sum_{k=0}^{N-1} X_k^{new}(n) e^{i2\pi nk/N}$$

where g(n) is the synthesis filter which was also chosen to be a Hamming window. Flow then proceeds to block 3310. At block 3310, windowing and over-lap addition for the algorithm is performed. Flow then proceeds to block 3312 where segmented digital speech output is provided.

Although the present invention and its objects, features, and advantages have been described in detail, other embodiments are encompassed by the invention. For example, a number of different games have been shown, each dealing with a stimulus set that is processed in the time domain, and presented to a subject in a manner that the subject can understand. The processing is designed to emphasize or stretch those components of speech that are the most difficult for an LLI subject to differentiate, so that they may be more easily understood. In addition, the processing allows distinct frequency sweeps, phonemes or words to be separated in time, first by a significant amount, say 500 ms, with the amount of separation being gradually reduced to that of normal speech. Once a subject gains success at distinguishing between similar speech elements, at a high level of processing, the amount of processing is gradually reduced until it reaches the level of normal speech. The particular games used to train subjects have distinct advantages, but are not exclusive. Other games are anticipated that will incorporate the novel aspects of the present invention, to further train a subject's temporal processing ability to recognize and distinguish between short duration acoustic events that are common in speech.

Furthermore, the Fast ForWord program has been shown for execution on a personal computer, connected to a central server. However, as technology advances, it is envisioned that the program could be executed either by a diskless computer attached to a server, by a handheld processing device, such as a laptop, or eventually by a palmtop device such as a Nintendo GameBoy. As long as the graphical images and auditory prompts can be presented in a timely fashion, and with high quality, the nature of the device used to present the material is irrelevant.

Those skilled in the art should appreciate that they can readily use the disclosed conception and specific embodiments as a basis for designing or modifying other structures for carrying out the same purposes of the present invention without departing from the spirit and scope of the invention as defined by the appended claims.

APPENDIX A

Level 2

1. Attribute/Stative
   Stimulus: The ball is big
   The man is big.
   The ball is small.
   The ball is big.
   Stimulus: The cup is broken
   The wind up toy car is broken.
   The cup is broken.
   The cup is not broken.
   Stimulus: The baby is crying
   The baby is not crying.
   The boy is crying.
   The baby is crying.
   Stimulus: The box is open
   The box is open.
   The box is closed.
   The can is open.
   Stimulus: The girl is dirty
   The girl is dirty
   The shoe is dirty.
   The shoe is not dirty.
2. Simple Negation
   Stimulus: The boy is not eating
   The boy is not eating.
   The boy is eating.
   Stimulus: The boy is not riding
   The boy is not riding.
   The boy is riding.
   Stimulus: The baby is not crying
   The baby is crying.
   The baby is not crying.
   Stimulus: The boy does not have a balloon The boy has a balloon.
The boy does not have a balloon.
Stimulus: The girl does not have shoes
The girl does not have shoes.
The girl has shoes.
3. Object Pronouns: Him&Her
   Stimulus: Point to her.
   A girl doll.
   A boy doll.
   Stimulus: Point to him
   A girl doll.
   A boy doll.
   Stimulus: Point to her.
   A girl doll.
   A boy doll.
   Stimulus: Point to him.
   A girl doll.
   A boy doll.
   Stimulus: Point to her.
   A girl doll.
   A boy doll.
4. Possession
   Stimulus: The clown has a balloon.
   The clown has a balloon
   The clown has a flower.
   The boy has a balloon.
   Stimulus: The dog has spots.
   The dog does not have spots.
   The boy has spots.
   The dog has spots.
   Stimulus: The tree has apples.
   The girl has apples.
   The tree has apples.
   The tree does not have apples.
   Stimulus: The bunny has a carrot.
   The bunny does not have a carrot.
   The cat has a carrot.
   The bunny has a carrot.
   Stimulus: The girl has shoes.
   The girl has shoes.
   The girl does not have shoes.
   The clown has shoes.
5. Lexicon Descriptions
   Stimulus: Point to dark.
   Dirty example.
   Down example.
   Dark example.
   Big example.
   Stimulus: Point to big.
   Blue example.
   Big example.
   Open example.
   Small example.
   Stimulus: Point to dirty.
   Dirty example.
   Dark example.
   Hot example.
   Down example.
   Stimulus: Point to yellow
   Yellow example.
   Small example
   Broken example.
   Blue example.
   Stimulus: Point to off.
   On example.
   Open example.
   Off example.
   Wet example.
6. Lexicon Action Words
   Stimulus: Point to wash.
   Sweep example.
   Fall example.
   Wash example.
   Run example.
   Stimulus: Point to run.
   Sing example.
   Jump example.
   Write example.
   Run example.
   Stimulus: Point to kick.
   Throw example.
   Kick example.
   Push example.
   Cry example.
   Stimulus: Point to drink.
   Eat example.
   Run example.
   Drink example.
   Tear example.
   Stimulus: Point to pull.
   Pull example.
   Push example.
   Throw example.
   Play example.

Level 3
7. Noun Singular/Plural (By Inflection Only)I
   Stimulus: Point to the picture of the cups.
   Point to the picture of the cup.
   Point to the picture of the cups.
   Stimulus: Point to the picture of the boat.
   Point to the picture of the boat.
   Point to the picture of the boats.
   Stimulus: Point to the picture of the balloons.
   Point to the picture of the balloons.
   Point to the picture of the balloon.
   Stimulus: Point to the picture of the houses.
   Point to the picture of the house.
   Point to the picture of the houses.
   Stimulus: Point to the picture of the cat.
   Point to the picture of the cat.
   Point to the picture of the cats.
8. Qualifiers: None
   Stimulus: Which clown has none?
   The clown has many.
   The clown has some.
   The clown has one.
   The clown has none.
   Stimulus: Which tree has none?
   The tree has none.
   The tree has one.
   The tree has some.
   The tree has many.
   Stimulus: Which dog has none?
   The dog has some.
   The dog has many.
   The dog has none.
   The dog has one.
   Stimulus: Which duck has none?
   The duck has many.
   The duck has none.
   The duck has one.
   The duck has some.
   Stimulus: Which wagon has none?
   The wagon has some.

The wagon has none.
The wagon has many.
The wagon has one.
9. Subject Relativization
   Stimulus: The boy who is mad is pulling the girl.
   The boy who is happy is pulling the girl.
   The boy who is mad is pulling the girl.
   The girl who is mad is pulling the boy.
   The girl who is happy is pulling the boy.
   Stimulus: The girl who is mad is pushing the boy.
   The girl who is happy is pushing the boy.
   The boy who is mad is pushing the girl.
   The girl who is mad is pushing the boy.
   The boy who is happy is pushing the girl.
   Stimulus: The clown who is big is chasing the girl.
   The clown who is big is chasing the girl.
   The girl who is little is chasing the clown.
   The girl who is big is chasing the clown.
   The clown who is little is chasing the girl.
   Stimulus: The girl who is happy is pulling the boy.
   The boy who is happy is pulling the girl.
   The girl who is mad is pulling the boy.
   The boy who is mad is pulling the girl.
   The girl who is happy is pulling the boy.
   Stimulus: The clown who is little is chasing the girl.
   The girl who is little is chasing the clown.
   The clown who is big is chasing the girl.
   The girl who is big is chasing the clown.
   The clown who is little is chasing the girl.
10. Active Voice Word Order
    Stimulus: The boy is pulling the girl.
    The boy is pulling the ball.
    The girl is pulling the boy.
    The boy and the girl are pulling the wagon.
    The boy is pulling the girl.
    Stimulus: The boy is pushing the girl.
    The girl is pushing the boy.
    The boy is pushing the girl.
    The boy is pushing the clown.
    They are pushing the ball.
    Stimulus: The girl is pulling the boy.
    The girl is pulling the boy.
    They are pulling the wagon.
    The dog is pulling the boy.
    The boy is pulling the girl.
    Stimulus: The boy is kicking the girl.
    They are kicking the balls.
    The girl is kicking the boy.
    The clown is kicking the girl.
    The boy is kicking the girl.
    Stimulus: The girl is washing the boy.
    They are washing the tub.
    The girl is washing the dog.
    The girl is washing the boy.
    The boy is washing the girl.
11. Comparative with More
    Stimulus: Which one is more happy?
    Which one is less happy?
    Which one is more happy?
    Stimulus: Which one is more hairy?
    Which one is more hairy?
    Which one is less hairy?
    Stimulus: Which one is more skinny?
    Which one is less skinny?
    Which one is more skinny?
    Stimulus: Which one is more dirty?
    Which one is more dirty?

Which one is less dirty?
Stimulus: Which one is more messy?
Which one is more messy?
Which one is less messy?
12. Reduced Subject Relative Clauses
    Stimulus: The boy frowning is pulling the girl.
    The girl frowning is pulling the boy.
    The boy smiling is pulling the girl.
    The girl smiling is pulling the boy.
    The boy frowning is pulling the girl.
    Stimulus: The boy smiling is pushing the girl.
    The girl frowning is pushing the boy.
    The boy smiling is pushing the girl.
    The girl smiling is pushing the boy.
    The boy frowning is pushing the girl.
    Stimulus: The boy frowning is pushing the girl.
    The boy frowning is pushing the girl.
    The girl smiling is pushing the boy.
    The boy smiling is pushing the girl.
    The girl frowning is pushing the boy.
    Stimulus: The girl smiling is pushing the boy.
    The boy smiling is pushing the girl.
    The girl frowning is pushing the boy.
    The girl smiling is pushing the boy.
    The boy frowning is pushing the girl.
    Stimulus: The girl frowning is pulling the boy.
    The girl frowning is pulling the boy.
    The boy frowning is pulling the girl.
    The girl smiling is pulling the boy.
    The boy smiling is pulling the girl.
13. Complex Negation
    Stimulus: The clown that is not on the box is little.
    The clown that is not on the box is little.
    The clown that is on the box is little.
    The clown that is not on the box is big.
    The clown that is on the box is big.
    Stimulus: The girl that is chasing the clown is not big
    The clown that is chasing the girl is big.
    The girl that is chasing the clown is not big.
    The clown that is chasing the girl is not big.
    The girl that is chasing the clown is big.
    Stimulus: The boy that is not sitting is looking at the girl.
    The girl that is not sitting is not looking at the boy.
    The girl that is not sitting is looking at the boy
    The boy that is not sitting is looking at the girl.
    The boy that is not sitting is not looking at the girl.
    Stimulus: The clown that is big is not on the box.
    The clown that is little is not on the box.
    The clown that is big is on the box.
    The clown that is little is on the box.
    The clown that is big is not on the box.
    Stimulus: The book that is not on the table is blue.
    The book that is on the table is blue.
    The book that is on the table is red.
    The book that is not on the table is blue.
    The book that is not on the table is red.
14. Noun Singular/Plural (By Inflection Only)
    Stimulus: Point to the picture of the watches.
    Point to the picture of the watch.
    Point to the picture of the watches.
    Stimulus: Point to the picture of the tubs.
    Point to the picture of the tub.
    Point to the picture of the tubs.
    Stimulus: Point to the picture of the hat .
    Point to the picture of the hats .
    Point to the picture of the hat.
    Stimulus: Point to the picture of the bunny.

Point to the picture of the bunnies.
Point to the picture of the bunny.
Stimulus: Point to the picture of the socks.
Point to the picture of the sock.
Point to the picture of the socks .
15. Comparative with/-er/
Stimulus: Which one is happier?
Which one is happier?
Which one is happy?
Stimulus: Which one is hairier?
Which one is hairier?
Which one is more bald?
Stimulus: Which one is skinnier?
Which one is heavier?
Which one is skinnier?
Stimulus: Which one is dirtier?
Which one is dirtier?
Which one is cleaner?
Stimulus: Which one is messier?
Which one is messier?
Which one is cleaner?

Level 4
16. Passive Voice Word Order
Stimulus: The boy is being pushed by the girl.
The boy is being pushed by the clown.
The clown is being pushed by the girl.
The girl is being pushed by the boy.
The boy is being pushed by the girl.
Stimulus: The dog is being pulled by the clown.
The dog is being pulled by the boy.
The clown is being pulled by the dog.
The dog is being pulled by the clown.
The girl is being pulled by the clown.
Stimulus: The girl is being kicked by the boy.
The girl is being kicked by the boy.
The clown is being kicked by the boy.
The girl is being kicked by the clown.
The boy is being kicked by the girl.
Stimulus: The boy is being chased by the girl.
The dog is being chased by the girl.
The girl is being chased by the boy.
The boy is being chased by the girl.
The boy is being chased by the dog.
Stimulus: The boy is being kicked by the girl.
The girl is being kicked by the boy.
The boy is being kicked by the girl.
The clown is being kicked by the girl.
The boy is being kicked by the clown.
17. Wh-Object Questioning
Stimulus: What is the cat chasing? (the mouse)
What is the dog chasing? (the cat)
What is the cat chasing? (the mouse)
What is the mouse chasing? (the cat)
Stimulus: Who is the clown chasing? (the boy)
Who is the girl chasing?
Who is the clown chasing?
Who is the boy chasing?
Stimulus: Who is the girl pushing? (the boy)
Who is the mother pushing?
Who is the girl pushing?
Who is the boy pushing?
Stimulus: Who is the boy pulling? (the girl)
Who is the girl pulling?
Who is the boy pulling?
Who is the clown pulling?
Stimulus: Who is the girl pulling? (the clown)
Who is the clown pulling?

Who is the girl pulling?
Who is the boy pulling?
18. Quantifiers: Some
Stimulus: Look at these wagons with deer.
Which wagon has some?
Which wagon has one?
Which wagon has some?
Which wagon has many?
Which wagon has none?
Stimulus: Look at these clown with balloons.
Which clown has some?
Which clown has one?
Which clown has none?
Which clown has some?
Which clown has many?Stimulus: Look at these ducks with babies?
Which duck has some?
Which duck has none?
Which duck has many?
Which duck has some?
Which duck has one?
Stimulus: Look at these trees with apples.
Which tree has some?
Which tree has one?
Which tree has none?
Which tree has many?
Which tree has some?
Stimulus: Look at these dogs with spots.
Which dog has some?
Which dog has some?
Which dog has none?
Which dog has one?
Which dog has many?
19. Verb Singular:
Stimulus: The fish swims.
The fish swims.
The fish swim.
Stimulus: The sheep stands.
The sheep stand.
The sheep stands.
Stimulus: The deer drinks.
The deer drinks.
The deer drink.
Stimulus: The fish eats.
The fish eat.
The fish eats.
Stimulus: The sheep jumps.
The sheep jumps.
The sheep jump.
20. Tense and Aspect: ing
Stimulus: The girl is opening the present.
The girl opened the present.
The girl is opening the present.
The girl will open the present.
Stimulus: The boy is washing his face.
The boy is washing his face.
The boy will wash his face.
The boy washed his face.
Stimulus: The boy is pouring the juice.
The boy will pour the juice.
The boy poured the juice.
The boy is pouring the juice.
Stimulus: The girl is blowing up the balloon.
The girl is blowing up the balloon.
The girl will blow up the balloon.
The girl blew up the balloon.
Stimulus: The boy is eating his dinner.

The boy will eat his dinner.
The boy ate his dinner.
The boy is eating his dinner.
21. Noun Plurals/Singulars marked by Quantifier
   Stimulus: Point to the picture of some socks.
   Point to the picture of a sock.
   Point to the picture of some socks.
   Stimulus: Point to the picture of a bag.
   Point to the picture of a bag.
   Point to the picture of some bags.
   Stimulus: Point to the picture of some dresses.
   Point to the picture of some dresses.
   Point to the picture of a dress.
   Stimulus: Point to the picture of a bunny.
   Point to the picture of a bunny.
   Point to the picture of some bunnies.
   Stimulus: Point to the picture of some dogs.
   Point to the picture of a dog.
   Point to the picture of some dogs.
40. Noun Plurals/Singulars marked by Quantifier Inflection
Note # above is for programatic purposes only. Level is correct.
   Stimulus: Point to the picture of some balloons.
   Point to the picture of a balloon.
   Point to the picture of some balloons.
   Stimulus: Point to the picture of a tree.
   Point to the picture of some trees.
   Point to the picture of a tree.
   Stimulus: Point to the picture of some cats.
   Point to the picture of some cats.
   Point to the picture of a cat.
   Stimulus: Point to the picture of some boxes.
   Point to the picture of some boxes.
   Point to the picture of a box.
   Stimulus: Point to the picture of a cake.
   Point to the picture of a cake.
   Point to the picture of some cakes.
22. Aux-be Singular
   Stimulus: The fish is swimming
   The fish is swimming.
   The fish are swimming.
   Stimulus: The sheep is standing.
   The sheep are standing.
   The sheep is standing.
   Stimulus: The deer is drinking.
   The deer is drinking.
   The deer are drinking.
   Stimulus: The fish is eating.
   The fish are eating.
   The fish is eating.
   Stimulus: The sheep is jumping.
   The sheep is jumping.
   The sheep are jumping.

Level 5

23. Case Marking Prepositions: For
   Stimulus: Show me the groceries being carried for mom
   Show me the groceries being carried for mom
   Show me the groceries being carried with mom
   Show me the groceries being carried by mom.
   Stimulus: Show me the breakfast made for mom.
   Show me the breakfast made by mom.
   Show me the breakfast made for mom.
   Show me the breakfast made with mom.
   Stimulus: Show me the drawing made for the boy.
   Show me the drawing of the boy.
   Show me the drawing made by the boy.
   Show me the drawing made for the boy.
   Stimulus: Show me the suitcase being carried for the man
   Show me the suitcase being carried with the man.
   Show me the suitcase being carried for the man.
   Show me the suitcase being carried by the man.
   Stimulus: Show me the painting made for the girl
   Show me the painting made for the girl.
   Show me the painting made by the girl.
   Show me the painting made of the girl.
24. Tense and Aspect: -ed
   Stimulus: The girl painted a picture.
   The girl painted a picture.
   The girl will paint a picture.
   The girl is painting a picture.
   Stimulus: The man sewed a shirt.
   The man will sew a shirt.
   The man is sewing a shirt.
   The man sewed a shirt.
   Stimulus: Someone tied the shoe.
   Someone is tying the shoe.
   Someone tied the shoe.
   Someone will tie the shoe.
   Stimulus: The boy tripped over the rock.
   The boy tripped over the rock.
   The boy is tripping over the rock.
   The boy will trip over the rock.
   Stimulus: The mother dressed the baby.
   The mother is dressing the baby.
   The mother will dress the baby.
   The mother dressed the baby.
25. Aux-Be Plural
   Stimulus: The deer are eating.
   The deer is eating.
   The deer are eating
   Stimulus: The sheep are jumping.
   The sheep are jumping.
   The sheep is jumping.
   Stimulus: The fish are swimming.
   The fish is swimming.
   The fish are swimming.
   Stimulus: The deer are standing.
   The deer is standing.
   The deer are standing.
   Stimulus: The sheep are eating.
   The sheep are eating.
   The sheep is eating.
26. Third Person Subject Pronouns
   Stimulus: Point to they are sitting.
   Point to she is sitting.
   Point to they are sitting.
   Point to he is sitting.
   Stimulus: Point to she is jumping.
   Point to they are jumping.
   Point to he is jumping.
   Point to she is jumping.
   Stimulus: Point to he is standing.
   Point to he is standing.
   Point to they are standing.
   Point to she is standing.
   Stimulus: Point to she is kicking.
   Point to they are kicking.
   Point to she is kicking.
   Point to he is kicking.
   Stimulus: Point to they are eating.
   Point to he is eating.
   Point to she is eating.
   Point to they are eating.

Level 6

27. Tense and Aspect: will
   Stimulus: The girl will open the present.

The girl opened the present.
The girl is opening the present.
The girl will open the present.
Stimulus: The boy will eat his dinner.
The boy ate his dinner.
The boy will eat his dinner.
The boy is eating his dinner.
Stimulus: The boy will trip over the rock.
The boy will trip over the rock.
The boy is tripping over the rock.
The boy tripped over the rock.
Stimulus: The man will sew his shirt.
The man is sewing his shirt.
The man sewed his shirt.
The man will sew his shirt.
Stimulus: The girl will paint a picture.
The girl is painting a picture.
The girl will paint a picture.
The girl painted a picture.

28. Possessive Morpheme /'s/
   Stimulus: Show me the baby bear.
   Show me the baby's bear.
   Show me the baby bear.
   Stimulus: Show me the chicken's dinner.
   Show me the chicken's dinner.
   Show me the chicken dinner.
   Stimulus: Show me the mama cat.
   Show me the mama cat.
   Show me the mama's cat.
   Stimulus: Show me the baby's duck.
   Show me the baby duck.
   Show me the baby's duck.
   Stimulus: Show me the baby's bunny.
   Show me the baby bunny.
   Show me the baby's bunny.

29. Case Marking Prepositions: With
   Stimulus: Show me the breakfast made with mom.
   Show me the breakfast made for mom.
   Show me the breakfast made by mom.
   Show me the breakfast made with mom.
   Stimulus: Show me the suitcase being carried with the man.
   Show me the suitcase being carried by the man
   Show me the suitcase being carried with the man.
   Show me the suitcase being carried for the man.
   Stimulus: Show me the baby walking with the girl.
   Show me the baby walking with the girl.
   Show me the baby walking to the girl.
   Show me the baby walking from the girl.
   Stimulus: Show me the boy running with the girl.
   Show me the boy running with the girl.
   Show me the boy running from the girl.
   Show me the boy running to the girl.
   Stimulus: Show me the groceries being carried with mom
   Show me the groceries being carried for mom.
   Show me the groceries being carried with mom.
   Show me the groceries being carried by mom.

30. Double Embedding
   Stimulus: The clown that is chasing the girl that is little is big.
   The clown that is chasing the girl that is big is little.
   The clown that is chasing the girl that is little is little.
   The clown that is chasing the girl that is big is big.
   The clown that is chasing the girl that is little is big.
   Stimulus: The clown that is holding the balloon that is red is blue.
   The clown that is holding the balloon that is blue is blue.
   The clown that is holding the balloon that is red is blue.
   The clown that is holding the balloon that is red is red.
   The clown that is holding the balloon that is blue is red.
   Stimulus: The girl that is chasing the clown that is big is little.
   The girl that is chasing the clown that is big is big.
   The girl that is chasing the clown that is little is big.
   The girl that is chasing the clown that is big is little.
   The girl that is chasing the clown that is little is little.
   Stimulus: The clown that is holding the balloon that blue is red.
   The clown that is holding the balloon that is blue is red.
   The clown that is holding the balloon that is red is red.
   The clown that is holding the balloon that is red is blue.
   The clown that is holding the balloon that is blue is blue.
   Stimulus: The girl that is chasing the clown that is little is big.
   The girl that is chasing the clown that is big is big.
   The girl that is chasing the clown that is little is little.
   The girl that is chasing the clown that is little is big.
   The girl that is chasing the clown that is big is little.

31. Relativized Subject Ending in N-V-N
   Stimulus: The girl who is pushing the boy is happy
   The boy who is pushing the girl is mad.
   The girl who is pushing the boy is mad.
   The girl who is pushing the boy is happy.
   The boy who is pushing the girl is happy.
   Stimulus: The clown who is chasing the girl is little
   The clown who is chasing the girl is little.
   The girl who is chasing the clown is little.
   The girl who is chasing the clown is big.
   The clown who is chasing the clown is big.
   Stimulus: The boy who is pulling the girl is mad.
   The girl who is pulling the boy is happy.
   The boy who is pulling the girl is mad.
   The boy who is pulling the girl is happy.
   The girl who is pulling the boy is mad.
   Stimulus: The girl who is chasing the clown is little.
   The clown who is chasing the girl is big.
   The girl who is chasing the clown is big.
   The girl who is chasing the clown is little.
   The clown who is chasing the girl is little.

Level 7

32. Object Relativization
   Stimulus: The girl is chasing the clown who is big.
   The clown is chasing the girl who is little.
   The girl is chasing the clown who is big.
   The clown is chasing the girl who is big.
   The girl is chasing the clown who is little.
   Stimulus: The boy is pushing the girl who is happy.
   The boy is pushing the girl who is happy.
   The girl is pushing the boy who is happy.
   The girl is pushing the boy who is mad.
   The boy is pushing the girl who is mad.
   Stimulus: The girl is pulling the boy who is mad
   The boy is pulling the girl who is mad.
   The boy is pulling the girl who is happy.
   The girl is pulling the boy who is happy.
   The girl is pulling the boy who is mad.
   Stimulus: The boy is pushing the girl who is mad
   The boy is pushing the girl who is mad.
   The girl is pushing the boy who is mad.
   The girl is pushing the boy who is happy.
   The boy is pushing the girl who is happy.
   Stimulus: The girl is chasing the clown who is little.
   The clown is chasing the girl who is little.
   The girl is chasing the clown who is big.

The girl is chasing the clown who is little.
The clown is chasing the girl who is big.
33. Reduced Subject Relative Clauses ending in -V-N
   Stimulus: The girl pushing the boy is smiling
   The girl pushing the boy is smiling.
   The boy pushing the girl is smiling.
   The girl pushing the boy is frowning.
   The boy pushing the girl is frowning.
   Stimulus: The clown chasing the girl is little
   The clown chasing the girl is big.
   The girl chasing the clown is big.
   The clown chasing the girl is little.
   The girl chasing the clown is little.
   Stimulus: The girl pulling the boy is frowning.
   The girl pulling the boy is smiling.
   The boy pulling the girl boy is frowning.
   The boy pulling the girl is smiling.
   The girl pulling the boy is frowning.
   Stimulus: The girl chasing the clown is little.
   The clown chasing the girl is little.
   The girl chasing the clown is little.
   The clown chasing the girl is big.
   The girl chasing the clown is big.
   Stimulus: The boy pulling the girl is frowning
   The girl pulling the boy is smiling.
   The boy pulling the girl is frowning.
   The girl pulling the boy is frowning.
   The boy pulling the girl is smiling.
34. Who vs. What
   Stimulus: What is in the wagon? (ball)
   Is nothing in the wagon?
   Who is in the wagon?
   What is in the wagon? (ball)
   Stimulus: Who is in the tub? (man)
   What is in the tub?
   Who is in the tub? (man)
   Is nothing in the tub?
   Stimulus: What is under the table (cup)
   Who is under the table?
   What is under the table?
   Is nothing under the table?
   Stimulus: What is on the chair? (ball)
   What is on the chair? (ball)
   Is nothing on the chair?
   Who is on the chair?
   Stimulus: Who is on the box (clown)
   Who is on the box?
   What is on the box?
   Is nothing on the box?

Level 8

35. Verb Plural
   Stimulus: The deer eat.
   The dear eats.
   The deer eat.
   Stimulus: The sheep jump.
   The sheep jump.
   The sheep jumps
   Stimulus: The fish swim.
   The fish swims.
   The fish swim.
   Stimulus: The deer stand.
   The deer stands.
   The deer stand.
   Stimulus: The sheep eat.
   The sheep eat.
   The sheep eats.
36. Relative Pronouns with Double Function
   Stimulus: The girl who the boy girl who the boy is pushing is happy The girl who the boy is pushing is mad.
   The boy who the girl is pushing is mad.
   The girl who the boy is pushing is happy.
   The boy who the girl is pushing is happy.
   Stimulus: The boy who the girl is pulling is mad.
   The boy who the girl is pulling is mad.
   The boy who the girl is pulling is happy.
   The girl who the boy is pulling is happy.
   The girl who the boy is pulling is mad.
   Stimulus: The girl who the clown is chasing, is chasing the boy.
   The clown who the boy is chasing, is chasing the girl.
   The girl who the clown is chasing, is chasing the boy.
   The clown who the girl is chasing, is chasing the boy.
   Stimulus: The boy who the girl is pulling, is pulling the clown
   The girl who the boy is pulling, is pulling the clown.
   The clown who the boy is pulling, is pulling the girl.
   The clown who the girl is pulling, is pulling the boy.
   The boy who the girl is pulling, is pulling the clown.
   Stimulus: The boy who the girl is pushing, is happy.
   The boy who the girl is pushing is happy.
   The girl who the boy is pushing is sad.
   The boy who the girl is pushing is mad.
   The girl who the boy is pushing is happy.
37. Object Relatives with Relativized Objects
   Stimulus: The girl is hugging the boy that the clown is kissing.
   The girl is hugging the boy that is kissing
   The boy is hugging the girl that the clown
   The girl is hugging the boy that the clown
   The girl is hugging the clown that the boy
   Stimulus: The clown is hugging the girl that the boy is kissing
   The clown is hugging the boy that the girl is kissing.
   The clown is hugging the girl that the boy is kissing.
   The clown is hugging the girl that is kissing the boy.
   The girl is hugging the clown that the boy is kissing.
   Stimulus: The girl is kissing the clown that the boy is hugging
   The girl is kissing the boy that the clown is hugging.
   The clown is kissing the girl that the boy is hugging.
   The girl is kissing the clown that the boy is hugging.
   The girl is kissing the clown that is hugging the boy.
   Stimulus: The boy is hugging the girl that the clown is kissing
   The girl is hugging the boy that the clown is kissing.
   The boy is hugging the girl that is kissing the clown.
   The boy is hugging the clown that the girl is kissing.
   The boy is hugging the girl that the clown is kissing.
   Stimulus: The boy is kissing the girl that the clown is hugging
   The boy is kissing the girl that is hugging the clown.
   The girl is kissing the boy that the clown is hugging.
   The boy is kissing the girl that the clown is hugging.
   The boy is kissing the clown that the girl is hugging.
38. Clefting
   Stimulus: It's the clown that the girl chases.
   It's the girl that the clown chases.
   It's the boy that the clown chases.
   It's the boy that the girl chases.
   It's the clown that the girl chases.
   Stimulus: It's the boy that the girl kicks.
   It's the clown that the boy kicks.
   It's the clown that the girl kicks.
   It's the boy that the girl kicks.

It's the girl that the boy kicks.
Stimulus: It's the girl that the boy pulls.
It's the clown that the boy pulls.
It's the girl that the boy pulls.
It's the boy that the girl pulls.
It's the clown that the girl pulls.
Stimulus: It's the boy that the clown pushes.
It's the boy that the clown pushes.
It's the girl that the clown pushes.
It's the girl that the boy pushes.
It's the clown that the boy pushes.
Stimulus: It's the boy that the clown chases.
It's the girl that the boy chases.
It's the clown that the boy chases.
It's the boy that the clown chases.
It's the girl that the clown chases.

39. Negative-Passive

Stimulus: The cat is not being outrun by the dog.
The cat is not being outrun by the dog.
The dog is not being outrun by the cat.
The boy is not being outrun by the cat.
Stimulus: The drawing is not to be received by the girl
The drawing is not to be received by the girl.
The drawing is not to be received by the woman.
The drawing is not to be received by the girl.
Stimulus: The boy is not followed by the girl.
The girl is not followed by the boy.
The boy is not followed by the girl.
The clown is not followed by the boy.
Stimulus: The picture is not to be received from the boy
The picture is not to be received from the boy.
The picture is not to be received from the man.
The picture is not to be received from the girl.
Stimulus: The clown is not led by the girl.
The clown is not led by the boy.
The girl is not led by the clown.
The clown is not led by the girl.

We claim:

1. A method for training the sensory perceptual system in a human on a computer, the method comprising:
   a) repetitively providing a first acoustic event to the human, the first acoustic event being stretched in the time domain;
   b) sequentially after a) providing a second acoustic event to the human for recognition, the second acoustic event being stretched in the time domain;
   c) requiring the human to recognize the second acoustic event within a predetermined time window; and
   d) if the human recognizes the second acoustic event within the predetermined time window, reducing the amount that the first and second acoustic events are stretched.

2. The method of claim 1 wherein the sensory perceptual system that is being trained is the processing of temporal acoustic events common in speech.

3. The method of claim 2 wherein the temporal acoustic events common in speech are phonemes.

4. The method of claim 1 wherein the human has abnormal processing of temporal acoustic events.

5. The method of claim 1 wherein the human is a language-learning impaired (LLI) child.

6. The method of claim 1 wherein the first acoustic event is a distractor phoneme.

7. The method of claim 6 wherein the distractor phoneme is provided to the human a random number of times.

8. The method of claim 7 wherein the random number of times that the distractor phoneme is provided varies between 3 and 8.

9. The method of claim 1 wherein a) further comprises:
   a1) separating each provision of the first acoustic event by a predetermined inter-stimulus interval (ISI).

10. The method of claim 9 wherein the ISI is initially set to 500 ms.

11. The method of claim 9 wherein b) occurs after the same predetermined ISI.

12. The method of claim 1 wherein the second acoustic event is a target phoneme.

13. The method of claim 1 wherein both the first and second acoustic events are stretched in the time domain, without alteration of their frequency components.

14. The method of claim 1 wherein both the first and second acoustic events are phonemes that are initially stretched 150 percent in the time domain.

15. The method of claim 1 wherein c) further comprises:
    C1) requiring the human to indicate recognition of the second acoustic event by release of a computer button.

16. The method of claim 1 wherein c) further comprises:
    C1) requiring the human to indicate recognition of the second acoustic event by depressing a computer button.

17. The method of claim 1 wherein the predetermined time window is selected to accurately determine whether the human as distinguished between the repetitively provided first acoustic event and the second acoustic event.

18. The method of claim 1 further comprising:
    e) reducing the amount that the first and second acoustic events are stretched to 125 percent of normal speech.

19. The method of claim 10 further comprising:
    a2) progressively reducing the ISI between provisions of the first acoustic event and the second acoustic event as the human successfully recognizes the second acoustic event.

20. A method for training an LLI subject to distinguish between frequency sweeps common in phonemes, the method comprising:
    a) presenting a first frequency sweep that increases in frequency;
    b) presenting a second frequency sweep that decreases in frequency, the first and second frequency sweeps separated by an inter-stimulus interval (ISI);
    c) wherein a) and b) occur in random order;
    d) requiring an individual to recognize the order of presentation of the first and second frequency sweeps;
    e) reducing or increasing the ISI separating the first and second frequency sweeps as the individual recognizes or fails to recognize the order of presentation, respectively; and
    f) reducing the duration of the first and second frequency sweeps as the individual repeatedly recognizes their order of presentation.

21. The method of claim 20 wherein the frequency sweeps common in phonemes are sweeps of approximately sixteen octaves per second.

22. The method of claim 21 wherein the frequency sweeps common in phonemes are at approximately 500 hz, 1 khz and 2 khz.

23. The method of claim 20 wherein the first frequency sweep and the second frequency sweep, initially each have a duration of approximately 80 ms.

24. The method of claim 20 wherein the first frequency sweep (F), and the second frequency sweep (S), are presented in the order: F-F, F-S, S-F or S-S.

25. The method of claim 20 wherein d) further comprises:
    d1) presenting a first graphic image associated with the first frequency sweep;

d2) presenting a second graphic image associated with the second frequency sweep;

d3) requiring the individual to select the first graphic image and the second graphic image, as appropriate, to correspond to the order of presentation of the first and second frequency sweeps.

26. The method of claim 25 wherein the individual selects the first and second graphic images, as appropriate, by using a computer input device to designate selection.

27. The method of claim 20 wherein the individual recognizes the order of presentation of the first and second frequency sweeps by selecting a graphical representation associated with each of the sweeps on a computer.

28. The method of claim 20 wherein the ISI separating the first and second frequency sweeps is reduced when the individual properly recognizes their order of presentation in multiple trials.

29. The method of claim 28 wherein the number of multiple trials that must be properly recognized before the ISI is reduced is 3.

30. The method of claim 20 wherein the ISI separating the first and second frequency sweeps is increased when the individual fails to recognize their order of presentation after a single trial.

31. The method of claim 20 wherein the duration of the first and second frequency sweeps is reduced after the individual repeatedly recognizes their order of presentation with an ISI that is common in speech.

32. The method of claim 31 wherein the ISI that is common in speech is less than 130 ms.

33. The method of claim 31 wherein the ISI that is common in speech is between 110 and 125 ms.

34. A method for repetitively and adaptively training a subject, having subnormal temporal acoustic processing capabilities, to distinguish between phonemes having similar acoustic characteristics, the method comprising:

a) providing a plurality of phoneme pairs, each pair having similar acoustic characteristics;

b) for each of the plurality of phoneme pairs, providing a pair of associated graphic images;

c) selecting from among the plurality of phoneme pairs, a phoneme pair to be presented to the subject;

d) processing the selected phoneme pair according to a predetermined skill level;

e) presenting to the subject the processed selected phoneme pair;

f) as a trial, requiring the subject to recognize one of the processed phonemes from the selected phoneme pair by selecting its associated graphic image; and g) repeating c) through f).

35. The method as recited in claim 34 wherein the phoneme pairs comprise: aba-ada; ba-da; be-de; bi-di; and va-fa.

36. The method as recited in claim 34 wherein each pair of phonemes contain a distractor phoneme and a target phoneme.

37. The method as recited in claim 34 wherein the associated graphic images are animals.

38. The method as recited in claim 37 wherein the animals appear to speak the phonemes.

39. The method as recited in claim 34 wherein d) comprises:

d1) determining the skill level for the processing;

d2) stretching the consonant portions of each of the phonemes in the phoneme pair;

d3) emphasizing selected frequency envelopes within each of the phonemes in the phoneme pair;

d4) separating the stretched and emphasized phonemes by an inter-stimulus interval (ISI);

d5) wherein the amount of stretching, emphasizing and separating applied by d2) through d4) depends on the determined skill level.

40. The method as recited in claim 39 wherein d1) stretches the consonant portions of each of the phonemes in the time domain, without significantly affecting frequency components of the phonemes.

41. The method as recited in claim 39 wherein d1) stretches the consonant portions of each of the phonemes between 100 and 150 percent depending on the determined skill level.

42. The method as recited in claim 39 wherein the selected frequency envelopes within each of the phonemes are emphasized between 0 and 20 dB depending on the determined skill level.

43. The method as recited in claim 39 wherein the stretched and emphasized phonemes are separated by an ISI of between 0 and 500 ms depending on the determined skill level.

44. The method as recited in claim 39 wherein the determined skill level is related to whether the subject correctly recognized one of the processed phonemes from the selected phoneme pair in a previous trial.

45. The method as recited in claim 34 wherein e) comprises:

e1) presenting one of the processed phoneme pairs as a target phoneme to the subject;

e2) after e1), presenting each of the processed phonemes within the phoneme pair, in random order, separated by an inter-stimulus interval (ISI); and e3) during presenting each of the processed phonemes, graphically associating the presenting of each of the processed phonemes with their associated graphic images.

46. The method as recited in claim 45 wherein the subject recognizes the target phoneme, after e2), by selecting its associated graphic image.

47. The method as recited in claim 39 wherein the method contains a plurality of skill levels ranging from 150 percent stretching, 20 dB emphasis and 500 ms ISI to 100 percent stretching, 0 dB emphasis, and 0 ms ISI.

48. The method as recited in claim 34 wherein the predetermined skill level is determined according to the ability of the subject to recognize one of the processed phonemes from the selected phoneme pair.

49. The method as recited in claim 48 wherein as the subject repeatedly recognizes one of the processed phonemes from the selected phoneme pair, the skill level advances in difficulty.

50. The method as recited in claim 48 wherein as the subject fails to recognize one of the processed phonemes from the selected phoneme pair, the skill level decreases in difficulty.

51. A computer program product including a computer-usable medium having computer-readable code embodied thereon for training the sensory perceptual system in a human, the computer program product comprising:

a) computer-readable code configured to repetitively provide a first acoustic event to the human, said first acoustic event being stretched in the time domain;

b) computer-readable code configured to provide, sequentially after a), a second acoustic event to the human for recognition, said second acoustic event being stretched in the time domain;

c) computer-readable code configured to require the human to recognize said second acoustic event within a predetermined time window; and d) if the human recognizes said second acoustic event within said predetermined time window, computer-readable code configured to reduce an amount that said first and said second acoustic events are stretched.

52. The computer program product of claim 51 wherein a) further comprises:

a1) computer-readable code configured to separate each provision of said first acoustic event by a predetermined inter-stimulus interval (ISI).

53. The computer program product of claim 51 wherein both said first and said second acoustic events are stretched in the time domain, without alteration of their frequency components.

54. The computer program product of claim 51 further comprising:

e) if the human does not recognize said second acoustic event within said predetermined time window, computer-readable code configured to increase said amount that said first and said second acoustic events are stretched.

* * * * *